United States Patent
Xiao et al.

(10) Patent No.: US 11,162,960 B2
(45) Date of Patent: Nov. 2, 2021

(54) METHODS FOR GENERATING STRUCTURE-SWITCHING APTAMERS AND USES THEREOF

(71) Applicants: Yi Xiao, Miami, FL (US); Haixiang Yu, Miami, FL (US); Juan Canoura, Hialeah Gardens, FL (US); Yingzhu Liu, Miami, FL (US)

(72) Inventors: Yi Xiao, Miami, FL (US); Haixiang Yu, Miami, FL (US); Juan Canoura, Hialeah Gardens, FL (US); Yingzhu Liu, Miami, FL (US)

(73) Assignee: THE FLORIDA INTERNATIONAL UNIVERSITY BOARD OF TRUSTEES, Miami, FL (US)

( * ) Notice: Subject to any disclaimer, the term of this patent is extended or adjusted under 35 U.S.C. 154(b) by 220 days.

(21) Appl. No.: 16/437,021

(22) Filed: Jun. 11, 2019

(65) Prior Publication Data
US 2019/0376987 A1 Dec. 12, 2019

Related U.S. Application Data

(60) Provisional application No. 62/683,201, filed on Jun. 11, 2018.

(51) Int. Cl.
| | |
|---|---|
| *G01N 33/94* | (2006.01) |
| *C12N 15/115* | (2010.01) |
| *G01N 33/58* | (2006.01) |
| *C12Q 1/6811* | (2018.01) |

(52) U.S. Cl.
CPC ......... *G01N 33/946* (2013.01); *C12N 15/115* (2013.01); *C12Q 1/6811* (2013.01); *G01N 33/582* (2013.01); *C12Y 301/15* (2013.01); *C12Y 301/16* (2013.01)

(58) Field of Classification Search
None
See application file for complete search history.

(56) References Cited

U.S. PATENT DOCUMENTS

| | | | |
|---|---|---|---|
| 9,804,178 B2 | 10/2017 | Roncancio et al. | |
| 10,655,132 B1 * | 5/2020 | Yang | A61K 31/167 |
| 10,907,162 B2 * | 2/2021 | Yang | C12N 15/115 |

OTHER PUBLICATIONS

Neves, M.A.D., et al., "Defining the secondary structural requirements of a cocaine-binding aptamer by a thermodynamic and mutation study." Biophysical Chemistry, 2010,153: 9-16.

Roncancio, D., et al., "A Label-Free Aptamer-Fluorophore Assembly for Rapid and Specific Detection of Cocaine in Biofluids." Analytical Chemistry, 2014, 86: 11100-11106.

Wang, Z., et al., "Introducing structure-switching functionality into small-molecule-binding aptamers via nuclease-directed truncation." Nucleic Acids Research, 2018, 46(13), e81:1-11.

* cited by examiner

*Primary Examiner* — Tracy Vivlemore
(74) *Attorney, Agent, or Firm* — Saliwanchik, Lloyd & Eisenschenk

(57) ABSTRACT

The subject invention provides methods, assays, and products for detecting small-molecule targets in a complex sample in both clinical and field settings. The subject invention provides aptamer-based sensors and methods of use thereof. The subject invention provides exonuclease-based methods for generating structure-switching aptamers from fully folded or pre-folded aptamers and developing aptamer-based sensors for small-molecule detection. The method for detecting one or more small-molecule targets in a sample comprises contacting the sample with one or more aptamer-based sensor selective for each of the small-molecule targets, and detecting the small-molecule target in the sample.

20 Claims, 33 Drawing Sheets

Specification includes a Sequence Listing.

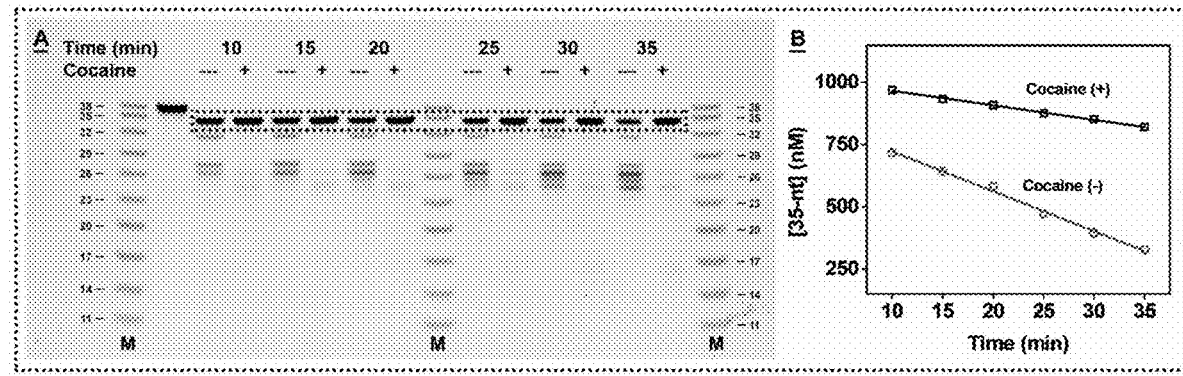
FIG. 3A    FIG. 3B
FIG. 4A    FIG. 4C
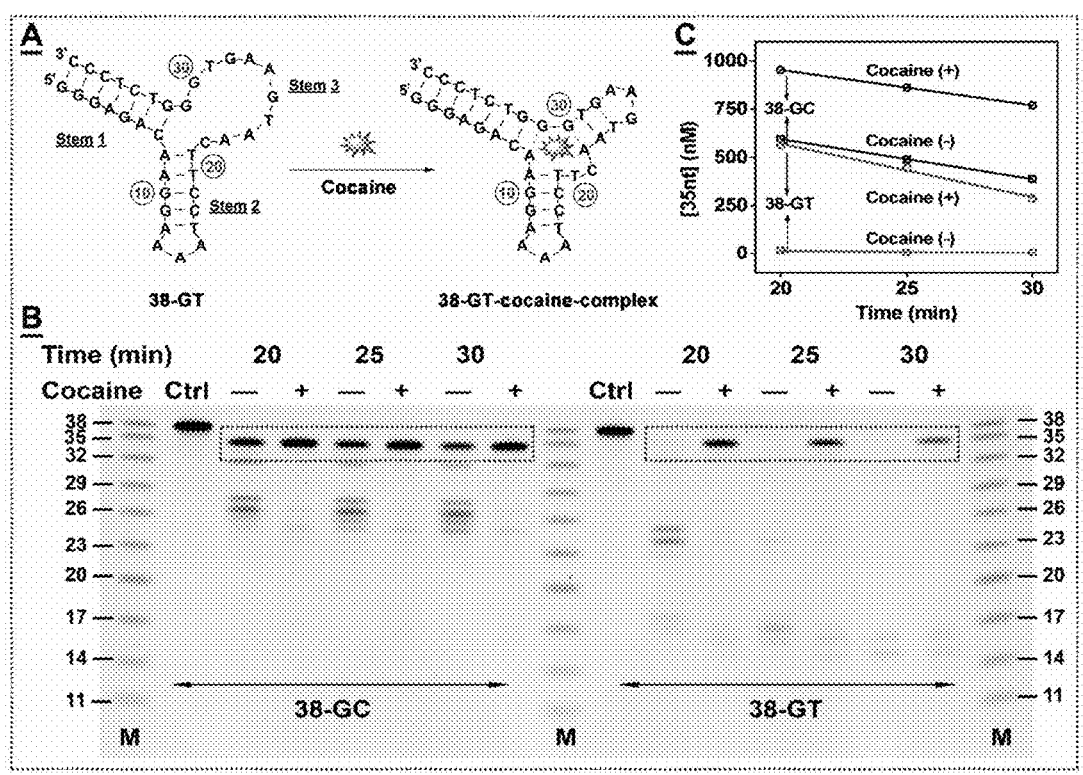
FIG. 4B

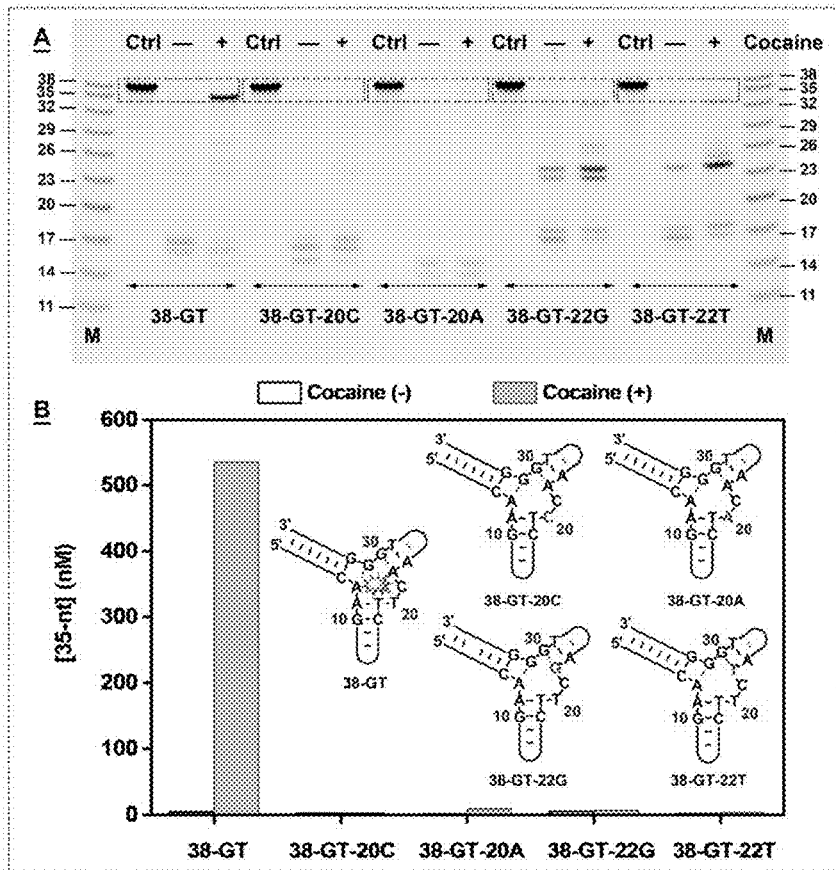
FIG. 8A
FIG. 8B
FIG. 9A                    FIG. 9B

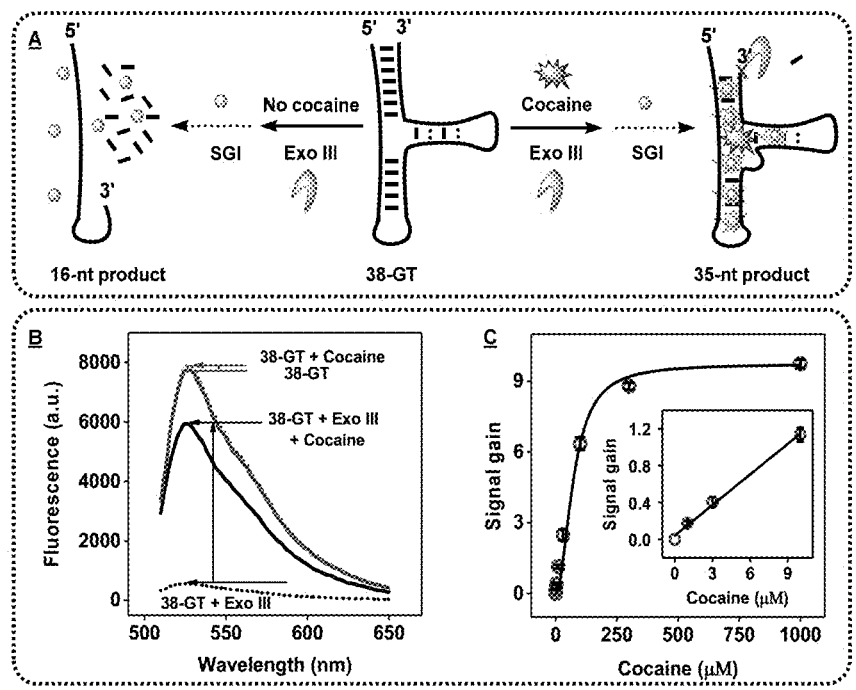
FIG. 10A
FIG. 10B  FIG. 10C
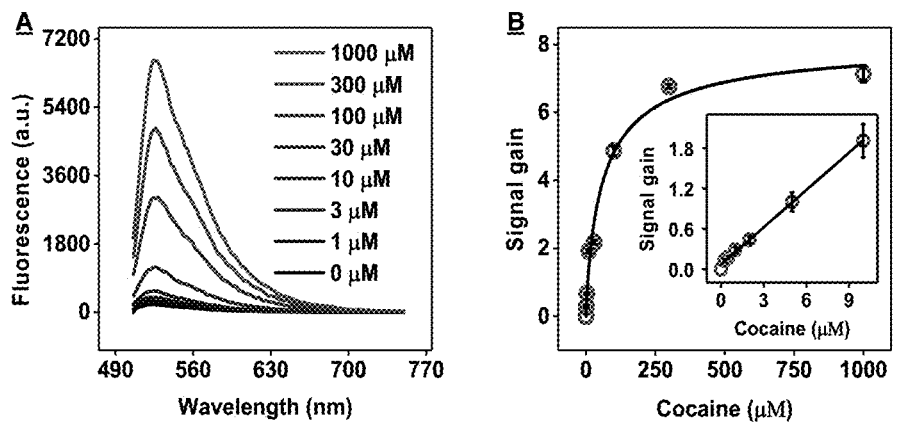
FIG. 11A  FIG. 11B

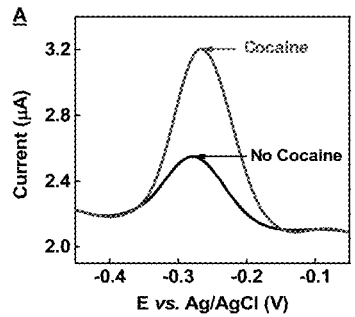 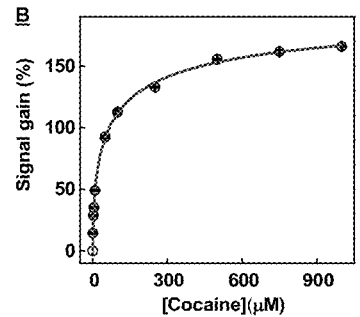 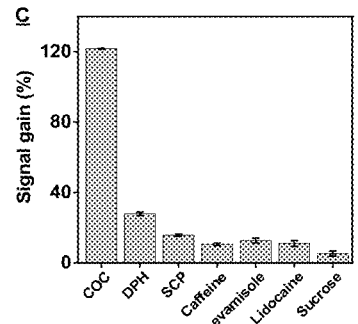
FIG. 16A        FIG. 16B        FIG. 16C
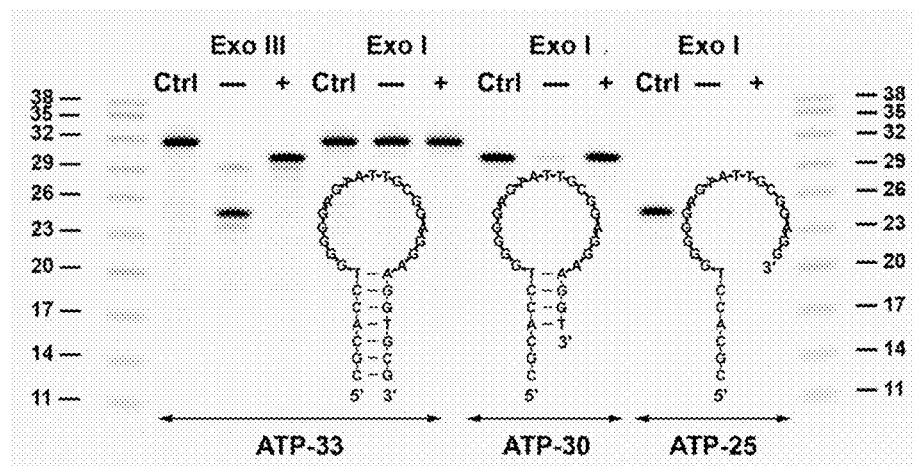
FIG. 17A    FIG. 17B    FIG. 17C

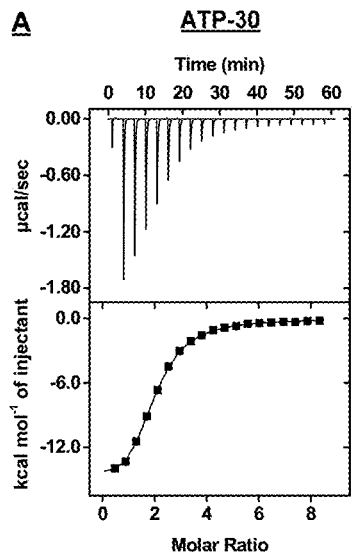
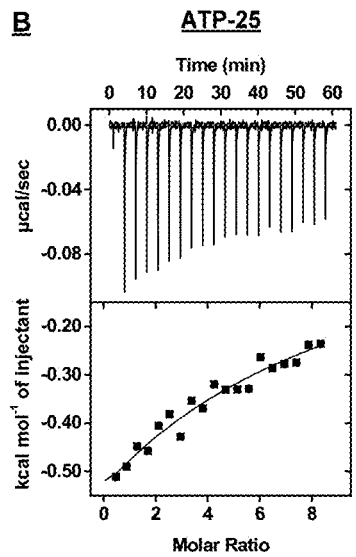
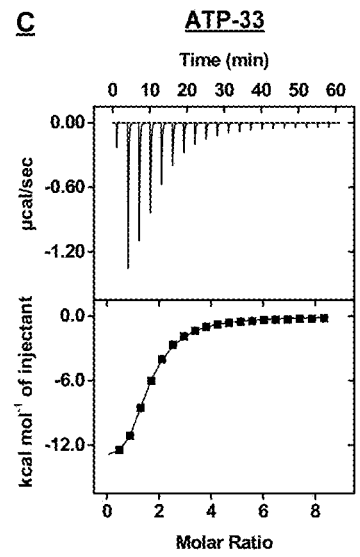
FIG. 18A  FIG. 18B  FIG. 18C
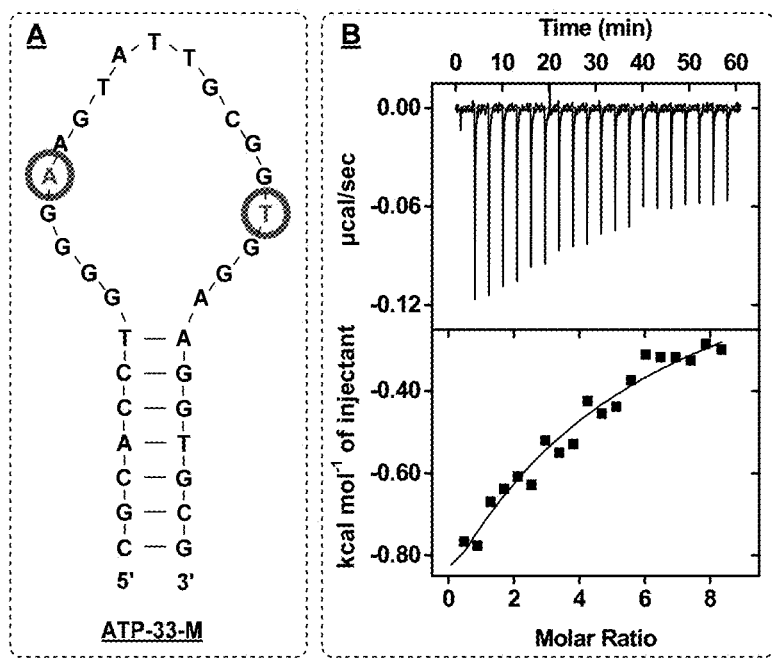
FIG. 19A  FIG. 19B

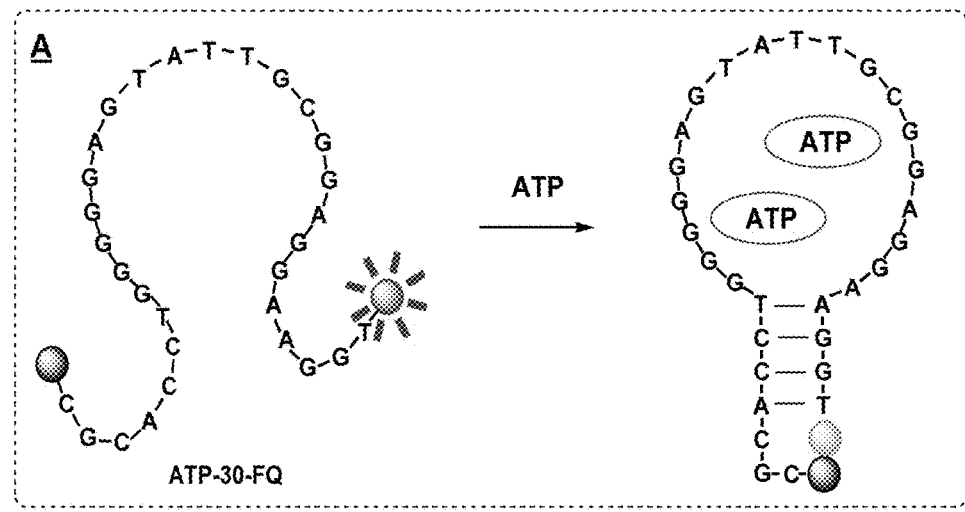
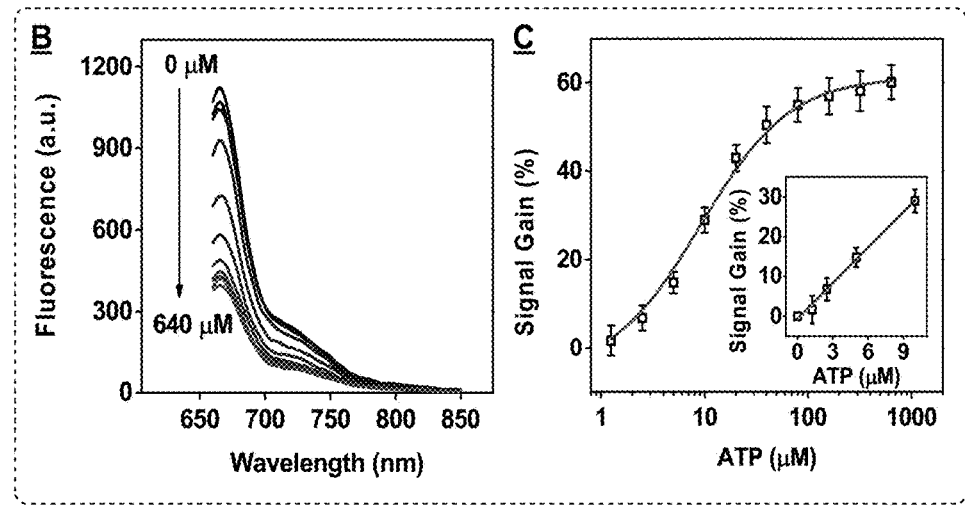
FIG. 24A
FIG. 24B
FIG. 24C

FIG. 25A
FIG. 25B
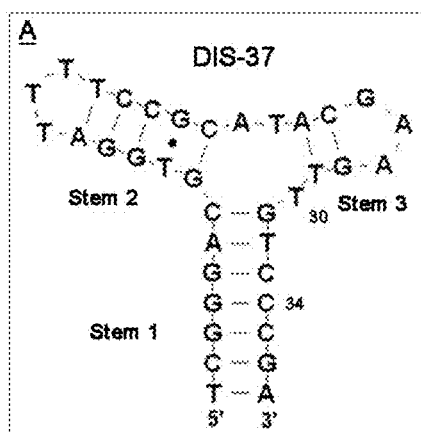
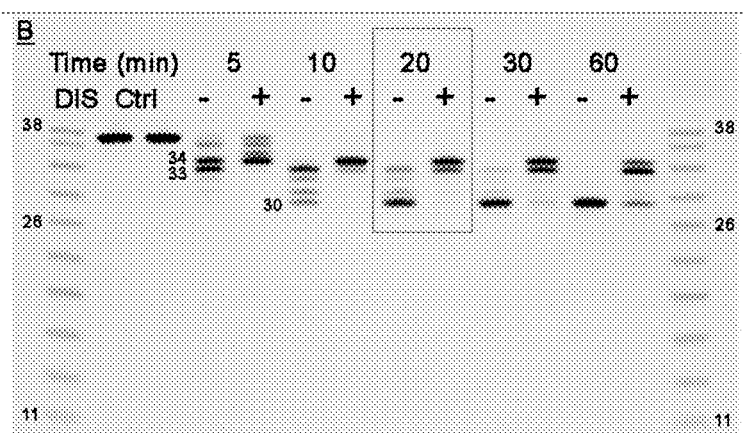
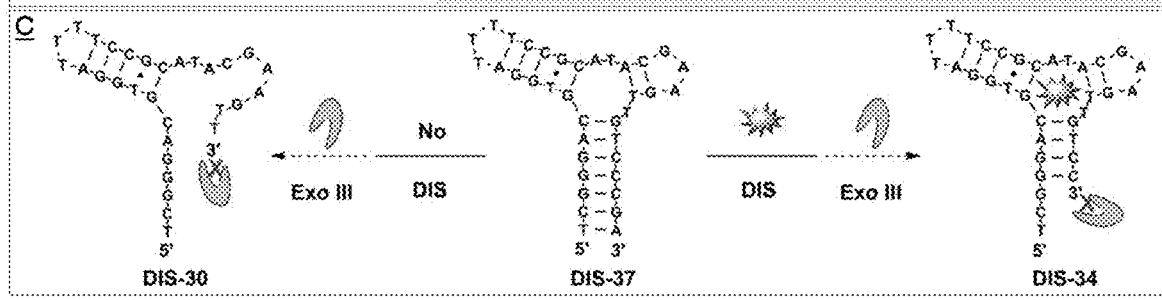
FIG. 25C

FIG. 31A    FIG. 31B
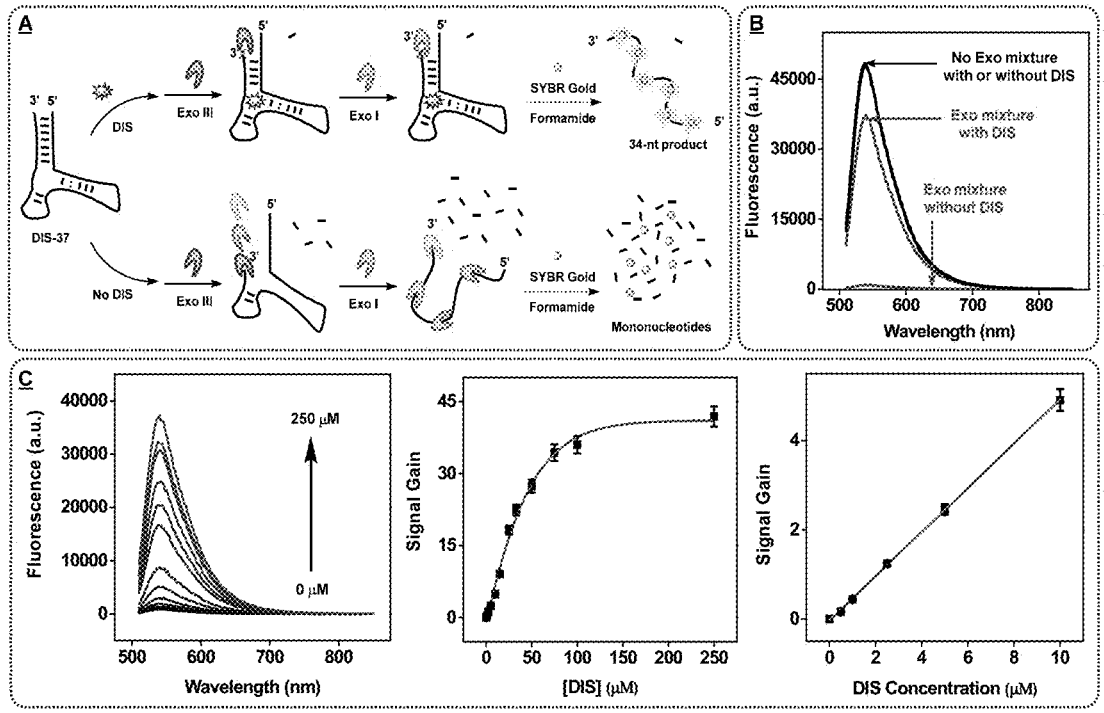
FIG. 31C
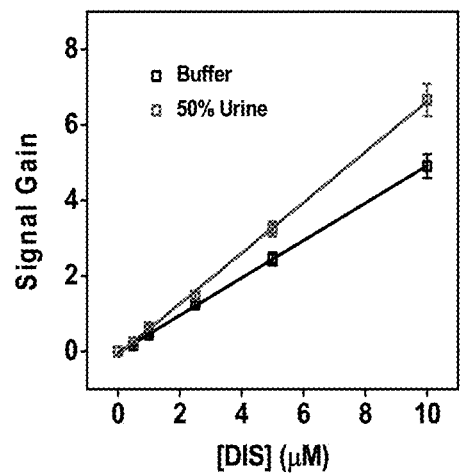
FIG. 32

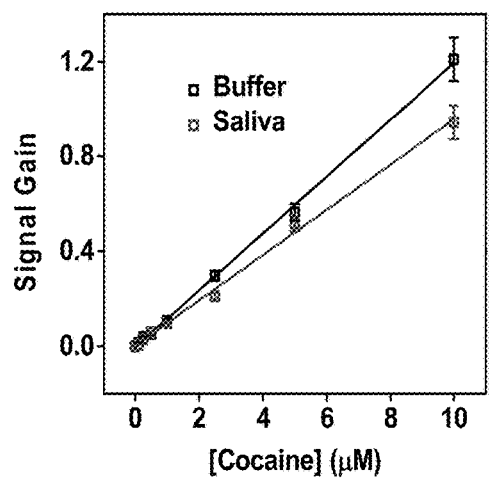
FIG. 37
FIG. 38A
FIG. 38C
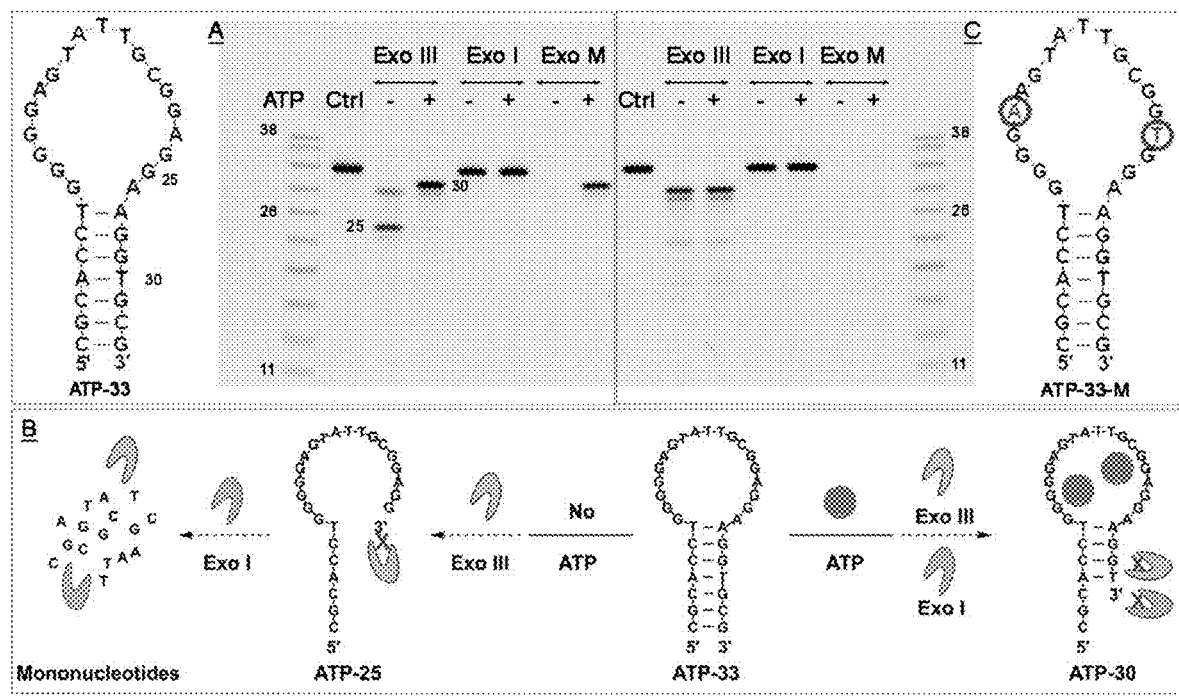
FIG. 38B

FIG. 39A
FIG. 39B
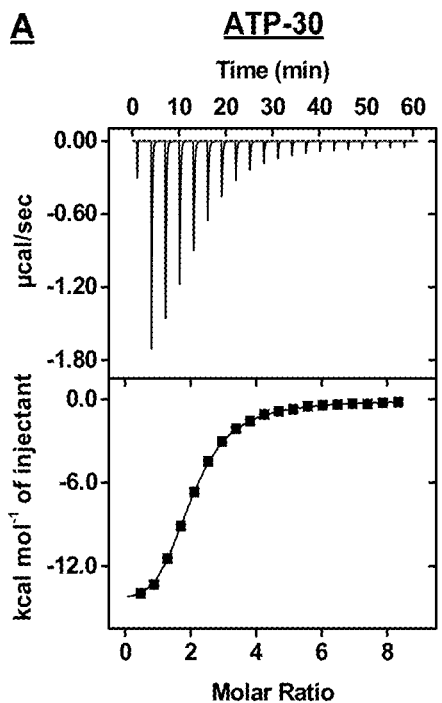
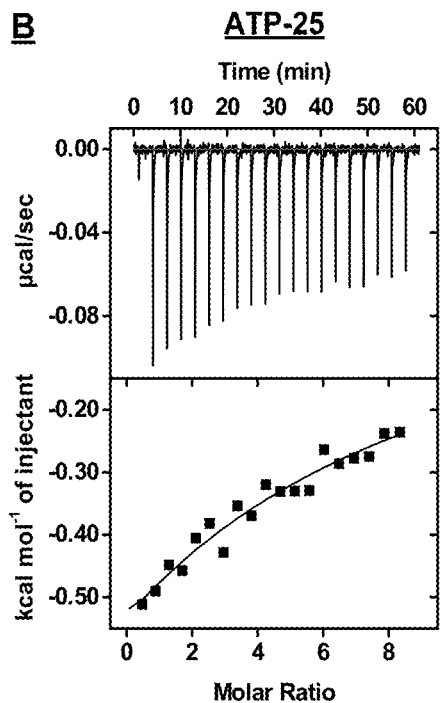
FIG. 39C
FIG. 39D
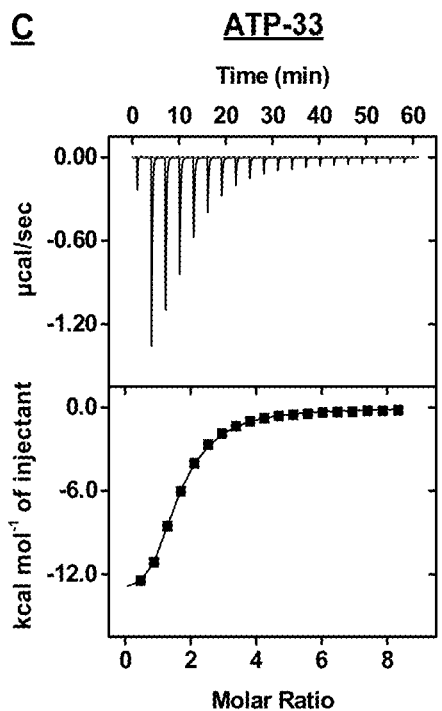
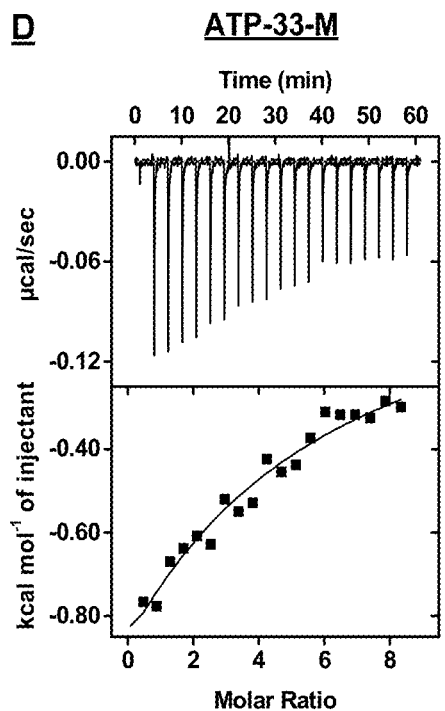

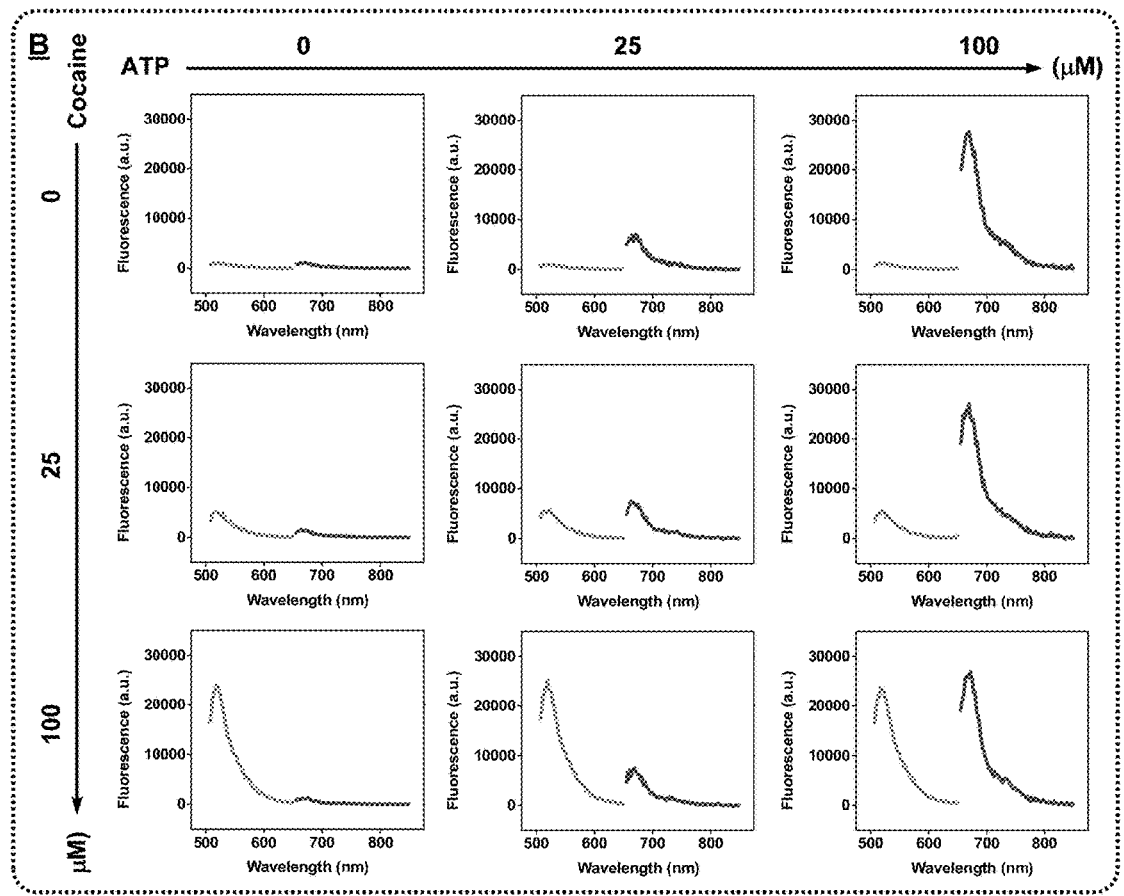
FIG. 44
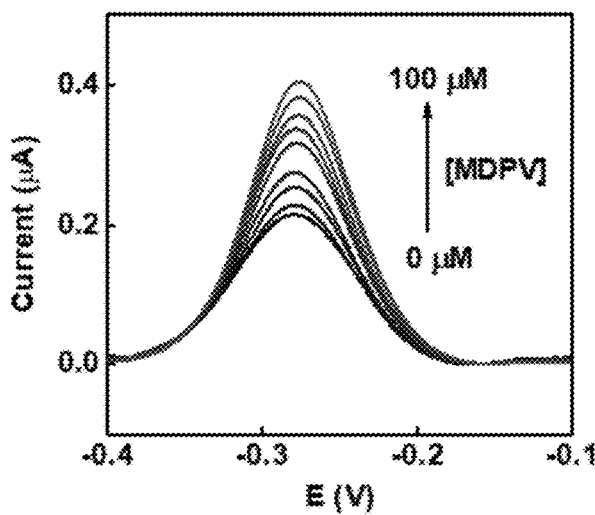
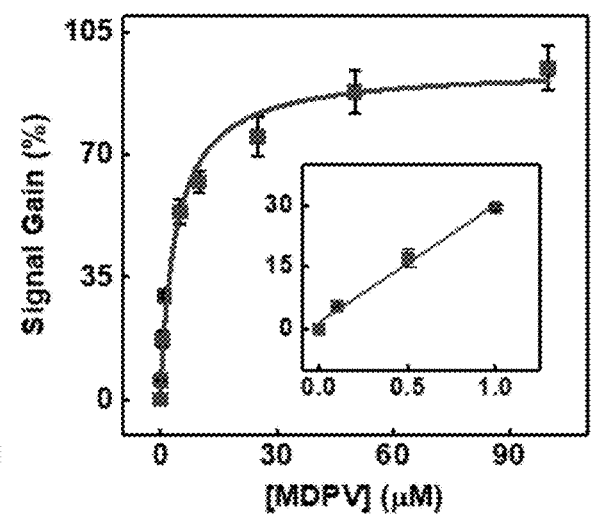
FIG. 45A  FIG. 45B

METHODS FOR GENERATING STRUCTURE-SWITCHING APTAMERS AND USES THEREOF

CROSS-REFERENCE TO A RELATED APPLICATION

This application claims the benefit of U.S. provisional application Ser. No. 62/683,201, filed Jun. 11, 2018, which is incorporated herein by reference in its entirety.

GOVERNMENT SUPPORT

This invention was made with government support under DA036821 awarded by the National Institutes of Health. The government has certain rights in the invention.

SEQUENCE LISTING

The Sequence Listing for this application is labeled "SeqList-09Jul21-ST25.txt," which was created on Jul. 9, 2021, and is 9 KB. The Sequence Listing is incorporated herein by reference in its entirety.

BACKGROUND OF THE INVENTION

The biosensor field is on a continuous quest for ever-greater sensitivity. In conventional bioassays, where the signal is directly proportional to the target concentration, the sensitivity is determined by the intrinsic target affinity of the bioreceptor being used for detection. In this scenario, it would be difficult to generate a measurable signal at target concentrations more than 100-fold lower than the dissociation constant ($K_D$) of the bioreceptor.

Small molecules are important targets with the potential of clinical or commercial applications. Thus, efforts to develop methods for portable, low-cost and quantitative detection of a broad range of small molecules are gaining momentum. Methods that are highly sensitive and selective, including high-performance liquid chromatography (HPLC) and gas chromatography-mass spectrometry (GC-MS), have been used for the detection of small molecules. However, these methods are time-consuming and require expensive reagents, advanced equipment, complex sample preparation, and/or trained operators.

Aptamers are nucleic acid-based affinity reagents, which can be isolated via in vitro systematic evolution of ligands by exponential enrichment (SELEX), to bind to various targets. They have gained considerable attention as biorecognition elements with diverse applications in areas such as drug screening, medical diagnostics, and environmental monitoring. This is in part because aptamers are chemically stable, offering long shelf lives, and can be synthesized at a low cost with high reproducibility. Aptamers can also be isolated for essentially any target, including metal ions, small molecules, proteins, or whole cells. Additionally, aptamers can be engineered to have tunable target-binding affinities or various functionalities. These advantages make aptamers ideal for use in biosensors.

Aptamer-based assays have been developed for the detection of many targets, particularly small molecules. Most aptamer-based assays for small molecule detection utilize structure-switching aptamers, which undergo a conformational change upon target binding.

Upon binding to the sensing aptamer, the target induces a specific folding event that produces a colorimetric, fluorescent or electrochemical readout. However, a majority of aptamers do not have inherent structure-switching functionality, and a multistep process is required to introduce this functionality for sensor development. First, the target-binding domain must be identified, usually through laborious truncation. Afterwards, sequence engineering, splitting, or a complementary strand that partially blocks the aptamer binding site is employed to confer structure-switching functionality. These methods are labor-intensive and require considerable trial and error. Moreover, engineered structure-switching aptamers often have low target-binding affinities, greatly limiting their utility.

Therefore, there is a need for methods and materials to rapidly introduce structure-switching functionality into small-molecule-binding aptamers for streamlined development of folding-based sensors as well as to develop a novel aptamer-based sensing strategy that does not require structure-switching aptamers.

BRIEF SUMMARY OF THE INVENTION

The subject invention provides methods, assays, and products for producing structure-switching aptamers and use thereof for detecting small molecule targets in a complex sample, in particular, in both clinical and field settings. In one embodiment, the subject invention provides exonuclease-based methods for both generating structure-switching aptamers from fully folded or pre-folded aptamers and developing aptamer-based sensors for small-molecule detection.

In one embodiment, the subject invention provides a method for generating structure-switching aptamers from fully folded or pre-folded aptamers and a means of rapid and sensitive detection of a small-molecule target. The generation of structure-switching aptamers entails digesting the aptamer with an exonuclease, such as Exo III. The resulting digestion product has structure-switching functionality with similar or equal affinity as its parent aptamer, and such aptamer can be directly employed in folding-based aptamer sensors.

In one embodiment, the method for generating a truncated aptamer having the structure-switching functionality, i.e., structure-switching aptamer, comprises providing a pre-folded parent aptamer that does not have the structure-switching functionality, wherein the pre-folded parent aptamer is specific for a small-molecule target, contacting the parent aptamer with an exonuclease, such as Exo III, and generating the structure-switching aptamer, the structure-switching aptamer having the same target-binding domain as the pre-folded parent aptamer; the structure-switching aptamer having a target-induced structure-switching functionality.

In one embodiment, the subject invention provides a method for detecting a small molecule target in a sample using the truncated aptamers having structure-switching functionality. The method comprises contacting the sample with an exonuclease-truncated aptamer having structure-switching functionality, which is selective for the small-molecule target, and detecting the small-molecule target in the sample.

In one embodiment, the detection of the small-molecule target further comprises measuring a signal generated upon binding of a signal reporter with the target-aptamer complex. In one embodiment, the exonuclease-truncated, structure-switching aptamer modified with a fluorophore-quencher pair, and the detection of the small-molecule target further comprises measuring a signal generated upon binding of the small-molecule target to the aptamer-based sensor.

In one embodiment, the subject invention provides methods for detecting a small-molecule target by incorporating exonuclease-truncated, structure-switching aptamers into an electrochemical aptamer-based (E-AB) sensor, which demonstrates target-induced conformational changes within the aptamers and achieves excellent sensor performance. In one embodiment, the method facilitates rapid and sensitive detection of a small-molecule target in a sample by contacting the sample with an E-AB sensor selective for the small-molecule target, and detecting the small-molecule target in the sample.

The methods according to the subject invention employ a rapid exonuclease-inhibition assay that can be generally implemented with unmodified fully folded or pre-folded parent aptamers for small-molecule-target detection. In one embodiment, in the absence of target, Exo III digests the aptamer to produce a single-stranded product, which can then be further digested by Exo I. In contrast, target-binding inhibits the digestion by Exo III, leaving behind a double-stranded, target-bound product that remains invulnerable to Exo I digestion. Thus, the methods detect small-molecules via the quantification of aptamer digestion products through different fluorescence-based methods.

In one embodiment, the subject invention further provides methods employing an exonuclease-inhibition fluorescence assay using exonuclease-directed truncation strategies.

This assay can achieve sensitive small-molecule detection via quantification of aptamer digestion products. Such assay does not require any prior sequence engineering, truncation, or labeling.

In one embodiment, the subject invention provides a method for rapid and sensitive detection of a small-molecule target in a sample comprising contacting the sample with an aptamer-based sensor selective for the small-molecule target, wherein the aptamer-based sensor comprises a fully folded or pre-folded aptamer and can be digested by a mixture of Exo III and Exo I, contacting the mixture of the sample and the aptamer-based sensor with a mixture of exonucleases III and I, adding a signal reporter, and detecting the small-molecule target in the sample, wherein the detection of the small-molecule target comprises measuring a signal generated from the signal reporter.

In one embodiment, the subject invention further provides methods for single-pot, multiplex small-molecule detection, which is a highly valuable and vital tool for medical diagnostics, drug screening, environmental monitoring, biodefence, and food safety as it enables detection of a multitude of analytes with only a single low-volume sample.

In one embodiment, the subject invention also provides methods for detecting one or more small-molecule targets in a sample comprising contacting the sample with one or more aptamer-based sensors selective for each of the small-molecule targets, wherein the one or more aptamer-based sensors are digested by, for example, Exo III and Exo I, and detecting one or more small-molecule target in the sample. The method further comprises adding one or more molecular beacons that specifically hybridize with each digested aptamer strand. The detection of one or more small-molecule targets further comprises measuring one or more signals generated upon reaction between one or more molecular beacons with each aptamer.

In one embodiment, the subject invention further provides a kit for detecting a small-molecule target, comprising an aptamer-based sensor and one or more exonucleases. The kit can further comprise instructions for using the kit. In some embodiments, the kit can comprise other reagents suitable for detecting the small-molecule target.

BRIEF DESCRIPTION OF THE DRAWINGS

FIGS. 3A-3B show the time course of 38-GC Exo III digestion in the absence or presence of cocaine. (3A) PAGE analysis of digestion products. The 35-nt major product is indicated by the box. (3B) Extent of 35-nt product degradation over time in the presence or absence of cocaine. [38-GC]: 1 µM, [cocaine]: 250 µM, [Exo III]: 0.26 U/µL.

FIGS. 4A-4C show the time-course of Exo III digestion for 38-GC and 38-GT in the absence or presence of cocaine. (4A) Secondary structure of unbound and cocaine-bound 38-GT (SED ID NO: 2). (4B) PAGE analysis of Exo III-digested products over time, with the 35-nt product indicated by the box. (4C) A plot of the estimated concentration of the 35-nt product over the course of digestion.

FIGS. 8A-8B show Exo III digestion of 38-GT is inhibited only upon binding to cocaine. (8A) PAGE analysis of Exo III digestion for 38-GT and four point mutants after a 25-minute reaction. The 35-nt product is indicated by the boxes. (8B) Concentrations of the 35-nt truncation product and secondary structures for 38-GT and four mutants, with mutations highlighted in red.

FIGS. 9A-9B show specific Exo III inhibition of cocaine-aptamer complexes. (9A) PAGE analysis of digestion products of 38-GT and the 38-GT-20A mutant at different cocaine concentrations up to 2 mM. The 35-nt product is indicated by the box. (9B) A plot of the estimated concentration of the 35-nt product at different concentrations of cocaine after a 25-min reaction. [aptamer]: 1 µM, [Exo III]: 0.26 U/µL.

FIGS. 10A-10C show Exo III-based fluorescence assay for cocaine detection. (10A) Schematic of cocaine detection based on Exo III inhibition of cocaine-bound aptamers (right) relative to the readily-digested unbound aptamer (left). (10B) Fluorescence spectra for Exo III-treated (black line) and untreated (red line) samples with or without 250

μM cocaine. (10C) Calibration curve with SYBR Green I. Inset depicts the signal gain from 0 to 10 μM target. Error bar represent standard deviation of three different measurements.

FIGS. 11A-11B show the use of the Exo III-based assay to detect cocaine in 10% saliva. (11A) Fluorescence spectra for Exo III-treated samples with different concentrations of cocaine in 10% saliva. (11B) Calibration curve with SYBR Green I. Inset depicts the signal gain from 0 to 10 μM. [38-GT]: 1 μM, [Exo III]: 0.26 U/μL.

Figure 12A:
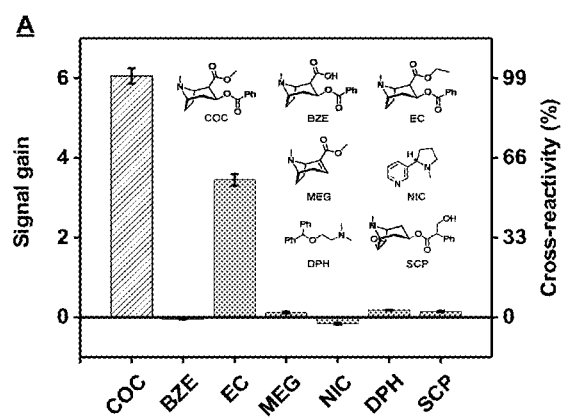
Figure 12B:
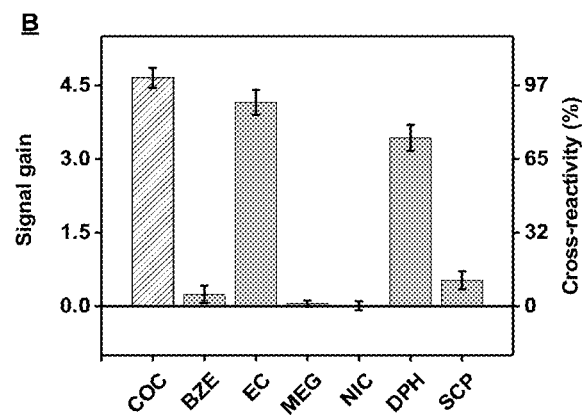
Figure 13A:
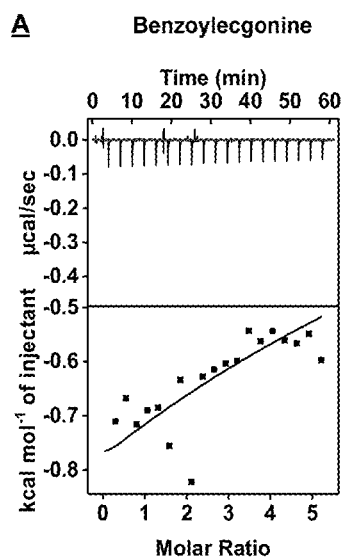
Figure 13B:
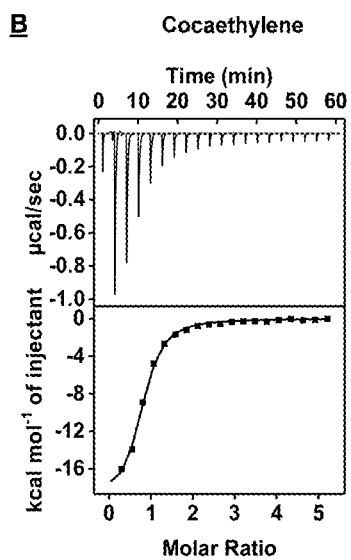
Figure 13C:
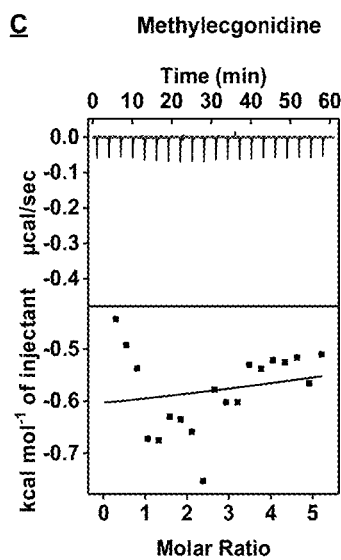
Figure 13D:
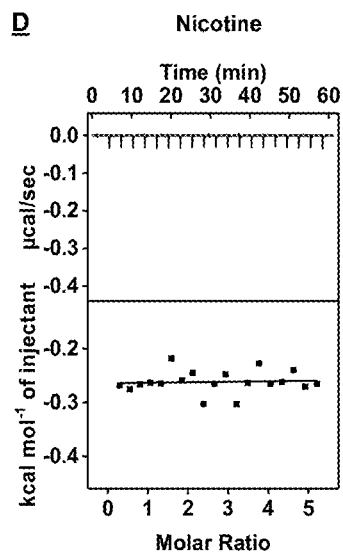
Figure 13E:
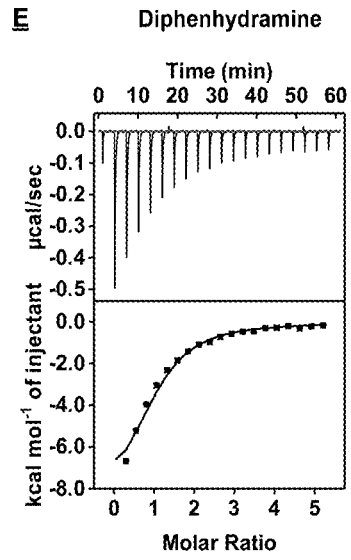
Figure 13F:
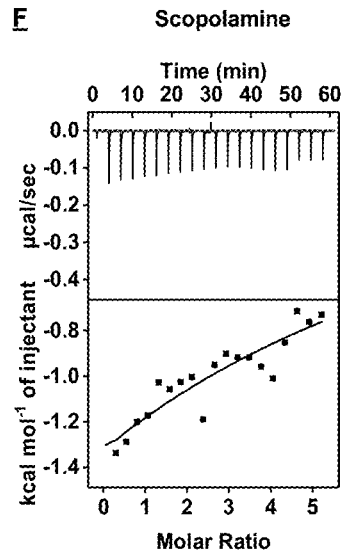

FIGS. 12A-12B show the Exo III-based fluorescence assay achieving high specificity for cocaine. (12A) Specificity of Exo III digestion in the presence of cocaine (COC), benzoylecgonine (BZM), cocaethylene (EC), methylecgonidine (MEG), nicotine (NIC), diphenhydramine (DPH), and scopolamine (SCP) in 10% saliva. [target/interferents]: 250 μM, [38-GT]: 1 μM, [Exo III]: 0.26 U/μl. (12B) Specificity of detection with 38-GT in an ATMND displacement assay using the same set of drugs. [target/interferents]: 250 μM, [38-GT]: 2 μM, [ATMND]: 0.25 μM.

FIGS. 13A-13F show the characterization of binding affinity of 38-GT to interferents using ITC. Top panels present raw data showing the heat generated from each titration of (13A) benzoylecgonine, (13B) cocaethylene, (13C) methylecgonidine, (13D) nicotine, (13E) diphenhydramine, and (13F) scopolamine to 38-GT. Bottom panels show the integrated heat of each titration after correcting for dilution heat of the titrant.

Figure 14:
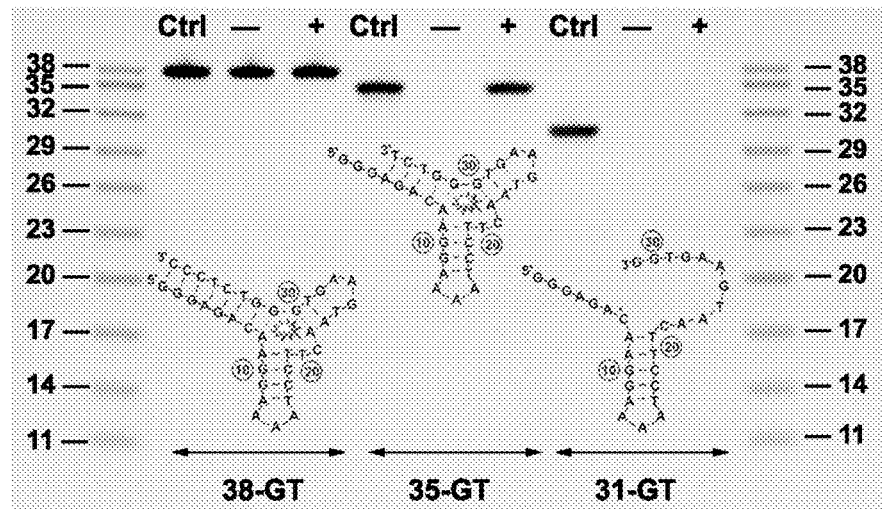

FIG. 14 shows PAGE analysis of Exo I digestion of aptamers after 30 minutes in the absence (−) or presence (+) of cocaine. Structure and PAGE analysis of digestion products for 38-GT (SEQ ID NO: 2), 35-GT (SEQ ID NO: 3), and 31-GT (SEQ ID NO: 4).

Figure 15:
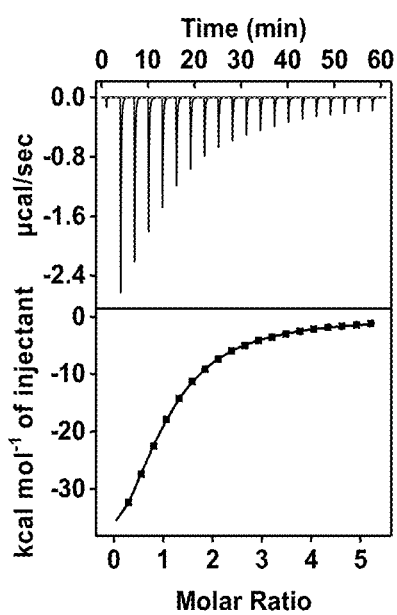

FIG. 15 shows the characterization of binding affinity of 35-GT to cocaine using ITC. Top panels present raw data showing the heat generated from titration of cocaine to 35-GT. Bottom panels show the integrated heat of each titration after correcting for dilution heat of the titrant.

FIGS. 16A-16C show the performance of an E-AB sensor based on the thiolated, methylene blue modified version of Exo III-truncated cocaine-binding aptamer 35-GT. (16A) Square-wave voltammetry curves of the sensor in the presence and absence of 1,000 μM cocaine. (16B) Calibration curve of the E-AB sensor for cocaine concentrations ranging from 0-1,000 μM. (16C) Specificity of the E-AB sensor against cocaine and interferents including diphenhydramine (DPH), scopolamine (SCP), caffeine, levimisole, lidocaine and sucrose. Error bars represent standard deviation of three experiments with three different electrodes.

FIGS. 17A-17C show PAGE analysis of Exo III or Exo I digestion of ATP-binding aptamers after 30 minutes, with (+) or without (−) ATP. Structure and gel analysis of digestion products for (17A) ATP-33 (SEQ ID NO: 10), (17B) ATP-30 (SEQ ID NO: 11), and (17C) ATP-25 (SEQ ID NO: 12 ).

FIGS. 18A-18C show the characterization of target-binding affinity of ATP-binding aptamers using ITC. Top panels present raw data showing the heat generated from each titration of ATP for (18A) ATP-30, (18B) ATP-25, and (18C) ATP-33. Bottom panels show the integrated heat of each titration after correcting for dilution heat of the titrant.

FIGS. 19A-19B show the affinity characterization of ATP-33-M using ITC. (19A) Secondary structure of ATP-33-M (SEQ ID NO: 14), with altered nucleotides in red circles. (19B) Top panels present raw data showing the heat generated from each titration of ATP for ATP-33-M. Bottom panels show the integrated heat of each titration after correcting for dilution heat of the titrant.

Figures 20A, 20B:
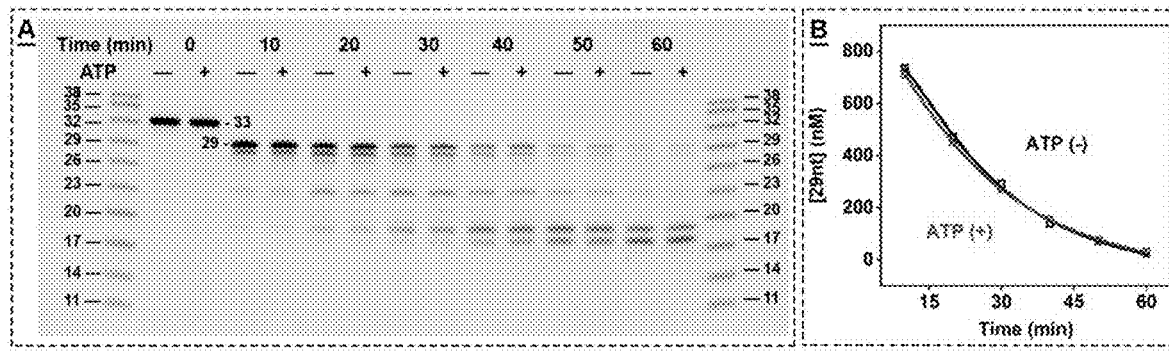

FIGS. 20A-20B show the time course of Exo III digestion for ATP-33-M in the absence or presence of ATP. (20A) PAGE analysis of Exo III-digestion products over time. (20B) A plot of the estimated concentration of the 29-nt major product over the course of digestion.

Figure 21:
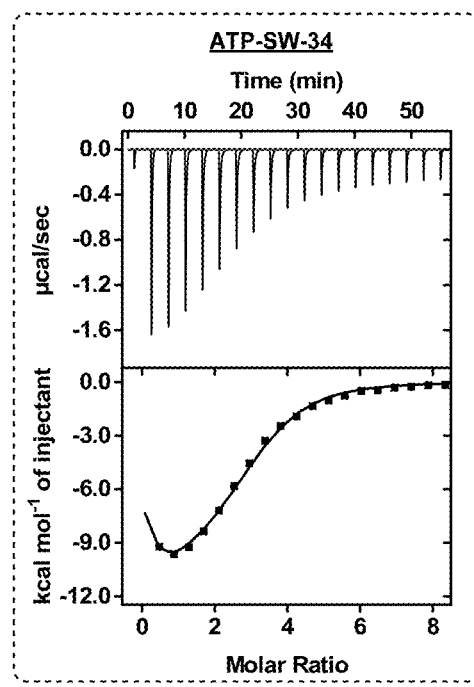

FIG. 21 shows the affinity characterization of structure-switching ATP-binding aptamer using ITC. Top panels present raw data showing the heat generated from each titration of ATP for ATP-SW-34. Bottom panels show the integrated heat of each titration after correcting for dilution heat of the titrant.

Figures 22A, 22B, 22C:
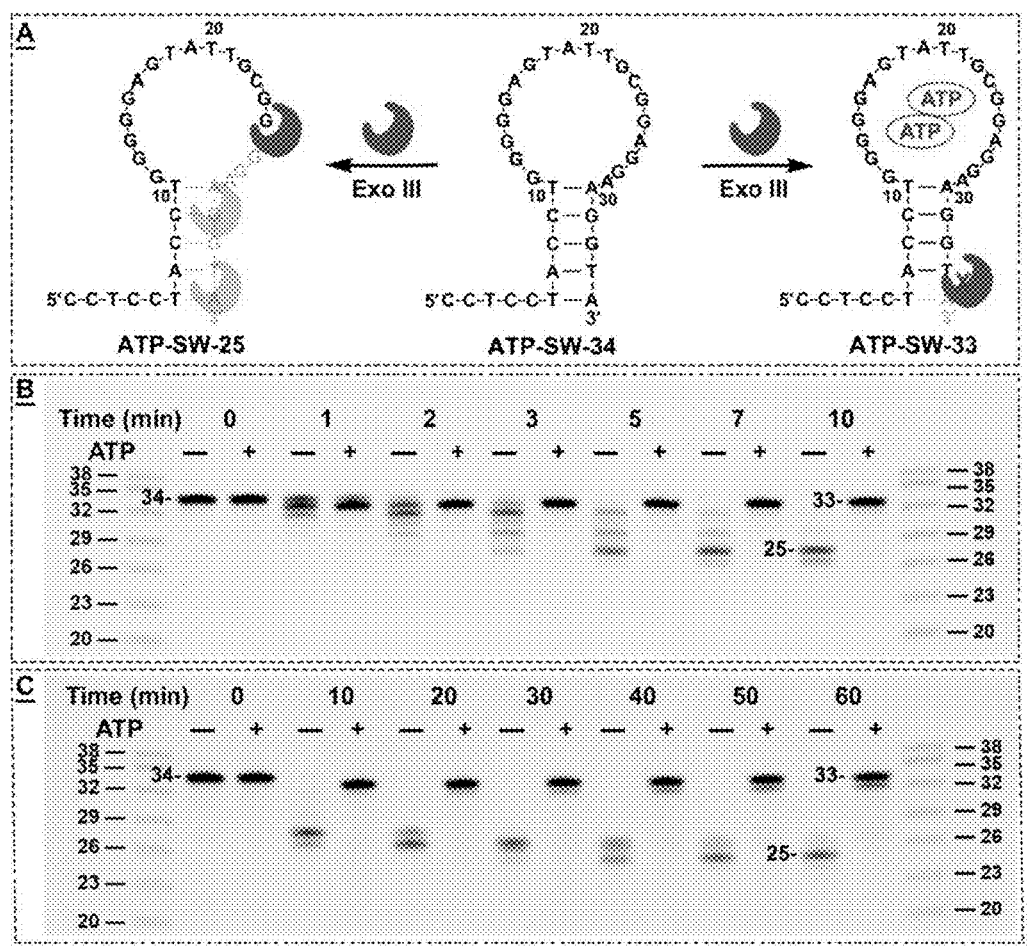

FIGS. 22A-22C show the time course of Exo III digestion for ATP-SW-34 in the absence or presence of ATP under the experimental conditions (22A) Schematic of Exo III digestion for ATP-SW-34 with or without target, arriving at a 33nt product, ATP-SW-33 (SEQ ID NO: 41) or a 25nt product, ATP-SW-25 (SEQ ID NO: 42). (22B, and 22C) PAGE analysis of Exo III-digestion products over (22B) 10 and (22C) 60 minutes.

Figures 23A, 23B, 23C:
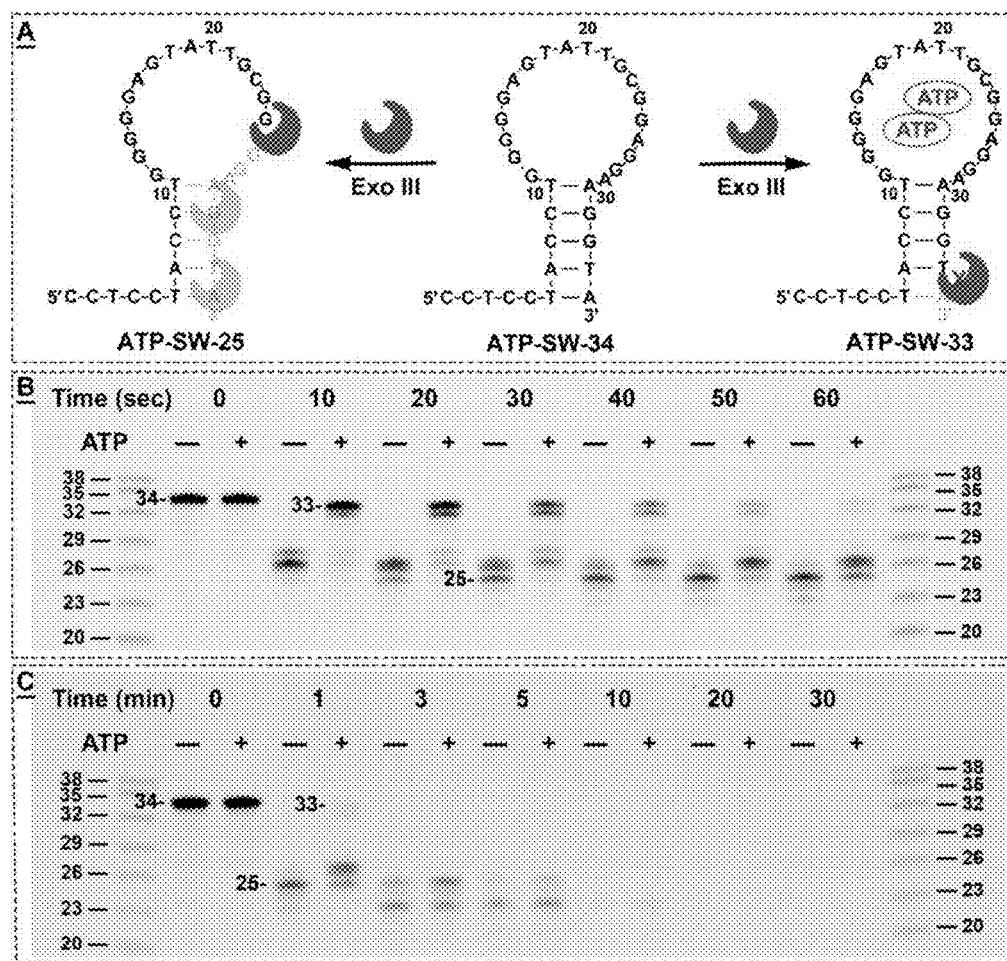
Figure 26A:
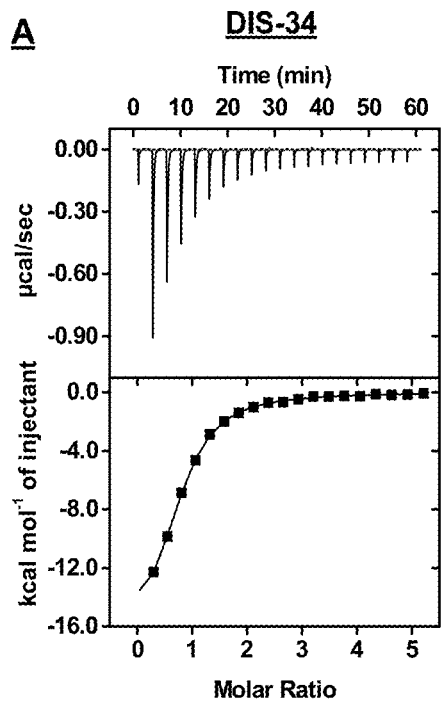
Figure 26B:
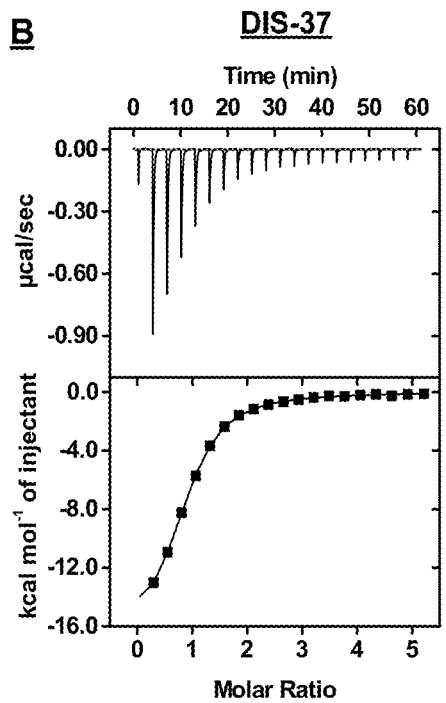
Figure 26C:
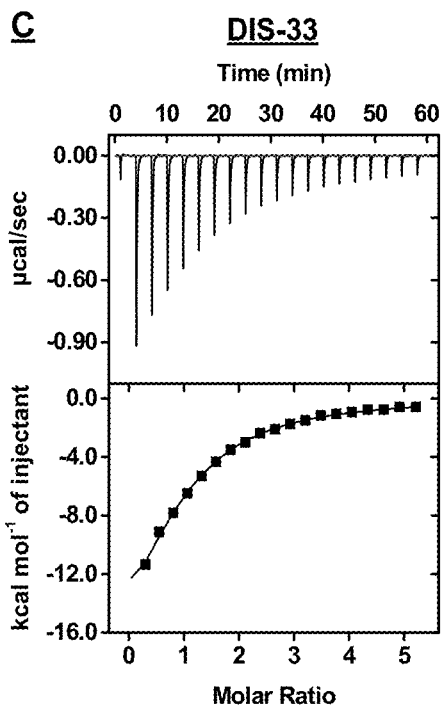
Figure 26D:
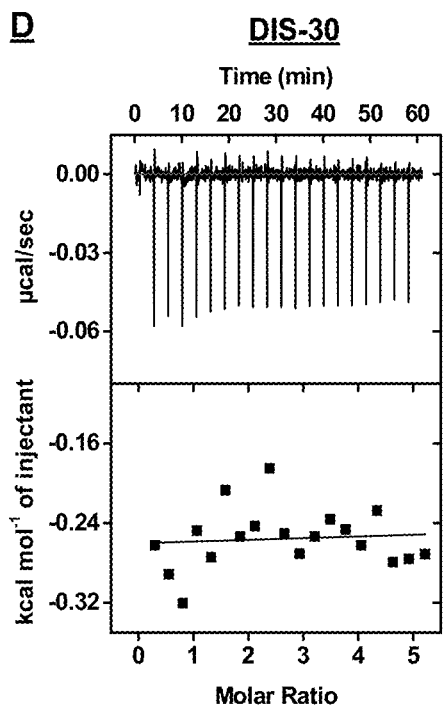

FIGS. 23A-23C show the time course of Exo III digestion for ATP-SW-34 in the absence or presence of ATP under the previously-reported experimental conditions. (23A) Schematic of Exo III digestion for ATP-SW-34 with or without target, arriving at a 33nt product, ATP-SW-33 (SEQ ID NO: 41) or a 25nt product, ATP-SW-25 (SEQ ID NO: 42). (23B-C) PAGE analysis of Exo III-digestion products over (23B) 1 minute and (23C) 30 minutes.

FIGS. 24A-24C show ATP detection with a fluorophore-quencher assay based on the 3' Cy5 fluorophore and a 5' IowaBlack quencher modified version of an Exo III-truncated ATP-binding aptamer, ATP-30. (24A) The ATP-30-FQ (SEQ ID NO: 13) construct is initially single-stranded, producing strong fluorescence. ATP binding promotes aptamer folding, resulting in quenched fluorescence. (24B) Fluorescence spectra of ATP detection. From top to bottom, curves depict fluorescence spectra in the presence of 0, 1.25, 2.5, 5, 10, 20, 40, 80, 160, 320, or 640 μM ATP. (24C) Calibration curve of the assay. Signal gain was calculated using the equation $(F-F_0)/F_0$ where $F$ and $F_0$ represent fluorescence intensity at 545 nm in the presence and absence of ATP, respectively. Inset shows the linear range from 0-10 μM ($R^2=0.9991$). Error bars represent standard deviation of three measurements.

FIGS. 25A-25C show the time-course of Exo III digestion of a DIS-binding aptamer in the absence or presence of DIS. (25A) Secondary structure of DIS-37(SEQ ID NO: 17). (25B) PAGE analysis of DIS-37 digestion products over 60 minutes with or without DIS, arriving at DIS-34 (SEQ ID NO: 18) or DIS-30 (SEQ ID NO: 20). (25C) Schematic of Exo III-mediated digestion of non-target-bound (left) and target-bound (right) DIS-37. Experimental conditions: [DIS-37]: 1 μM, [MgCl$_2$]: 25 mM, [BSA]: 1×, [DIS]: 500 μM, [Exo III]: 0.013 U/μL.

FIGS. 26A-26D show the characterization of target-binding affinity of DIS-binding aptamers using ITC. Top panels present raw data showing the heat generated from each titration of DIS for (26A) DIS-34, (26B) DIS-37, (26C) DIS-33 and (26D) DIS-30. Bottom panels show the integrated heat of each titration after correcting for dilution heat of the titrant.

Figures 27A, 27B:
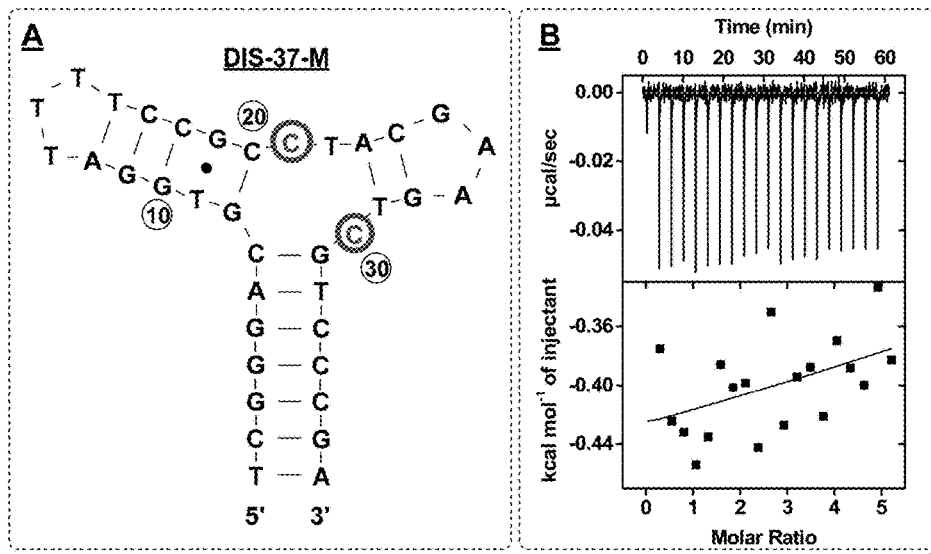

FIGS. 27A-27B show aptamer mutant DIS-37-M (SEQ ID NO: 21) and its binding affinity to DIS. (27A) Secondary structure of folded DIS-37-M. Mutated nucleotides are marked in red. (28B) Characterization of DIS binding affinity of DIS-37-M using ITC. Top panels present raw data showing the heat generated from each titration of DIS for DIS-37-M. Bottom panels show the integrated heat of each titration after correcting for dilution heat of the titrant.

Figures 28A, 28B:
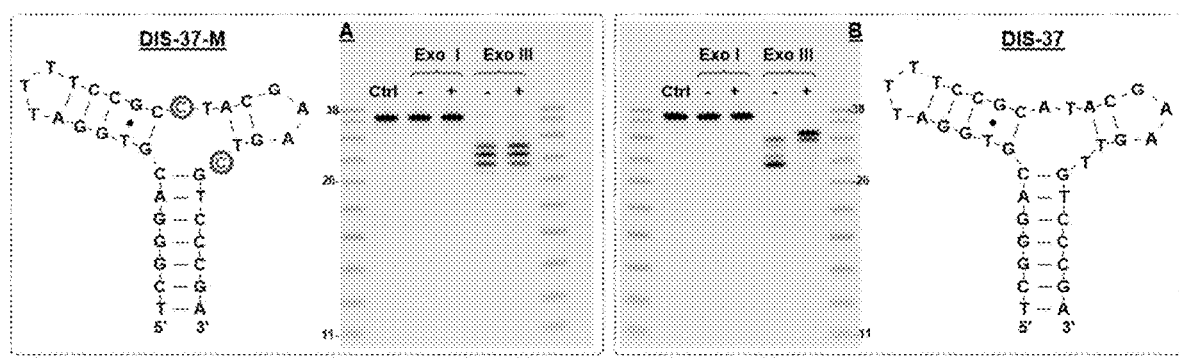

FIGS. 28A-28B show PAGE analysis of exonuclease-treated DIS-37 (SEQ ID NO: 20) and DIS-37-M (SEQ ID NO: 21) after 15 minutes of reaction in the absence and presence of DIS. Secondary structure of (28A) DIS-37-M and (28B) DIS-37 and PAGE analysis of their digestion products generated by Exo I or Exo III. Mutated nucleotides marked in red. Experimental conditions: [aptamer]: 1 µM, [MgCl$_2$]: 25 mM, [DIS]: 500 µM, [Exo III]: 0.013 U/µL, [Exo I]: 0.15 U/µL.

Figures 29A, 29B:
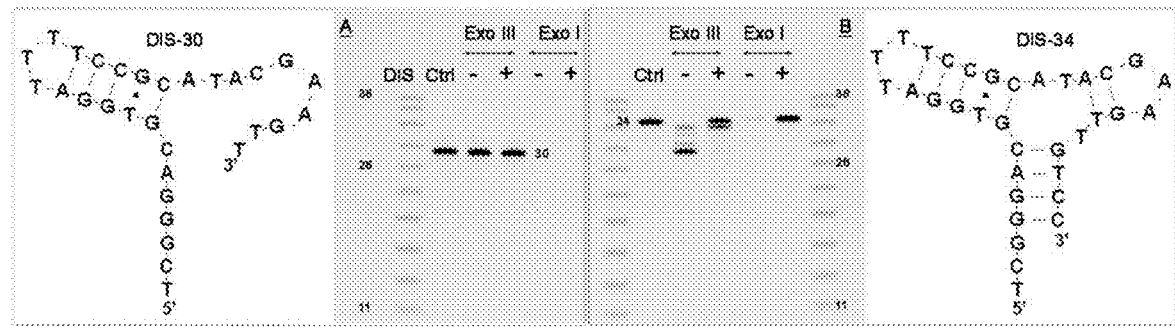

FIGS. 29A-29B show PAGE analysis of exonuclease-treated DIS-30 (SEQ ID NO: 20) and DIS-34 (SEQ ID NO: 18) after 15 minutes of digestion in the absence and presence of DIS. Secondary structure and PAGE analysis of exonuclease digestion products of (29A) DIS-30 and (29B) DIS-34. Experimental conditions: [aptamer]: 1 µM, [MgCl$_2$]: 25 mM, [BSA]: 1×, [DIS]: 500 µM, [Exo III]: 0.013 U/µL, [Exo I]: 0.15 U/µL.

Figures 30A, 30B, 30C:
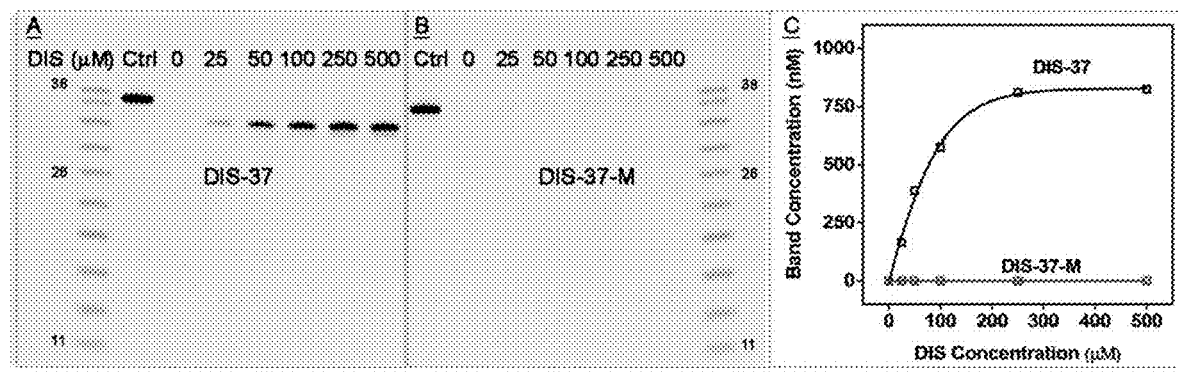

FIGS. 30A-30C show the target-concentration-dependence of exonuclease digestion of DIS-37 and digestion of its mutant (DIS-37-M) at increasing concentrations of DIS after 15 minutes. The aptamers were digested with a mixture of Exo III and Exo I and PAGE analysis was used to characterize the digestion products of (30A) DIS-37 and (30B) DIS-37-M. (30C) Calibration curve of the calculated concentration of the remaining products versus DIS concentration. The intensity of the DNA ladder was used to calculate product concentrations. Experimental conditions: [aptamer]: 1 µM, [MgCl$_2$]: 25 mM, [BSA]: 1×, [Exo III]: 0.013 U/µL and [Exo I]: 0.15 U/µL.

FIGS. 31A-31C show the DIS detection using the label-free, aptamer-based exonuclease-inhibition fluorescence assay. (31A) Scheme of the DIS-37-based, exonuclease-inhibition fluorescence assay using SYBR Gold as a signal reporter. (31B) Fluorescence spectra of SYBR Gold for exonuclease-mixture treated (red line) and untreated (black line) DIS-37 with or without 250 µM DIS. (31C) Performance of the fluorescence assay. (Left) Fluorescence spectra generated at various DIS concentrations. (Middle) A calibration curve derived from the fluorescence spectra. (Right) The linear range of the assay. Error bars represent standard deviation of three measurements.

FIG. 32 shows the linear concentration range of DIS obtained in buffer and 50% urine using the aptamer-based dual-exonuclease inhibition fluorescence assay using SYBR Gold as a signal reporter. The fluorescence intensity recorded at 545 nm was used to calculate signal gain using the equation $(F-F_0)/F_0$ where F and $F_0$ represent fluorescence intensity in the presence and absence of target, respectively. Error bars represent standard deviation of three measurements.

Figures 33A, 33B, 33C:
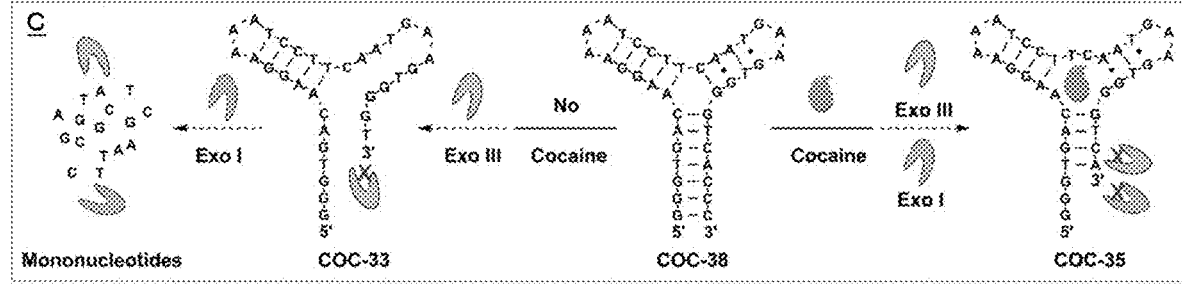

FIGS. 33A-33C show PAGE analysis of exonuclease digestion of a cocaine-binding aptamer and its mutant after 25 minutes, with or without cocaine. Secondary structure of (33A) COC-38 (SEQ ID NO: 22) and (33B) COC-38-M (SEQ ID NO: 25) and PAGE analysis of their digestion products generated by Exo III, Exo I, or a mixture of both. Mutated nucleotides are marked in red. (33C) Schematic of dual-exonuclease-mediated COC-38 digestion in the absence (left) and presence (right) of cocaine, arriving at COC-33 (SEQ ID NO: 24) and COC-35 (SEQ ID NO: 23), Experimental conditions: [aptamer]: 1 µM, [NaCl]: 100 mM, [MgCl$_2$]: 1 mM, [Cocaine]: 500 µM, [Exo III]: 0.04 U/µL, [Exo I]: 0.09 U/µL.

FIGS. 34A-34D show the characterization of target-binding affinity of cocaine-binding aptamers and a mutant using ITC. Top panels present raw data showing the heat generated from each titration of cocaine for (34A) COC-35, (34B) COC-38, (34C) COC-33 and (34D) COC-38-M. Bottom panels show the integrated heat of each titration after correcting for dilution heat of the titrant.

Figures 35A, 35B, 35C:
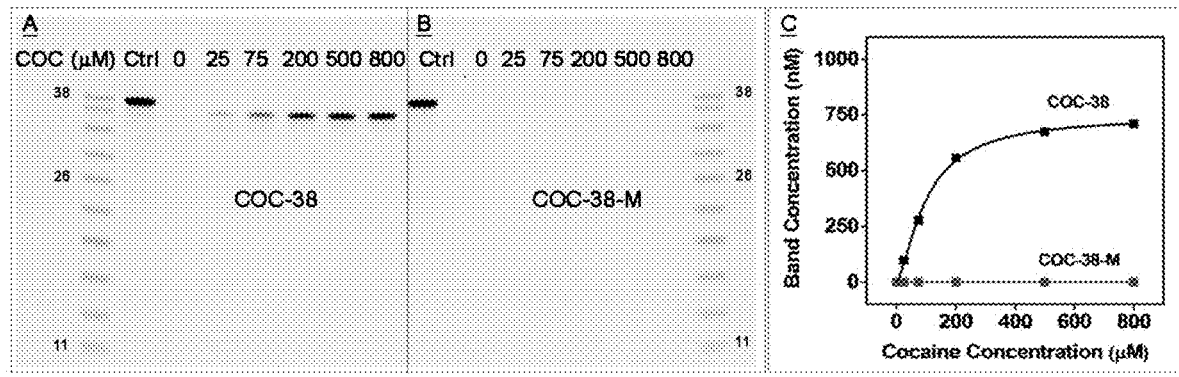

FIGS. 35A-35C show the target-concentration-dependent inhibition of dual-exonuclease-mediated digestion of a cocaine-binding aptamer and digestion of its mutant after 25 min of reaction. PAGE analysis of digestion products at increasing concentrations of cocaine for (35A) COC-38 and (35B) COC-38-M. (35C) Calibration curve of the calculated concentration of the remaining digestion product versus cocaine concentration for COC-38 and COC-38-M. The intensity of the DNA ladder was used to calculate product concentrations. Experimental conditions: [aptamer]: 1 µM, [NaCl]: 100 mM, [MgCl$_2$]: 1 mM, [Exo III]: 0.04 U/µL and [Exo I]: 0.09 U/µL.

Figures 36A, 36B, 36C:
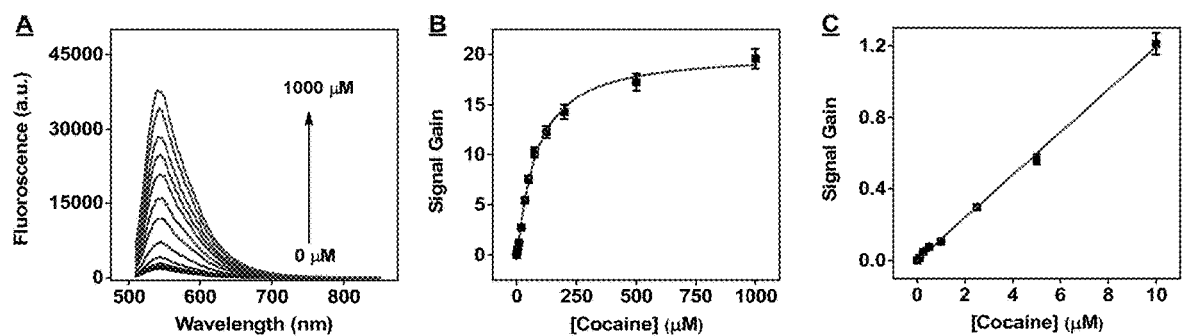

FIGS. 36A-36C show the cocaine detection using a label-free, aptamer-based dual-exonuclease inhibition fluorescence assay using SYBR Gold as a signal reporter. (36A) Fluorescence spectra of cocaine detection using the label-free, COC-38-based dual-exonuclease inhibition fluorescence assay. From bottom to top, curves depict fluorescence spectra in the presence of 0, 0.1, 0.25, 0.5, 1, 2.5, 5, 10, 20, 35, 50, 75, 125, 200, 500, or 1000 M cocaine. (36B) Calibration curve of the assay. Signal gain was calculated using the equation $(F-F_0)/F_0$ where F and $F_0$ represent fluorescence intensity at 545 nm in the presence and absence of target, respectively. (36C) Linear range from 0-10 µM ($R^2=0.9991$). Error bars represent standard deviation of three measurements.

FIG. 37 shows the linear concentration range of cocaine obtained in buffer and 10% saliva using the aptamer-based dual-exonuclease inhibition fluorescence assay using SYBR Gold as a signal reporter. The fluorescence intensity recorded at 545 nm was used to calculate signal gain using the equation $(F-F_0)/F_0$ where F and $F_0$ represent fluorescence intensity in the presence and absence of target, respectively. Error bars represent standard deviation of three measurements.

FIGS. 38A-38C show PAGE analysis of exonuclease digestion of an ATP-binding aptamer and its mutant after 20 minutes, with or without ATP. Secondary structure of (38A) ATP-33 (SEQ ID NO: 10) and (38B) ATP-33-M (SEQ ID NO: 14) and PAGE analysis of their digestion products generated by Exo III, Exo I, or a mixture of both. Mutated nucleotides are marked in red. (38C) Schematic of dual-exonuclease-mediated ATP-33 digestion with (right) and without (left) ATP, arriving at ATP-30 (SEQ ID NO: 11) and ATP-25 (SEQ ID NO: 12), respectively. Experimental conditions: [aptamer]: 1 µM, [MgCl$_2$]: 10 mM, [ATP]: 250 µM, [Exo III]: 0.05 U/µL, [Exo I]: 0.14 U/µL.

FIGS. 39A-39D show the characterization of target binding affinity of ATP-binding aptamers and a mutant using ITC. Top panels present raw data showing the heat generated from each titration of ATP for (39A) ATP-30, (39B) ATP-25, (39C) ATP-33 and (39D) ATP-33-M. Bottom panels show the integrated heat of each titration after correcting for dilution heat of the titrant.

Figures 40A, 40B, 40C:
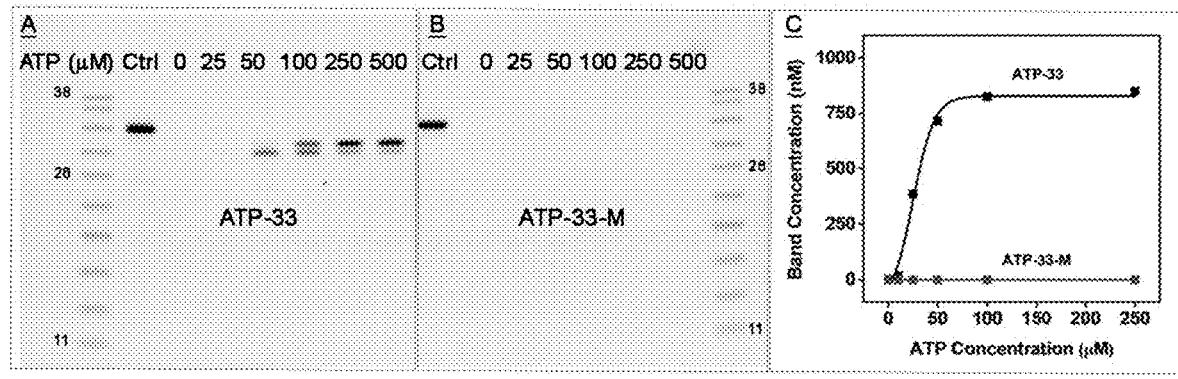

FIGS. 40A-40C show the target-concentration-dependent inhibition of dual-exonuclease-mediated digestion of an ATP-binding aptamer and digestion of its mutant after 20 min of reaction. PAGE analysis of digestion products at increasing concentrations of ATP for (40A) ATP-33 and (40B) ATP-33-M. (40C) Calibration curve of the calculated concentration of the remaining digestion products versus ATP concentration for ATP-33 and ATP-33-M. The intensity of the DNA ladder was used to calculate product concentrations. Experimental conditions: [aptamer]: 1 µM, [MgCl$_2$]: 10 mM, [Exo III]: 0.05 U/µL and [Exo I]: 0.14 U/µL.

Figures 41A, 41B, 41C:
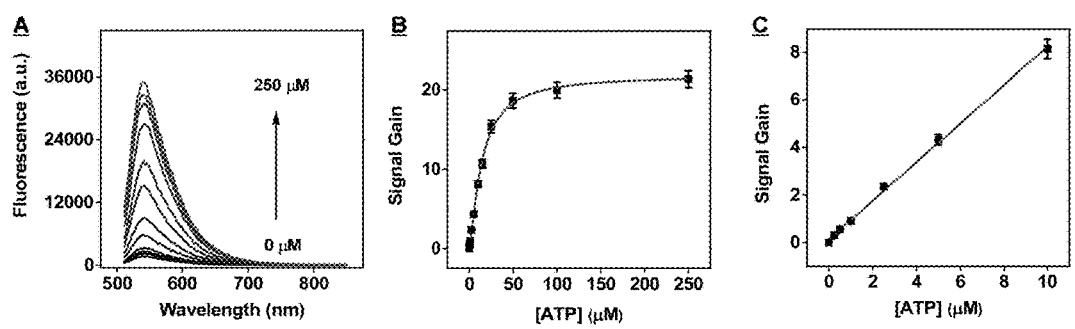

FIGS. 41A-41C show the ATP detection using the label-free, aptamer-based dual-exonuclease inhibition fluorescence assay using SYBR Gold as a signal reporter. (41A) Fluorescence spectra of cocaine detection using the label-free, ATP-33-based dual-exonuclease inhibition fluorescence assay. From bottom to top, curves depict fluorescence spectra in the presence of 0, 0.25, 0.5, 1, 2.5, 5, 10, 15, 25, 50, 100, or 250 µM ATP. (41B) Calibration curve of the assay. Signal gain was calculated using the equation $(F-F_0)/F_0$ where F and $F_0$ represent fluorescence intensity at 545 nm in the presence and absence of target, respectively. (41C) Linear range from 0-10 µM ($R^2$=0.9991). Error bars represent standard deviation of three measurements.

Figure 42:
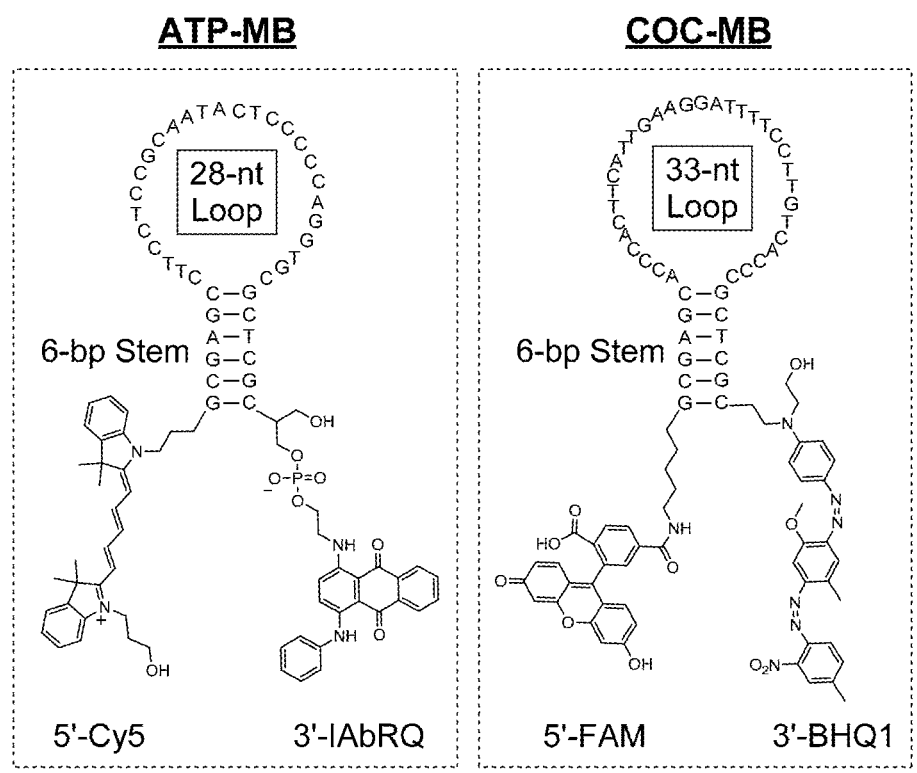

FIG. 42 shows the design of molecular beacon for ATP-binding aptamer (ATP-MB) (SEQ ID NO: 16) and cocaine-binding aptamer (COC-MB)(SEQ ID NO: 26).

Figure 43:
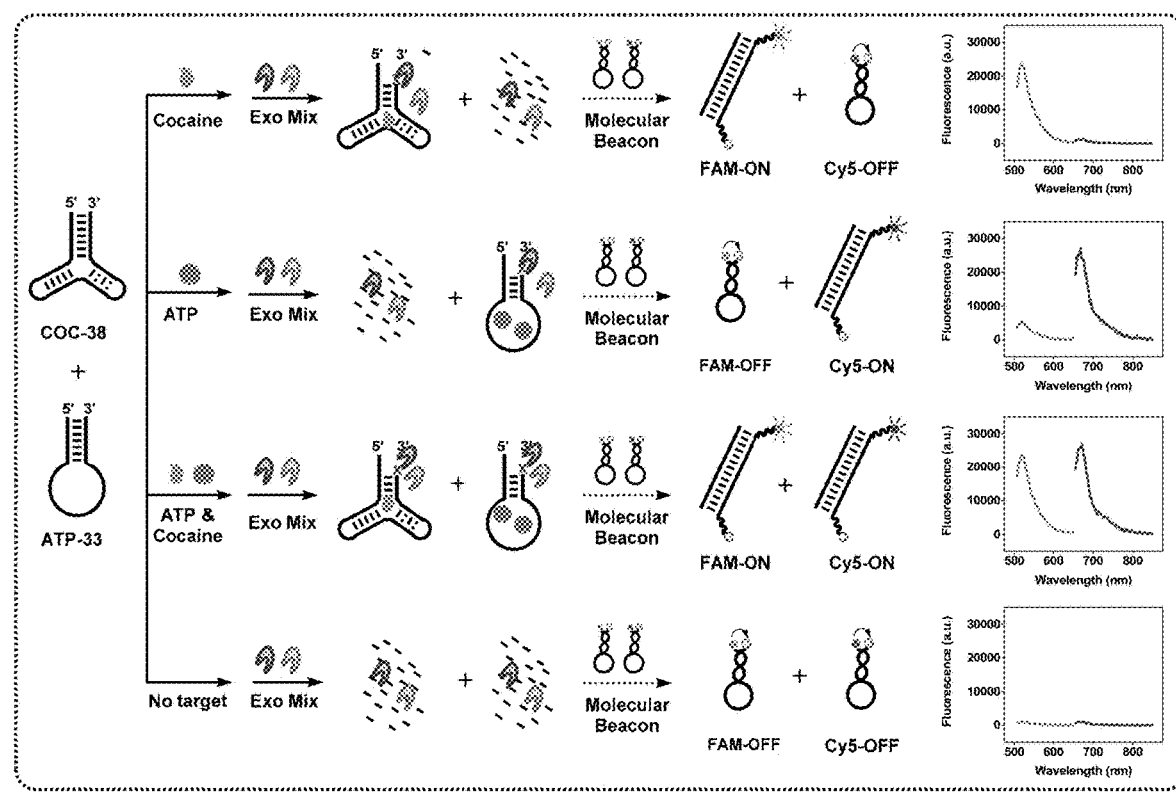

FIG. 43 shows the scheme of molecular beacon based multiplex detection for in the absence of target, cocaine alone, ATP alone, or both targets together.

FIG. 44 shows the fluorescence spectra of COC-MB (green, excitation 495 nm) and ATP-MB (red, excitation 645 nm) for exonuclease-mixture treated samples with no, either or both ATP and cocaine at the concentrations of 0, 25 or 100 µM.

Figure 45C:
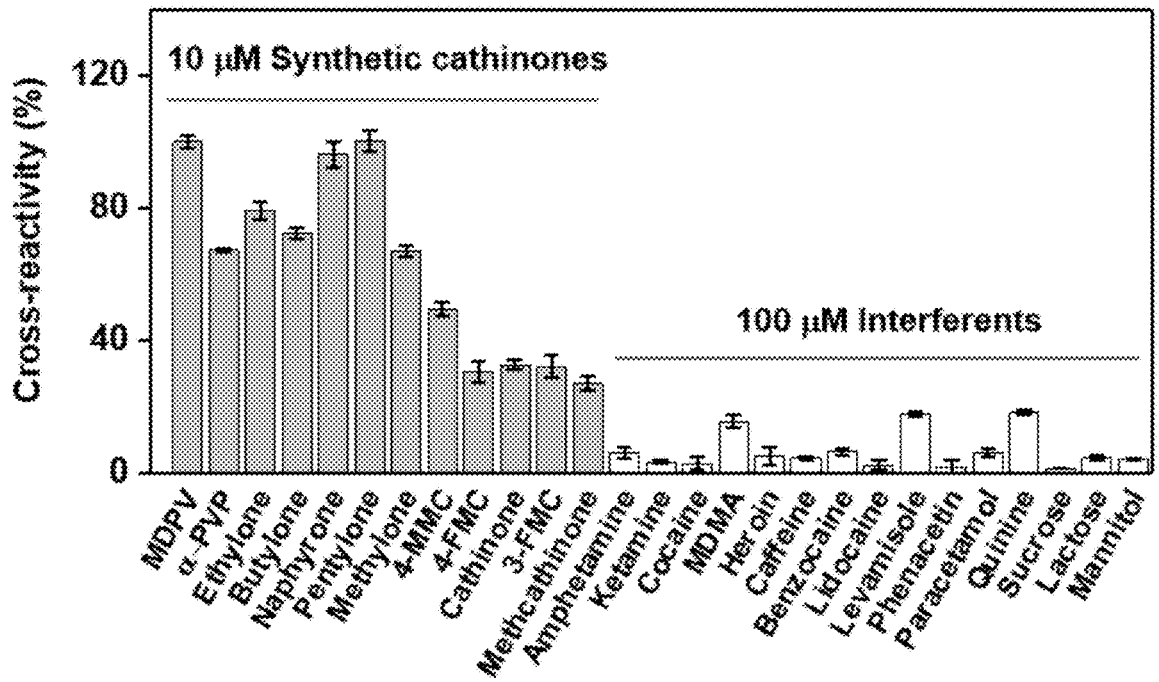

FIGS. 45A-45C show performance of an E-AB sensor modified with SCA2.1-34-MB alone. (45A) Squarewave voltammetry spectra collected at various concentrations of MDPV. (45B) Calibration curve derived from squarewave voltammetry spectra. (45C) Sensor cross-reactivity for 12 synthetic cathinones (gray) at a concentration of 10 µM and 15 interferents (white) at a concentration of 100 µM. Cross-reactivity is calculated relative to the signal gain produced by 10 µM MDPV. Error bars represent the standard deviation of measurements from three different E-AB sensors.

Figure 46A:
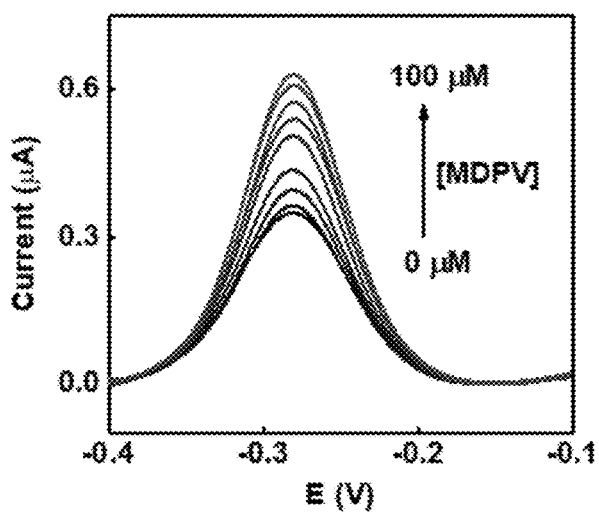
Figure 46B:
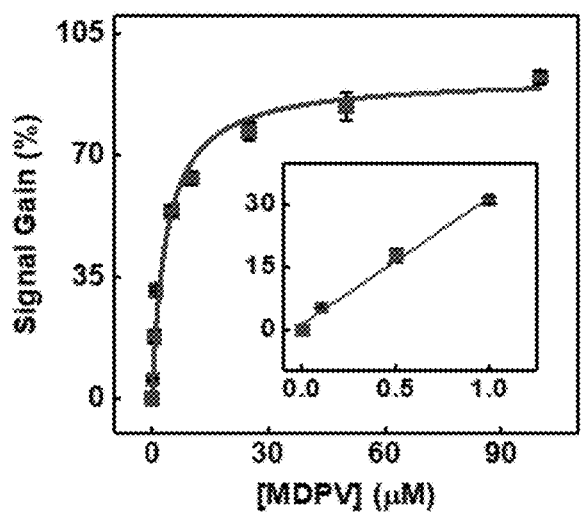
Figure 46C:
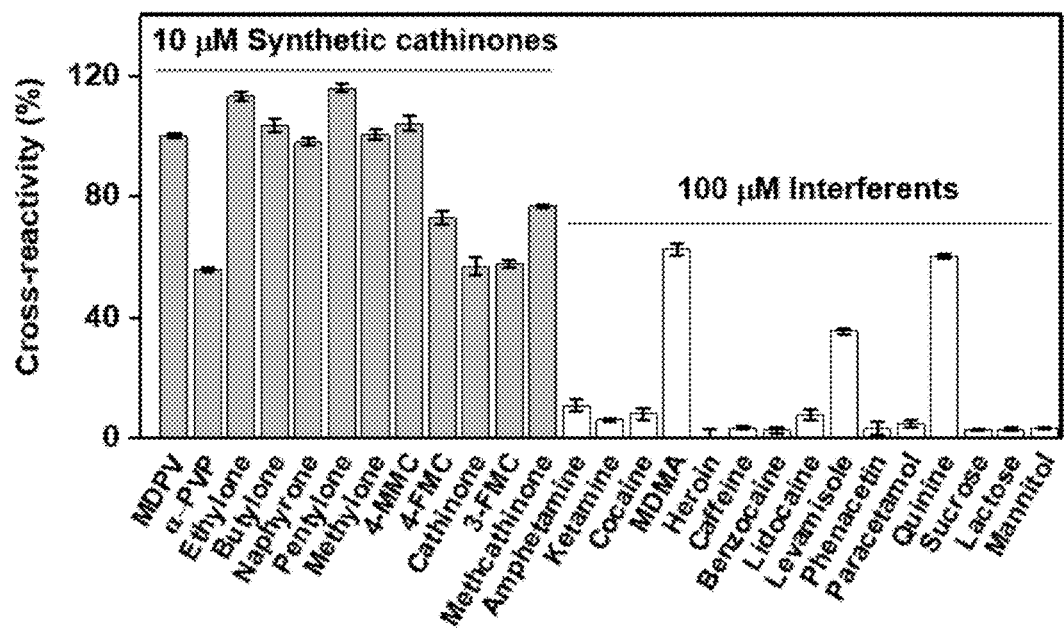

FIGS. 46A-46C show performance of an E-AB sensor modified with SCA1.1-34-MB alone. (46A) Squarewave voltammetry spectra collected at various concentrations of MDPV. (46B) Calibration curve derived from squarewave voltammetry spectra. (46C) Sensor cross-reactivity for 12 synthetic cathinones (gray) at a concentration of 10 µM and 15 interferents (white) at a concentration of 100 µM. Cross-reactivity is calculated relative to the signal gain produced by 10 µM MDPV. Error bars represent the standard deviation of measurements from three different E-AB sensors.

Figure 47A:
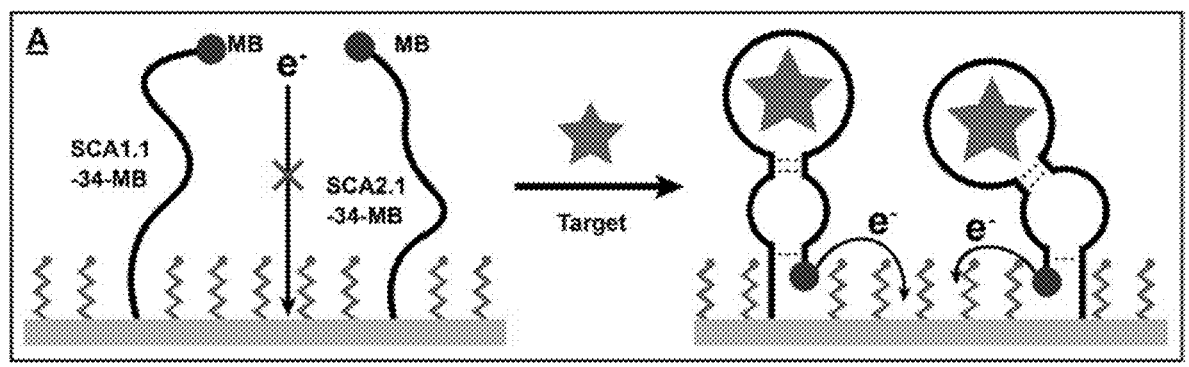
Figure 47B:
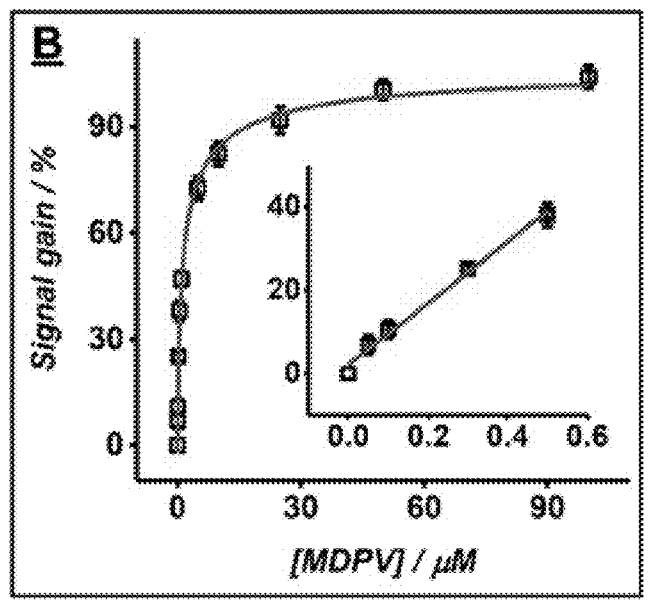
Figure 47C:
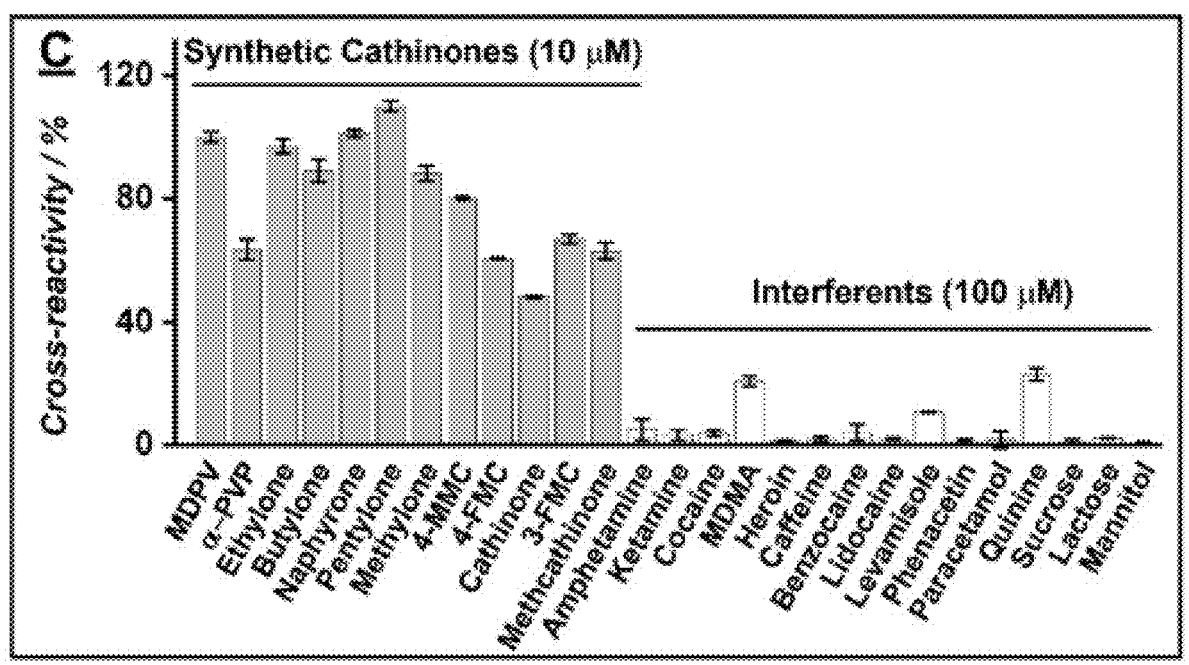

FIGS. 47A-47C show dual-aptamer-based E-AB sensor. (47A) Schematic of the assay. Aptamers are initially unfolded in the absence of target (left), situating the MB tag far from the electrode and producing minimal current. Target binding causes the aptamers to fold, resulting in enhanced charge transfer and an increase in current. (47B) Calibration curve of MDPV obtained via squarewave voltammetry. (47C) The dual-aptamer sensor shows high cross-reactivity for 12 synthetic cathinones at a concentration of 10 µM and low cross-reactivity for 15 interferents at a concentration of 100 µM.

Figure 48:
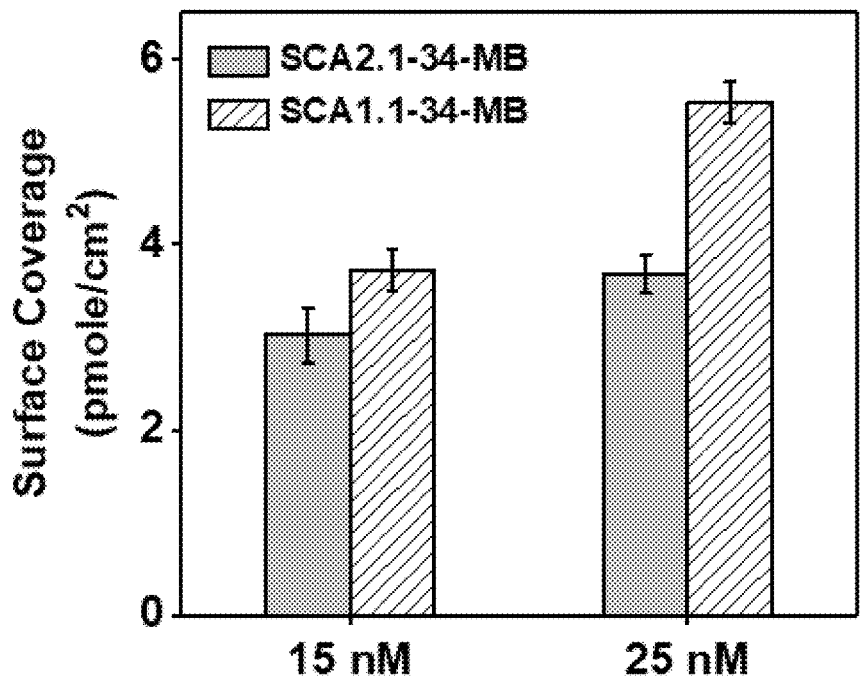

FIG. 48 shows comparison of surface coverages of electrodes modified with SCA2.1-34-MB or SCA1.1-34-MB alone at concentrations of 15 nM and 25 nM aptamer. Error bars represent the standard deviation of measurements from three different E-AB sensors.

Figure 49:
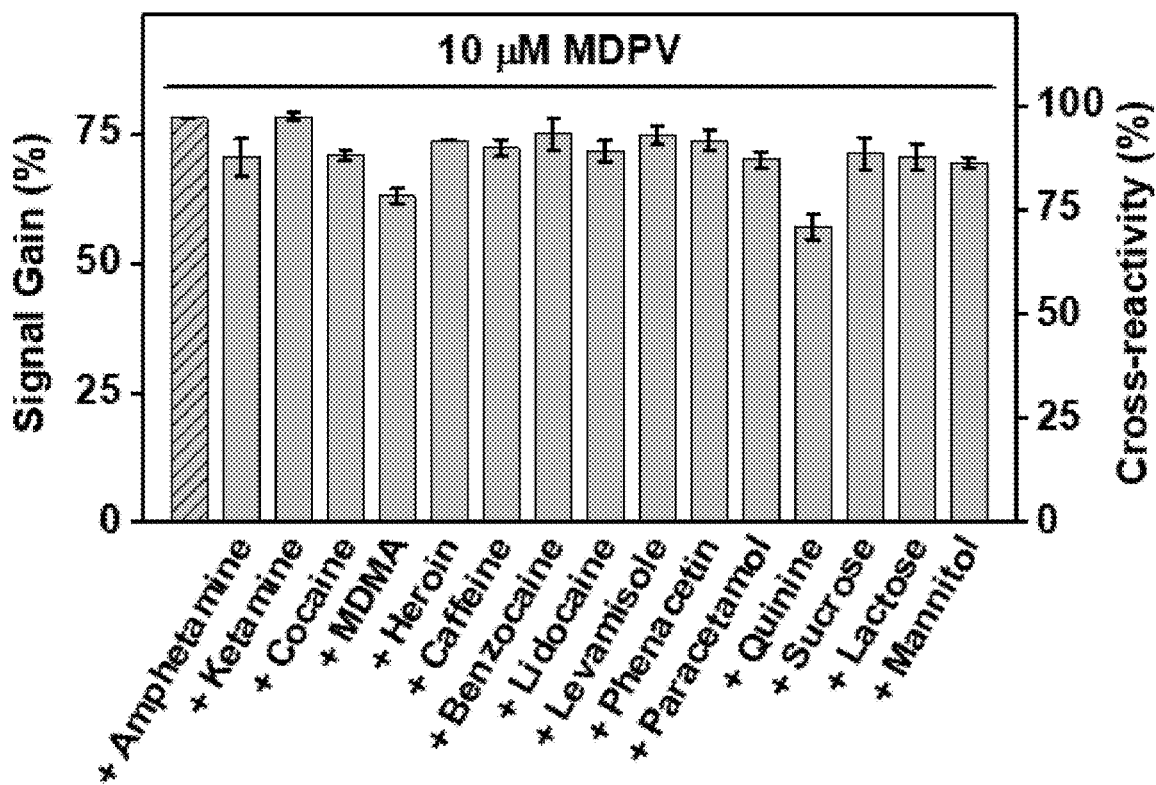

FIG. 49 shows signal gain and cross-reactivity from binary mixtures of 10 µM MDPV and 15 different interferents at a concentration of 100 µM using the dual-aptamer-modified E-AB sensor.

BRIEF DESCRIPTION OF SEQUENCES

SEQ ID NOs: 1-3 are DNA sequences of cocaine binding aptamers contemplated for use according to the subject invention.

SEQ ID NOs: 4-9 are DNA sequences of aptamers contemplated for use according to the subject invention.

SEQ ID NOs: 10-11 are DNA sequences of ATP binding aptamers contemplated for use according to the subject invention.

SEQ ID NOs: 12-16 are DNA sequences of aptamers contemplated for use according to the subject invention.

SEQ ID NOs: 17-19 are DNA sequences of DIS binding aptamers contemplated for use according to the subject invention.

SEQ ID NOs: 20-21 are DNA sequences of aptamers contemplated for use according to the subject invention.

SEQ ID NOs: 22-23 are DNA sequences of Cocaine binding aptamers contemplated for use according to the subject invention.

SEQ ID NOs: 24-26 are DNA sequences of aptamers contemplated for use according to the subject invention.

SEQ ID NOs: 27-34 are DNA sequences contained in the ladder contemplated for use according to the subject invention.

SEQ ID Nos: 35-40 are sequences of DNA aptamers contemplated for use according to the subject invention.

DETAILED DESCRIPTION OF THE INVENTION

The subject invention provides methods, assays, and products for detecting small molecules in a complex sample, in particular, in both clinical and field settings. In one embodiment, the method comprises providing a sample, contacting the sample with an aptamer-based sensor selective for the small-molecule target, and detecting the small-molecule target in the sample.

In one embodiment, the detection of the small-molecule target comprises measuring a signal generated upon contacting the sample with the aptamer-based sensor. In another embodiment, the method further comprises determining the concentration of the small-molecule target in the sample.

In one embodiment, the sample is a biological sample of a subject. In specific embodiments, the biological sample is selected from blood, plasma, urine, tears, and saliva. The subject may be any animal or human, preferably, a human. The subject may also be any animal including, but not limited to, non-human primates, rodents, dogs, cats, horses, cattle, pigs, sheep, goats, chickens, guinea pigs, hamsters and the like.

In one embodiment, the sample is an environmental sample, for example, water, soil, air, or plant sample. In another embodiment, the sample is a seized drug sample, for instance, a street drug sample seized by law enforcement or government officials.

Small Molecules

The term "target," "small molecule," or "small-molecule target," as used herein, includes any molecule capable of being detected using an aptamer technique. In one embodiment, the small molecule has a molecular weight less than 1000 Daltons, less than 900 Daltons, less than 800 Daltons, less than 700 Daltons, less than 600 Daltons, less than 500 Daltons, less than 400 Daltons, less than 300 Daltons, or less than 200 Daltons.

In one embodiment, the small-molecule target may be an amino acid, an amino acid-related molecule, a peptide, a steroid, a lipid, a sugar, a carbohydrate, a biomarker, a drug molecule, a drug metabolite, a coenzyme, a nucleotide (nt), a nucleotide-related molecule, a pyridine nucleotide, a cyclic nucleotide, or a cyclic dinucleotide. In other embodiments, the small-molecule target may be an infective agent, antigen, toxin, disease biomarker, or a specific metal ion.

In one embodiment, the small molecule is a steroid hormone. In a specific embodiment, the steroid hormone is dehydroisoandrosterone-3-sulfate (DIS).

In one embodiment, the small molecule is a drug molecule. In specific embodiments, the drug molecule is cocaine or a cocaine derivative. The cocaine derivative may or may not have the core structure of cocaine. Exemplary cocaine derivatives include, but are not limited to, 4-fluorococaine, 2-hydroxycocaine, 3-(p-fluorobenzoyloxy)tropane (pFBT), procaine, and dimethocaine.

In one embodiment, the small molecule comprises a nucleobase, such as adenine (A), cytosine (C), guanine (G), thymine (T), and uracil (U). The small molecule may also comprise a nucleoside including ribonucleoside and deoxyribonucleoside. Examples include, but are not limited to, adenosine triphosphate (ATP), adenosine diphosphate (ADP), adenosine monophosphate (AMP), cyclic adenosine monophosphate (cAMP), guanosine triphosphate (GTP), guanosine diphosphate (GDP), guanosine monophosphate (GMP), and cyclic guanosine monophosphate (cGMP). In a specific embodiment, the small molecule is ATP.

In one embodiment, the small molecule is a drug molecule. In a further embodiment, the drug molecule is a cathinone, a cathinone derivative, or synthetic cathinone, such as a ring-substituted cathinone derivative or synthetic cathinone.

In one embodiment, the synthetic cathinone has a general structure of formula (I)

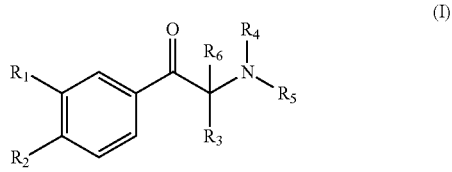

wherein $R_1$ $R_2$, $R_3$, $R_4$, $R_5$, and $R_6$ are each independently selected from the group consisting of hydrogen, alkyl, substituted alkyl, aryl, substituted aryl, benzyl, heteroaryl, substituted heteroaryl, cycloalkyl, substituted cycloalkyl, cycloalkenyl, substituted cycloalkenyl, heterocycloalkyl, alkenyl, alkynyl, alkoxy, thiol, haloalkyl, acyl, halogen, amino, alkylamino, hydroxyl, hydroxylalkyl, and —COOH.

In one embodiment, $R_1$ and $R_2$, are each independently selected from the group consisting of hydrogen, alkyl, aryl, heteroaryl, cycloalkyl, cycloalkenyl, heterocycloalkyl, alkenyl, alkynyl, haloalkyl, acyl, alkoxy, halogen, and hydroxylalkyl; $R_3$ is hydrogen or alkyl. $R_4$, and $R_5$ are each independently selected from the group consisting of hydrogen, alkyl, aryl, heteroaryl, cycloalkyl, cycloalkenyl, heterocycloalkyl, alkenyl, alkynyl, haloalkyl, acyl, halogen, and hydroxylalkyl; and $R_6$ is hydrogen or alkyl.

In a further embodiment, $R_1$ and $R_2$ are independently halogen, such as fluorine, chlorine, bromine or iodine.

In some embodiments, $R_1$ and $R_2$, taken together with the carbon atoms to which they are attached, form a substituted or unsubstituted 5- or 6-membered homocyclic or heterocyclic ring. For example, $R_1$ and $R_2$ may form a methylenedioxy group or aromatic ring such as benzene.

In other embodiments, $R_4$ and $R_5$, taken together with the nitrogen atom to which they are attached, form a substituted or unsubstituted 5- or 6-membered heterocyclic ring. For example, $R_4$ and $R_5$ may form a pyrrolidino group.

As used herein, "alkyl" means linear saturated monovalent radicals of at least one carbon atom or a branched saturated monovalent of at least three carbon atoms. It may include hydrocarbon radicals of at least one carbon atom, which may be linear. Examples include, but are not limited to, methyl, ethyl, propyl, 2-propyl, n-butyl, iso-butyl, tert-butyl, pentyl, hexyl, and the like.

As used herein, "acyl" means a radical —C(O)R where R includes, but is not limited to, hydrogen, alkyl or cycloalkyl, and heterocycloalkyl. Examples include, but are not limited to, formyl, acetyl, ethylcarbonyl, and the like. An aryl group may be substituted or unsubstituted.

As used herein, "alkylamino" means a radical —NHR or —NR2 where each R is, independently, an alkyl group. Examples include, but are not limited to, methylamino, (1-methylethyl)amino, dimethyl amino, methylethylamino, di(1-methylethyl)amino, and the like. An alkylamino may be substituted or unsubstituted.

As used herein, "hydroxyalkyl" means an alkyl radical substituted with one or more hydroxy groups. Representative examples include, but are not limited to, hydroxymethyl, 2-hydroxyethyl; 2-hydroxypropyl; 3-hydroxypropyl; 1-(hydroxymethyl)-2-methylpropyl; 2-hydroxybutyl; 3-hydroxybutyl; 4-hydroxybutyl; 2,3-dihydroxypropyl; 2-hydroxy-1-hydroxymethylethyl; 2,3-dihydroxybutyl; 3,4-dihydroxybutyl and 2-(hydroxymethyl)-3-hydroxy-propyl; preferably 2-hydroxyethyl; 2,3-dihydroxypropyl and 1-(hydroxymethyl) 2-hydroxyethyl. A hydroxyalkyl may be substituted or unsubstituted.

As used herein, "alkenyl" refers to a straight or branched hydrocarbon chain containing one or more double bonds. The alkenyl group may have 2 to 9 carbon atoms, although the present definition also covers the occurrence of the term "alkenyl" where no numerical range is designated. The alkenyl group may also be a medium size alkenyl having 2 to 9 carbon atoms. The alkenyl group could also be a lower alkenyl having 2 to 4 carbon atoms. The alkenyl group may be designated as "$C_{2-4}$ alkenyl" or similar designations. By way of example only, "$C_{2-4}$ alkenyl" indicates that there are two to four carbon atoms in the alkenyl chain, i.e., the alkenyl chain is selected from ethenyl; propen-1-yl; propen-2-yl; propen-3-yl; buten-1-yl; buten-2-yl; buten-3-yl; buten-4-yl; 1-methyl-propen-1-yl; 2-methyl-propen-1-yl; 1-ethyl-ethen-1-yl; 2-methyl-propen-3-yl; buta-1,3-dienyl; buta-1,2,-dienyl and buta-1,2-dien-4-yl. Typical alkenyl groups include, but are in no way limited to, ethenyl, propenyl, butenyl, pentenyl, and hexenyl, and the like.

As used herein, "alkynyl" refers to a straight or branched hydrocarbon chain comprising one or more triple bonds. The alkynyl group may have 2 to 9 carbon atoms, although the present definition also covers the occurrence of the term "alkynyl" where no numerical range is designated. The alkynyl group may also be a medium size alkynyl having 2 to 9 carbon atoms. The alkynyl group could also be a lower alkynyl having 2 to 4 carbon atoms. The alkynyl group may be designated as "$C_{2-4}$ alkynyl" or similar designations. By way of example only, "$C_{2-4}$ alkynyl" indicates that there are two to four carbon atoms in the alkynyl chain, e.g., the alkynyl chain is selected from ethynyl, propyn-1-yl, propyn-2-yl, butyn-1-yl, butyn-3-yl, butyn-4-yl, and 2-butynyl. Typical alkynyl groups include, but are in no way limited to, ethynyl, propynyl, butynyl, pentynyl, and hexynyl, and the like.

As used herein, "cycloalkyl" means a fully saturated carbocyclyl ring or ring system. Examples include, but are not limited to, cyclopropyl, cyclobutyl, cyclopentyl, and cyclohexyl.

As used herein, "aryl" refers to a carbocyclic (all carbon) monocyclic or multicyclic aromatic ring system (including fused ring systems where two carbocyclic rings share a chemical bond). The number of carbon atoms in an aryl group can vary. For example, the aryl group can be a $C_6$-$C_{14}$ aryl group, a $C_6$-$C_{10}$ aryl group, or a $C_6$ aryl group. Examples of aryl groups include, but are not limited to, phenyl, benzyl, α-naphthyl, β-naphthyl, biphenyl, anthryl, tetrahydronaphthyl, fluorenyl, indanyl, biphenylenyl, and acenaphthenyl. Preferred aryl groups are phenyl and naphthyl.

As used herein, "heteroaryl" refers to an aromatic ring or ring system (i.e., two or more fused rings that share two adjacent atoms) that comprise(s) one or more heteroatoms, that is, an element other than carbon, including but not limited to, nitrogen, oxygen and sulfur, in the ring backbone. When the heteroaryl is a ring system, every ring in the system is aromatic. The heteroaryl group may have 5-18 ring members (i.e., the number of atoms making up the ring backbone, including carbon atoms and heteroatoms), although the present definition also covers the occurrence of the term "heteroaryl" where no numerical range is designated. Examples of heteroaryl rings include, but are not limited to, furyl, thienyl, phthalazinyl, pyrrolyl, oxazolyl, thiazolyl, imidazolyl, pyrazolyl, isoxazolyl, isothiazolyl, triazolyl, thiadiazolyl, pyridinyl, pyridazinyl, pyrimidinyl, pyrazinyl, triazinyl, quinolinyl, isoquinlinyl, benzimidazolyl, benzoxazolyl, benzothiazolyl, indolyl, isoindolyl, and benzothienyl.

As used herein, "haloalkyl" refers to an alkyl group in which one or more of the hydrogen atoms is replaced by a halogen (e.g., mono-haloalkyl, di-haloalkyl and tri-haloalkyl). Such groups include but are not limited to, chloromethyl, fluoromethyl, difluoromethyl, trifluoromethyl and 1-chloro-2-fluoromethyl, 2-fluoroisobutyl. A haloalkyl may be substituted or unsubstituted.

As used herein, a "substituted" group may be substituted with one or more group(s) individually and independently selected from alkyl, alkenyl, alkynyl, cycloalkyl, cycloalkenyl, cycloalkynyl, benzyl, substituted benzyl, aryl, heteroaryl, heteroalicyclyl, aralkyl, heteroaralkyl, (heteroalicyclyl)alkyl, hydroxy, protected hydroxyl, alkoxy, aryloxy, acyl, mercapto, alkylthio, arylthio, cyano, halogen, thiol, thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, nitro, silyl, sulfenyl, sulfinyl, sulfonyl, haloalkyl, haloalkoxy, trihalomethanesulfonyl, trihalomethanesulfonamido, an amino, a mono-substituted amino group and a di-substituted amino group, and protected derivatives thereof.

As used herein, "halogen" refers to an atom of fluorine, chlorine, bromine or iodine.

As used herein, "homocyclic ring" refers to cycloalkyl or aryl.

As used herein, "heterocyclic ring" refers to a ring, which may contain 1 to 4 heteroatoms selected from among nitrogen, oxygen, sulfur and other atoms in addition to carbon atoms.

Exemplary cathinones or synthetic cathinones include, but are not limited to, 3, 4-methylenedioxypyrovalerone (MDPV); naphyrone; methylone; ethylone; butylone; pentylone; mephedrone; mexedrone; buphedrone; pentedrone; hexedrone; heptedrone; α-pyrrolidinopropiophenone (α-PPP); 4'-methyl-α-pyrrolidinopropiophenone (M-α-PPP); 3',4'-methylenedioxy-α-pyrrolidinopropiophenone (MDPPP); 1-phenyl-2-(1-pyrrolidinyl)-1-pentanone (α-PVP); α-pyrrolidinohexiophenone (α-PHP); α-pyrrolidinoheptiophenone (α-PHpP, PV8); diethylpropion; pyrovalerone; dimethylcathinone; diethylcathinone; methcathinone; ethcathinone; 3-methylmethcathinone (3-MMC); 4-methylethcathinone (4-MEC); 3-chloromethcathinone (3-CMC); 4-chloromethcathinone (4-CMC); n-ethyl-nor-pentedrone (NEP); n-ethyl-nor-hexedrone (Hexen); n-ethyl-nor-heptedrone; 4-ethylpentedrone; 4-methyl-NEP; and n-ethyl-nor-pentylone.

In a specific embodiment, the synthetic cathinone is MDPV, naphyrone, methylone, pentylone, or mephedrone.

Aptamers

The subject invention provides aptamer-based sensors for detecting small-molecule targets. In one embodiment, the aptamer-based sensor comprises a fully folded aptamer having structure-switching functionality upon digestion by an exonuclease. In one embodiment, the aptamer-based sensor comprises an aptamer selective for a small-molecule target, wherein the aptamer is digested by an exonuclease, e.g., Exo III, resulting in a truncated aptamer having structure-switching functionality that allows the aptamer to undergo target-induced conformational changes.

In another embodiment, the aptamer-based sensor comprises an exonuclease-truncated aptamer having the structure-switching functionality, wherein the exonuclease-truncated aptamer is a digestion product of a fully-folded parent aptamer, the exonuclease is Exo III, and the fully-folded parent aptamer does not have the structure-switching functionality.

In one embodiment, the aptamer-based sensor comprises an aptamer, wherein the aptamer comprises a three-way junction (TWJ) binding domain or a hairpin structure, and the aptamer has structure-switching functionality produced by contacting a parent aptamer having a blunt-ended stem with an exonuclease.

Aptamers are nucleic acid molecules characterized by the ability to bind to a target molecule with high specificity and high affinity. Almost every aptamer identified to date is a non-naturally occurring molecule. Aptamers to a given target may be identified and/or produced by the method of systematic evolution of ligands by exponential enrichment (SELEX). In one embodiment, the aptamer according to the subject invention is isolated by SELEX for the small molecule of interest.

In one embodiment, the aptamer is an oligonucleotide, such as DNA or RNA molecules and may be single-stranded or double-stranded. In a preferred embodiment, the aptamer is a DNA aptamer.

The aptamer may be partially or fully folded to form various secondary structures (e.g., stems, loops, bulges, pseudoknots, G-quadruplexes and kissing hairpins), which in turn can form unique three-dimensional architectures able to specifically recognize their targets by exploiting a variety of interactions—such as hydrophobic and electrostatic interactions, hydrogen bonding, van der Waals forces, and π-π stacking as well as shape complementarity.

As used herein, the terms "polynucleotide," "nucleotide," "oligonucleotide," and "nucleic acid" refer to a nucleic acid comprising DNA, RNA, derivatives thereof, or combinations thereof.

In one embodiment, the aptamer according to the present invention may comprise at least 10, at least 20, at least 30, at least 40, at least 50, at least 60, at least 70, or at least 80 nucleotides. The aptamer according to the present invention, preferably, comprises 10 to 200 nucleotides, preferably 15 to 150 nucleotides, more preferably 20 to 100 nucleotides, most preferably, 30 to 60 nucleotides.

In one embodiment, the aptamer according to the present invention has a minimum length of, for example, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides. The aptamer according to the present invention may have a maximum length of, for example, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, or 150 nucleotides. The aptamer according to the present invention may have a length of, for example, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 nucleotides.

In some embodiments, the aptamers according to the subject invention have free ends. For example, the 3' and 5' ends may not be ligated to form a loop, although they may be conjugated to other molecules or otherwise modified. The aptamers may adopt a tertiary structure such as a hairpin loop.

In one embodiment, the aptamer according to the subject invention comprises at least one stems, two stems, or three stems. Preferably, the aptamer comprises three stems. Each stem may be fully or partially complementary. Each stem may comprise the same or a different number of nucleotides. Exemplary lengths of each stem may be 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides.

In one embodiment, each stem comprises the same or a different number of base pairs (bps). Each stem may have a minimum of, for example, 1, 2, 3, 4, 5, 6, 7, 8, 9, 10, 11, or 12 base pairs. Each stem may have a maximum of, for example, 13, 14, 15, 16, 17, 18, 19, 20, 21, 22, 23, 24, 25, 26, 27, 28, 29, or 30 base pairs. Each stem according to the present invention may have a number of, for example, 1, 2, 3, 4, 5, 6, 7, 8, 9, 10, 11, 12, 13, 14, or 15 base pairs. A partially complementary stem may comprise more than one wobble base pair, including, but not limited to, G-U, and T-G.

Each of the stems may independently connect to a loop at the end, forming a stem-loop structure. The aptamer may thereby comprise at least one, two, or three stem-loop structures. The stem-loop structure according to the present invention may have a minimum length of, for example, 5, 6, 7, 8, 9, 10, 11, 12, 13, 14, 15, 16, 17, 18, 19, 20, 21, 22, 23, 24, or 25 nucleotides. The stem-loop structure may have a maximum length of, for example, 40, 41, 42, 43, 44, 45, 46, 47, 48, 49, 50, 51, 52, 53, 54, 55, 56, 57, 58, 59, 60, 61, 62, 63, 64, or 65 nucleotides.

In one embodiment, the aptamer comprises at least one junction, which is formed when two or more stems meet. In certain embodiments, the junction may be a loop between two stems, or a three-way junction (TWJ). The junction in an aptamer can serve as a binding domain for a small-molecule target.

The junction may have a minimum length of, for example, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides. The junction may have a maximum length of, for example, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleotides. The junction may comprise, for example, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides.

In a specific embodiment, the aptamer comprises a TWJ-binding domain. In some embodiments, the aptamer is a monomer, dimer, trimer, or tetramer. Such aptamer can comprise one, two, three, or four TWJ-binding domains. The aptamer containing one or more TWJ-binding domain may be predominantly folded even in the absence of the target due to the multiple Watson-Crick base pairs in its stem. Such aptamer can bind to their target with micro or nano-molar affinity.

In some embodiments, the aptamer is truncated from either 3' or 5' end by nucleases, preferably, exonucleases, such as Exo I and Exo III. Exo III exhibits 3'-to-5' exonuclease activity on double-stranded DNA with low activity against single-stranded DNA whereas Exo I exhibits exonuclease activity on single-stranded DNA but not on double-stranded DNA. Exo III is sensitive to local structural changes in double-stranded DNA induced by small-molecule binding.

In the absence of target, Exo III catalyzes 3'-to-5' digestion of aptamers by the stepwise removal of mononucleotides, forming short, single-stranded products. The truncation or digestion of the aptamer by an exonuclease, e.g., Exo III, can be inhibited by the binding of a small-molecule target to the target-binding domain, for example, the TWJ-binding domain, minor-groove, and major groove of the double-stranded DNA, forming a truncated target-bound aptamer. Such truncation or digestion of an aptamer may be stopped at least 1, 2, 3, 4, 5, 6, 7, 8, 9, 10, 11, or 12 nucleotides prior to the binding site. Such truncated or digested aptamer product is at least 1, 2, 3, 4, 5, 6, 7, 8, 9, 10, 11, or 12 nucleotides shorter compared to the pre-folded aptamer before the truncation or digestion by the exonuclease(s). Thus, target-binding is crucial for Exo III (or other exonucleases) inhibition, and the concentration of the truncated digestion product increases with increasing concentrations of target. In a specific embodiment, the truncated or digested aptamer has a stem comprising a sticky end.

In the absence of the small-molecule target, the digestion of aptamer by exonuclease, e.g., Exo III, leaves a single stranded oligonucleotide product that can further be digested by a second exonuclease, e.g., Exo I. Exo I is, however, incapable of digesting the target-bound double-stranded product.

Advantageously, the resulting digestion product of the aptamer, i.e., the truncated aptamer, exhibits a target-induced structure-switching functionality that is absent in the parent aptamer, while still retaining high target-binding affinity comparable to that of the parent aptamer.

In one embodiment, the aptamer is selected from 38-GC (SEQ ID NO: 1), 38-GT (SEQ ID NO: 2), 35-GT (SEQ ID NO: 3), COC-38 (SEQ ID NO: 22), COC-35 (SEQ ID NO: 23), COC-33 (SEQ ID NO: 24), COC-MB (SEQ ID NO: 26), and sequences sharing at least 50%, 55%, 60%, 65%, 70%, 75%, 80%, 85%, 90%, 95% or 99% identity with 38-GC (SEQ ID NO: 1), 38-GT (SEQ ID NO: 2), 35-GT (SEQ ID NO: 3), COC-38 (SEQ ID NO: 22), COC-35 (SEQ ID NO: 23), COC-33 (SEQ ID NO: 24), or COC-MB (SEQ ID NO: 26).

In some embodiments, the aptamer is specific for cocaine and does not bind to various structurally similar drugs such as benzoylecgonine (BZE), and methylecgonidine (MEG) as well as structurally dissimilar interferent drugs such as nicotine (NIC), and scopolamine (SCP).

In one embodiment, the aptamer comprises a TWJ-binding domain and a stem having seven base-pairs, wherein the aptamer is fully folded in the absence of the target. In specific embodiments, the aptamer is an aptamer specific for cocaine, having 38 nucleotides. In a specific embodiment, the aptamer has a sequence of 38-GT (SEQ ID NO: 2), 38-GC (SEQ ID NO: 1) or COC-38 (SEQ ID NO: 22). For example, binding of cocaine induces a minor conformational change in 38-GC aptamer, in which the A8-T20 base-pair in stem 2 and the C21-G31 base-pair in stem 3 are disrupted to form a T20-C21 dinucleotide bulge and an A8-G31 mismatch in the TWJ junction.

In specific embodiments, part of the aptamer may remain single stranded, which can form a bulge structure. Such bulge structure may form one of the stems of the aptamer. Upon target binding, such single-stranded bulge structure forms a partially or fully complementary stem, resulting in a TWJ structure-containing aptamer, which is resistant to exonuclease, e.g., Exo III, digestion. In a preferred embodiment, the aptamer having a bulge stem is 38-GT (SEQ ID NO: 2).

In the presence of exonuclease, e.g., Exo III, the pre-folded aptamers, such as 38-GT (SEQ ID NO: 2) and 38-GC (SEQ ID NO: 1), are digested by the exonuclease and such digestion is inhibited in the presence of the small-molecule target, e.g., cocaine. Exo III digestion destabilizes the aptamer by truncating the stem 1 from the 3' end to four base-pairs prior to the target-binding site, resulting in a truncated aptamer selective for cocaine (e.g, 35-GT). Such truncated aptamer has the structure-switching functionality, which does not exist in the pre-folded parent aptamer. The structure-switching functionality enables the truncated aptamer to undergo large target-induced conformational changes. In the absence of a target, e.g., cocaine, the truncated aptamer is partially or fully unfolded while, in the presence of the target, the truncated aptamer is fully folded forming a target-aptamer complex. The structure-switching functionality is confirmed by digesting the truncated aptamers with, for example, Exo I, a single-strand DNA-specific exonuclease, in the presence and absence of target.

In one embodiment, the truncated aptamer comprises the same TWJ domain for target binding as the parent aptamer. The TWJ-binding domain comprises two adjacent A-G pairs and a dinucleotide bulge including T and C. Mutations at one or more of these nucleotides impair the target-binding ability of the parent aptamer and the truncated aptamer. In specific embodiments, the adjacent base pairs are A8-G31 and A22-G30. The dinucleotide bulge comprises T20 and C21.

In one embodiment, the aptamer is selected from ATP-33 (SEQ ID NO: 10), ATP-30 (SEQ ID NO: 11), ATP-30-FQ (SEQ ID NO: 13), ATP-SW-34 (SEQ ID NO: 15), ATP-MB (SEQ ID NO: 16) and sequences sharing at least 50%, 55%, 60%, 65%, 70%, 75%, 80%, 85%, 90%, 95% or 99% identity with ATP-33 (SEQ ID NO: 10), ATP-30 (SEQ ID NO: 11), ATP-30-FQ (SEQ ID NO: 13), ATP-SW-34 (SEQ ID NO: 15), or ATP-MB (SEQ ID NO: 16).

In one embodiment, the aptamer comprises a stem-loop/hairpin structure, wherein the stem comprises seven base pairs. The aptamer may be fully folded in the absence of the target. In a specific embodiment, the aptamer is an aptamer specific for ATP. In the presence of ATP, a first ATP molecule binds to the ATP-binding domain, inducing a minor target-induced conformational change in the aptamer, which further facilitates the binding of the second ATP molecule to the binding domain. Preferably, the ATP-binding aptamer comprises 33 nucleotides and has a sequence of ATP-33 (SEQ ID NO: 10).

In the presence of exonuclease, e.g., Exo III, the pre-folded aptamer such as ATP-33 (SEQ ID NO: 10) is digested by the exonuclease. For example, the digestion by Exo III is inhibited in the presence of ATP. Exo III digestion destabilizes the aptamer by truncating the stem from the 3' end to four base-pairs prior to the target-binding site, resulting in a 30 nucleotides digestion product (e.g., a truncated aptamer selective for ATP). Such truncated aptamer gains the structure-switching functionality, which does not exist in the pre-folded parent aptamer. The structure-switching functionality enables the truncated aptamer to undergo large target-induced conformational changes. For example, in the absence of ATP, the truncated aptamer is partially or fully unfolded. In the presence of ATP, the truncated aptamer is fully folded with ATP binding to the ATP-binding domain of the truncated aptamer. The structure-switching functionality is confirmed by digesting the truncated aptamers with, for example, Exo I, a single-strand DNA-specific exonuclease, in the presence and absence of target. In a specific embodiment, the truncated aptamer is ATP-30 (SEQ ID NO: 11).

In one embodiment, the truncated aptamer comprises the same ATP-binding domain as the parent aptamer. The ATP-binding domain comprises at least one adenine and at least one guanine. In a further embodiment, the ATP-binding domain comprises a guanine at position 12 (G12) and an adenine at position 23 (A23) of both the parent aptamer and the truncated aptamer. Mutations at one or more of these nucleotides impair the target-binding ability of the parent aptamer and the truncated aptamer to ATP.

In one embodiment, the ATP-binding domain may have a minimum length of, for example, 10, 11, 12, 13, 14, 15, 16, 17, 18, 19, 20 or 21 nucleotides. The ATP-binding domain may have a maximum length of, for example, 22, 23, 24, 25, 26, 27, 28, 29, 30, 31, 32, 33, 34, 35, 36, 37, 38, 39, 40, 41, 42, 43, 44, 45, 46, 47, 48, 49 or 50 nucleotides. The ATP-binding domain may comprise, for example, 15, 16, 17, 18, 19, 20, 21, 22, 23, 24 or 25 nucleotides.

In one embodiment, the aptamer is selected from DIS-37 (SEQ ID NO: 17), DIS-34 (SEQ ID NO: 18), DIS-33 (SEQ ID NO: 19), and sequences sharing at least 50%, 55%, 60%, 65%, 70%, 75%, 80%, 85%, 90%, 95% or 99% identity with DIS-37 (SEQ ID NO: 17), DIS-34 (SEQ ID NO: 18), or DIS-33 (SEQ ID NO: 19).

In one embodiment, the aptamer comprises a TWJ-binding domain wherein the aptamer is fully folded in the absence of a target. In a specific embodiment, the aptamer is an aptamer specific for DIS having 37 nucleotides, and has a sequence of DIS-37 (SEQ ID NO: 17). DIS-37 exists in a fully-folded state in the absence of DIS due to the seven Watson-Crick base-pairs its stem. Specifically, DIS binds within the aptamer's pre-folded TWJ target-binding domain without inducing a large conformational change in the aptamer.

In one embodiment, exonuclease, e.g., Exo III, digests the fully folded aptamer, such as DIS-37 (SEQ ID NO: 17), and such digestion is inhibited in the presence of DIS. In specific embodiments, regardless of the presence or absence of DIS, Exo III rapidly removed the first three nucleotides from the 3' end of DIS-37, resulting in a 34 nucleotides digestion product (e.g., a truncated aptamer selective for DIS), i.e., DIS-34 (SEQ ID NO: 18). In the absence of DIS, Exo III continues digestion, forming three intermediate products (33-, 32-, and 31-nt) and eventually resulting in a 30-nt major product, i.e., DIS-30 (SEQ ID NO: 20).

In one embodiment, the major digestion product, DIS-34 (SEQ ID NO: 18), generated in the presence of DIS remain bound to the target, indicating that DIS-34 exists in a folded state. In contrast, the major digestion product, DIS-30 (SEQ ID NO: 20), generated in the absence of DIS retains no binding affinity for DIS, indicating that DIS-30 exists in a single-stranded state.

In one embodiment, the truncated aptamer comprises the same TWJ domain for DIS binding as the parent aptamer. The TWJ-binding domain comprises at least one adenine and at least one thymine. In a further embodiment, the TWJ-binding domain comprises an adenine at position 21 (A21) and a thymine at position 30 (T30) of the parent aptamer (e.g., DIS-37) and the truncated aptamer (e.g., DIS-34). Mutations at one or more of these nucleotides impair the target-binding ability of these aptamers to DIS.

The aptamers of the present invention may or may not include chemical modifications. The chemical modifications as described herein include a chemical substitution at a sugar position, a phosphate position, and/or a base position of the nucleic acid including, for example, incorporation of a modified nucleotide, incorporation of a capping moiety (e.g., 3' capping), conjugation to a high molecular weight, non-immunogenic compound (e.g., polyethylene glycol (PEG)), conjugation to a lipophilic compound, and substitutions in the phosphate backbone. Base modifications may include 5-position pyrimidine modifications, modifications at exocyclic amines, substitution of 4-thiouridine, substitution of 5-bromo- or 5-iodo-uracil, and backbone modifications. Sugar modifications may include 2'-amine nucleotides (2'-NH2). 2'-fluoronucleotides (2'-F), and 2'-O-methyl (2'-OMe) nucleotides. Such modifications may improve the stability of the aptamers or make the aptamers more resistant to degradation. In some embodiments, each base of a given type (e.g., A, T, C, and G) may contain the same chemical modification.

The aptamers may or may not be modified by addition of one or more reporter labels (or detectable labels). In some embodiments, the label may be attached to either the 5' or 3' end of the aptamer. The label may also be attached with the backbone of the aptamer. The skilled person will be aware of techniques for attaching labels to nucleic acid strands. The detectable label may be attached directly or indirectly to the nucleic acid aptamer. If the label is indirectly attached to the nucleic acid aptamer, it may be by any mechanism known to one of skill in the art, such as using biotin and streptavidin.

The aptamers may or may not comprise a reporter label, such as a fluorescent dye, nanoparticle, or an enzyme. Exemplary labels include, but are not limited to, an organic donor fluorophore or an organic acceptor fluorophore, a luminescent lanthanide, a fluorescent or luminescent nanoparticle, an affinity tag such as biotin, or a polypeptide. In some embodiments, the aptamer may comprise a fluorescent label, for example, fluorescein, TAMRA, rhodamine, Texas Red, Alexa Fluor (e.g., AlexaFluor 488, AlexaFluor 532, AlexaFluor 546, AlexaFluor 594, AlexaFluor 633 and AlexaFluor 647), cyanine dye (e.g., Cy7, Cy7.5, Cy5, Cy5.5 and Cy3), Tye dye (e.g., TYE 563, TYE 665, TYE 705), atto dye (e.g., Atto 594 and Atto 633), Hexachlorofluorescein, FAM (6-carboxyfluroescein), BODIPY FL, OliGreen, 40,6-diamidino-2-phenylindol (DAPI), Hoechst 33,258, malachite green (MG), and FITC. The nanoparticle can be an upconversion nanoparticle. In some embodiments, the fluorophore is selected from the group consisting of fluorophores that emit a blue, green, near red or far red fluorescence.

In one embodiment, the truncated aptamer is modified with a fluorophore at one end and a quencher at the other end. In the absence of its target, the truncated aptamer is flexible, which positions the fluorophore far away from the quencher, thereby resulting in a fluorescence signal. Target binding to the truncated aptamer induces a conformational change that brings the fluorophore in close proximity to the quencher, and thus the fluorescence signal is attenuated. The resulting quenching of the fluorescence signal directly reflects the extent of the binding and can be used for detection and quantitative measurement of the target concentration.

In one embodiment an exonuclease-digested aptamer may bind to a complementary molecular beacon probe. The molecular beacon is modified with a fluorophore at one end and a quencher at the other end. In the absence of target, exonucleases will completely digest the aptamer, and thus the conformation of the molecular beacon remains in such a fashion that its fluorophore-quencher pair is close proximity, thus yielding no fluorescence signal. In the presence of target, exonuclease digestion of the aptamer is halted. Therefore the molecular beacon can bind to the resulting aptamer digestion product, which separates its fluorophore-quencher pair, resulting in a large fluorescence signal. The resulting recovery of the fluorescence signal directly reflects the extent of the binding and can be used for detection and quantitative measurement of the target concentration.

The quenchers can be, for example, Dabcyl, DDQ-I, Eclipse, Iowa Black FQ, BHQ-1, QSY-7, BHQ-2, DDQ-II, Iowa Black RQ, QSY-21, or BHQ-3.

In some embodiments, the fluorophore is at a location of, for example, 1st, 2nd, 3th, 4th, 5th, 6th, 7th, 8th, 9th, or 10th nucleotide from either the 5' end or 3' end of the aptamer.

The quencher is at a location of, for example, 1st, 2nd, 3th, 4th, 5th, 6th, 7th, 8th, 9th, or 10th nucleotide from either the 3' end or 5' end of the complementary sequence.

In preferred embodiments, the location of the fluorophore and quencher-conjugated is such that the proximity of fluorophore and quencher in a complementary sequence binding conformation provide maximal quenching and the fluorophore and quencher in a separated conformation provide maximal fluorescence of the fluorophore. For optimized detection of fluorescence changes that allows utilization of aptamers for target detection, it is desirable that the fluorescence in the quenched conformation is as low as possible and the fluorescence in the unquenched conformation is as high as possible combined with the most rapid interconversion from one conformation to the other.

In one embodiment, the aptamer can bind a dye such as a fluorophore within the double-stranded structures. The dye maybe SYBR Green I or SYBR Gold.

In one embodiment, the subject invention provides an electrochemical aptamer-based (E-AB) sensor comprising an aptamer labeled with a redox tag at one end and a functional group on the other end, wherein the aptamer is conjugated to an electrode surface via the functional group. Preferably, the functional group is thiol, and the redox tag is a methylene blue (MB) redox tag, which may label the aptamer at the 5' end, 3' end, or within the backbone. The electrode is made of, for example, gold, silver, or platinum.

In a preferred embodiment, the aptamer of the E-AB sensor is labeled with a 5' thiol and a 3' methylene blue (MB) redox tag and the modified aptamer is conjugated to a gold electrode surface via thiol-gold chemistry. In specific embodiments, the aptamer of E-AB sensor is a truncated aptamer having structure-switching functionality that enables the truncated aptamer a large conformational change upon binding of the target to form a target-aptamer complex. In a further embodiment, the truncated aptamer is a digestion product of a pre-folded parent aptamer by an exonuclease, e.g., Exo III.

In one embodiment, the aptamer binds to the small-molecule target with a dissociation constant of, for example, about 1 µM, about 2 µM, about 3 µM, about 4 µM, about 5 µM, about 6 µM, about 7 µM, about 8 µM, about 9 µM, or about 10 µM. In specific examples, The aptamer binds to the small molecule with a dissociation constant between about 0.001 µM and about 1000 µM, between about 0.01 µM and about 500 µM, between about 0.1 µM and about 200 µM, between about 0.5 µM and about 100 µM, between about 1 µM and about 100 µM, between about 1 µM and about 50 µM, between about 1 µM and about 30 µM, between about 1 µM and 20 µM, or between about 1 µM and about 10 µM.

Method of Using the Aptamer- and Exonuclease-Based Assays

The subject invention provides methods of using the exonuclease-based assays for generating structure-switching aptamers. The same method can also be used in aptamer-based assays for the detection of one or more small-molecule targets in a sample. The sample can be a complex sample.

In one embodiment, a pre-folded aptamer is truncated or digested by an exonuclease, e.g., Exo III. For example, in the absence of the small-molecule target, Exo III catalyzes 3'-to-5' digestion of the aptamers by the stepwise removal of mononucleotides, forming short, single-stranded products. On the other hand, in the presence of the small-molecule target, the truncation or digestion of the aptamer by, for example, Exo III is inhibited by the binding of the small-molecule target to the target-binding domain, forming a target-aptamer complex. The resulting aptamer digestion product (i.e., truncated aptamer) has structure-switching functionality, and this can be confirmed via digestion by Exo I, a single-strand 3'-to-5' exonuclease. In the absence of the target, the addition of Exo I leads to further digestion of the single-stranded oligonucleotide to mononucleotides. However, in the presence of target, Exo I fails to further digest the double-stranded target-aptamer complex. For small molecule detection, the remaining Exo III digestion products can then be quantified by, for example, fluorescent staining with a DNA-binding dye (e.g. SYBR Green I) and measuring the resulting fluorescent signal.

In one embodiment, the subject invention provides a method for generating structure-switching aptamers from fully folded or pre-folded aptamers and a means of rapid and sensitive detection of a small-molecule target. The generation of structure-switching aptamers entails digesting the aptamer with an exonuclease, such as Exo III. The resulting digestion product has structure-switching functionality with similar or equal affinity as its parent aptamer, and such aptamer can be directly employed in folding-based aptamer sensors.

In one embodiment, the method for generating a truncated aptamer having the structure-switching functionality, i.e., structure-switching aptamer, comprises providing a fully folded or pre-folded parent aptamer that does not have the structure-switching functionality, wherein the fully folded or pre-folded parent aptamer is specific for a small-molecule target, contacting the fully folded or pre-folded parent aptamer with an exonuclease, and generating the structure-switching aptamer, the structure-switching aptamer having the same target-binding domain as the pre-folded aptamer, the structure-switching aptamer having a target-induced structure-switching functionality. In a further embodiment, the exonuclease digests double-stranded DNA from the 3' end to the 5' end. Preferably, the exonuclease is Exo III.

In another embodiment, the truncated, structure-switching aptamer is at least 1, 2, 3, 4, 5, 6, 7, 8, 9, 10, 11, 12, 13, 14, 15, 16, 17, 18, 19, or 20 nucleotides shorter than the pre-folded parent aptamer, as a result of the digestion by, for example, Exo III.

In one embodiment, generating the structure-switching aptamer comprises removing mononucleotides from the 3' end of the pre-folded aptamer in a stepwise manner. Removing mononucleotides from the 3' end of the pre-folded aptamer by an exonuclease is inhibited at a position that is one or more nucleotides prior to the target binding domain, for example, 2, 3, 4, 5, 6, 7, 8, 9, 10, 11, 12, 13, 14, and 15 nucleotides prior to the target binding domain. In another embodiment, removing mononucleotides from the 3' end of the pre-folded aptamer by an exonuclease is inhibited when the 3' end of the pre-folded aptamer becomes single-stranded.

In one embodiment, the pre-folded aptamer comprises at least one, two or three double-stranded regions. The double-stranded region may comprise at least 2, 3, 4, 5, 6, 7, 8, 9, 10, 11, 12, 13, 14 or 15 base pairs. As a result of the truncation of the pre-folded aptamer by the exonuclease, the structure-switching aptamer is single-strand or partially single-stranded.

In one embodiment, the method for generating a truncated aptamer having the structure-switching functionality may further comprise the steps of determining the structure-switching aptamer by, for example, Exo I digestion and quantifying the Exo I digested product using PAGE analysis.

In specific embodiments, the parent aptamer is 38-GT (SEQ ID NO: 2), COC-38 (SEQ ID NO: 22) or ATP-33 (SEQ ID NO: 10). The structure-switching aptamer is 35-GT (SEQ ID NO: 3), COC-35 (SEQ ID NO: 23) or ATP-30 (SEQ ID NO: 11). The small-molecule target is cocaine or ATP.

In one embodiment, the subject invention provides a method for detecting a small molecule target in a sample using the truncated aptamers having structure-switching functionality. The method comprises contacting the sample with an aptamer-based sensor selective for the small-molecule target, wherein the aptamer-based sensor is an exonuclease-truncated aptamer having structure-switching functionality, i.e. structure-switching aptamer, and detecting the small-molecule target in the sample. In one embodiment, the detection of the small-molecule target further comprises measuring a signal generated upon binding of a signal reporter with the target-aptamer complex.

In some embodiments, the signal generated has optical properties selected from the group consisting of: light reflectivity, color, the fluorescence emission wavelength(s) and the fluorescence emission intensity. Preferably, the signal is a change in fluorescence intensity.

In one embodiment, the method for rapid and sensitive detection of a small-molecule target in a sample comprises
1) contacting the sample with an aptamer-based sensor selective for the small-molecule target,
2) contacting the mixture of step 1) with an exonuclease or with a mixture of exonucleases,
3) adding a signal reporter to the mixture of step 2); and
4) detecting the small molecule in the sample, the detection of the small-molecule target comprising measuring a signal generated from the signal reporter; wherein the aptamer-based sensor is a fully folded aptamer that does not have the structure-switching functionality, wherein the digestion product of step 2) by the exonuclease gains the structure-switching functionality, and wherein the exonuclease is Exo III.

In specific embodiments, the signal reporter is SYBR Green I, a commonly used DNA cyanine dye, binds to the double-stranded DNA, and thus, can be used for the detection of the folded target-aptamer complex, even in the presence of exonucleases.

In another embodiment, the method further comprises determining the concentration of the small-molecule target in the sample. The determination can comprise comparing the signal generated with a standard curve of such signal. For example, the determination based on SYBR Green I comprises comparing the fluorescence generated upon binding of SYBR Green I to double-stranded aptamer-target complex with a standard curve of the fluorescence of SYBR Green I. The read-out can be quantified in seconds by, for example, a microplate-reader or portable photometer, allowing for high-throughput or on-site detection, respectively. Thus, the fluorescence measured upon binding of a signal reporter with the folded target-aptamer complex is indicative of the presence of the small-molecule target in such sample.

In one embodiment, the subject invention provides a method for rapid and sensitive detection of cocaine in a sample comprising contacting the sample with an aptamer-based sensor selective for cocaine, wherein the aptamer-based sensor is an exonuclease-truncated aptamer, and detecting cocaine in the sample, wherein the detection of cocaine comprises measuring a signal generated upon binding of SYBR Green I with the folded cocaine-aptamer complex. This assay achieved a limit of detection of 1 µM cocaine in 10% saliva within 20 minutes.

In one embodiment, the subject invention provides a method for rapid and sensitive detection of cocaine in a sample comprising contacting the sample with an aptamer-based sensor selective for cocaine, wherein the aptamer-based sensor is a fully folded aptamer having structure-switching functionality upon digestion by Exo III, and detecting cocaine in the sample, wherein the detection of cocaine comprises measuring a signal generated upon binding of SYBR Green I with the folded cocaine-aptamer complex wherein the aptamer in the cocaine-aptamer complex is the digested product of the fully folded aptamer.

In specific embodiments, the fully folded aptamer is 38-GT (SEQ ID NO: 2), COC-38 (SEQ ID NO: 22) or ATP-33 (SEQ ID NO: 10). The exonuclease-truncated aptamer is 35-GT (SEQ ID NO: 3), COC-35 (SEQ ID NO: 23) or ATP-30 (SEQ ID NO: 11).

In one embodiment, the subject invention provides methods for detecting a small-molecule target by incorporating exonuclease-truncated aptamers into an E-AB sensor, which demonstrated target-induced conformational changes within the aptamers and achieved excellent sensor performance. In one embodiment, the method for rapid and sensitive detection of a small-molecule target in a sample comprises contacting the sample with an E-AB sensor selective for the small-molecule target, and detecting the small-molecule target in the sample. In one embodiment, the E-AB sensor comprises an exonuclease-truncated aptamer conjugated to an electrode surface, wherein the exonuclease-truncated aptamer is labeled with a 5' thiol and a 3' methylene blue (MB) redox tag, wherein the electrode is a gold electrode, and wherein the exonuclease-truncated aptamer is conjugated to a gold electrode surface via thiol-gold chemistry. In the absence of a target, the aptamer was primarily unfolded, prohibiting electron transfer from MB to the electrode. In the presence of a target, the aptamer undergoes a target-induced conformational change that brings MB close to the electrode surface, facilitating efficient electron transfer and resulting in an increase in current within seconds. In a further embodiment, the detection of the small-molecule target comprises measuring a signal generated upon binding of the small-molecule target with the E-AB sensor, wherein the signal is an increase in current.

In another embodiment, the method further comprises determining the concentration of the small-molecule target in the sample. The determination comprises comparing the current generated upon binding of the small-molecule target with the E-AB sensor with a standard curve. The read-out can be quantified in seconds by, for example, a voltmeter or a potentiostat. Thus, the current measured upon binding of the small-molecule target with the E-AB sensor is indicative of the presence of the small-molecule target in such sample.

In one embodiment, the method according to the subject invention can be used to detect cocaine in a sample. The method comprises contacting the sample with an E-AB sensor, wherein the E-AB sensor comprises an exonuclease-truncated aptamer selective for cocaine and the exonuclease-truncated aptamer is conjugated to the surface of a gold electrode; and detecting cocaine in the sample, wherein the detection of cocaine comprises measuring a current generated upon binding of cocaine with the E-AB sensor. In a specific embodiment, wherein the exonuclease-truncated aptamer selective for cocaine is 35-GT labeled with a 5' thiol and a 3' methylene blue (MB) redox tag. Advantageously, this method using E-AB sensor can detect cocaine in a sample within 10 seconds.

In some embodiments, the E-AB sensor is specific for cocaine and exhibits low cross-reactivity to DPH (20%) and SCP (10%) and minimal cross-reactivity to all cutting agents (caffeine, levamisole, lidocaine, and sucrose) (<5%).

In one embodiment, the subject invention provides a method for detecting a small-molecule target in a sample using the truncated aptamers having structure-switching functionality. The method comprises contacting the sample with an aptamer-based sensor selective for the small-molecule target, wherein the aptamer-based sensor is an exonuclease-truncated aptamer having structure-switching functionality, and detecting the small-molecule target in the sample. In one embodiment, the aptamer-based sensor is an exonuclease-truncated aptamer modified with a fluorophore-quencher pair, and the detection of the small-molecule target further comprises measuring a signal generated upon binding of the small-molecule target to the aptamer-based sensor. In a further embodiment, the signal is an increase or decrease in fluorescence from the fluorophore-quencher pair.

In one embodiment, the subject invention provides methods for detecting a small-molecule target by employing an exonuclease-truncated aptamer in a fluorophore-quencher assay, which demonstrates target-induced conformational changes within the aptamers and achieved excellent sensor performance.

In one embodiment, the method for detecting a small-molecule target in a sample comprising contacting the sample with a fluorophore-quencher sensor selective for the small-molecule target, and detecting the small-molecule target in the sample. The detection of the small-molecule target further comprises measuring a signal reduction upon binding of the small-molecule target with the fluorophore-quencher sensor.

In one embodiment, the fluorophore-quencher sensor comprises an exonuclease-truncated aptamer labeled with a fluorophore-quencher pair at 3' and 5' ends. Preferably, the fluorophore is Cy5 at the 3' end of the exonuclease-truncated aptamer and the quencher is IowaBlack at the 5' end of the exonuclease-truncated aptamer. In the absence of target, the aptamer is primarily unfolded and the fluorophore is separated from the quencher, producing a large fluorescence background signal. In the presence of the target, the aptamer undergoes a target-induced conformational change that brings the fluorophore in close proximity to the quencher, yielding a strong reduction in fluorescence within seconds.

In another embodiment, the method further comprises determining the concentration of the small-molecule target in the sample. The determination can comprise comparing the signal generated with a standard curve of such signal. For example, the determination based on the fluorophore-quencher sensor comprises comparing the fluorescence reduction upon binding of the small-molecule target to the fluorophore-quencher sensor with a standard curve of the fluorescence of the fluorophore. The read-out can be quantified in seconds by, for example, a microplate-reader or portable photometer, allowing for high-throughput or on-site detection, respectively. Thus, the fluorescence reduction measured is indicative of the presence of the small-molecule target in such sample.

In one embodiment, the method according to the subject invention can be used to detect ATP in a sample. The method comprises contacting the sample with a fluorophore-quencher sensor, and detecting ATP in the sample. In one embodiment, the fluorophore-quencher sensor comprises an exonuclease-truncated aptamer selective for ATP, and the exonuclease-truncated aptamer is labelled with a fluorophore-quencher pair at 3' and 5' ends. Preferably, the exonuclease-truncated aptamer is labelled with Cy5 at the 3' end and IowaBlack at the 5' end. In a specific embodiment, the exonuclease-truncated aptamer is ATP-30 (SEQ ID NO: 11) and the labeled aptamer is ATP-30-FQ (SEQ ID NO: 13). The detection of ATP further comprises measuring a fluorescence reduction upon binding of ATP with the fluorophore-quencher sensor. Advantageously, such method can detect ATP in a sample within seconds.

In one embodiment, the subject invention further provides methods employing an exonuclease-inhibition fluorescence assay using exonuclease-directed truncation strategies. This assay can achieve sensitive small-molecule detection via quantification of aptamer digestion products. Such assay does not require any prior sequence engineering, truncation, or labeling. In preferred embodiments, the methods employ high-affinity, fully folded aptamers, Exo III, and Exo I to sensitively detect small-molecule targets via the quantification of aptamer digestion products with the assistance of signal reporters such as, but not limited to, SYBR Gold. As a result, the concentrations of the small-molecule target can be quantified based on the extent of aptamer digestion. Additionally, this approach employs unmodified pre-folded aptamers that have higher target-binding affinities than structure-switching aptamers which fold upon the binding of the target.

In one embodiment, the subject invention provides a method for rapid and sensitive detection of a small-molecule target in a sample comprising:
1) contacting the sample with an aptamer-based sensor selective for the small-molecule target,
2) contacting the mixture of step 1) with a first exonuclease,
3) contacting the mixture of step 2) with a second exonuclease,
4) adding a signal reporter to the mixture of step 3); and
5) detecting the small molecule in the sample, the detection of the small-molecule target comprising measuring a signal generated from the signal reporter.

In specific embodiments, the aptamer-based sensor comprises a fully folded aptamer having a target-binding domain; the first exonuclease is Exo III; the second exonuclease is Exo I; and the signal reporter is a fluorescent dye. In a further embodiment, the target-binding domain is the TWJ-binding domain. In another embodiment, the target-binding domain locates in the loop domain in the hairpin structure.

In the absence of the small-molecule target, unbound, folded aptamers can be digested by the first exonuclease, e.g., Exo III, resulting in a single-stranded oligonucleotide that can further be digested by the second exonuclease, e.g., Exo I, into mononucleotides. As a result, no signal can be detected upon contacting a signal reporter that only binds to the single-stranded oligonucleotide. By contrast, in the presence of the small-molecule target, the digestion by the first exonuclease, e.g., Exo III is inhibited for the target-bound aptamers, resulting in an intermediate exonuclease-truncated aptamer binding with the small-molecule target. Such Exo III digestion product of the target-bound aptamer strongly prohibits the digestion by the second exonuclease, i.e., Exo I because they exist in a double-stranded state. The digestion product of the target-bound aptamer can then be detected and quantified by contacting a signal reporter, such as SYBR Gold.

In one embodiment, the method comprises a step to deactivate the exonucleases and denature all major products into single-stranded structures prior to the step of adding the signal reporter. In a specific embodiment, a solution containing EDTA and formamide can be used to deactivate the exonucleases and denature all major products into single-stranded structures.

In one embodiment, the subject invention provides a method for rapid and sensitive detection of DIS in a sample comprising 1) contacting the sample with an aptamer-based sensor selective for DIS, the aptamer-based sensor comprises a fully folded aptamer having a TWJ-binding domain; 2) contacting the mixture of step 1) with Exo III; 3) contacting the mixture of step 2) with Exo I; 4) contacting the mixture of step 3) with a signal reporter; and 5) detecting DIS in the sample.

In one embodiment, the detection of DIS comprises measuring a signal generated upon binding of a signal reporter, such as SYBR Gold, with the single-stranded aptamer wherein the single-stranded aptamer is the digested product of the pre-folded aptamer. The single-stranded aptamer is produced by contacting the digestion mixture of DIS-specific aptamer and the exonuclease with a solution containing EDTA and formamide to deactivate the exonucleases and denature all major products into single-stranded structures. This method is very sensitive and has extremely low-background, achieving a detection limit of 500 nM DIS within 15 minutes. In a specific embodiment, the DIS-specific aptamer is DIS-37 and the digested product of the DIS-specific aptamer is DIS-34.

In one embodiment, the subject invention provides a method for rapid and sensitive detection of cocaine in a sample, wherein the method comprises contacting the sample with an aptamer-based sensor selective for cocaine, wherein the aptamer-based sensor is a fully folded aptamer having a TWJ-binding domain and digested by a mixture of Exo III and Exo I, and detecting cocaine in the sample, wherein the detection of cocaine comprises measuring a signal generated upon binding of SYBR Gold with the single-stranded aptamer, and wherein the single-stranded aptamer is the digested product of the pre-folded aptamer. The single-stranded aptamer is produced by contacting the digestion mixture of cocaine-specific aptamer and the exonuclease with a solution containing EDTA and formamide to deactivate the exonucleases and denature all major products into single-stranded structures. This method is very sensitive and has extremely low-background, achieving a detection limit of 100 nM cocaine within 15 minutes. In a specific embodiment, the cocaine-specific aptamer is COC-38 and the digested product of the cocaine-specific aptamer is COC-35.

In one embodiment, the subject invention provides a method for rapid and sensitive detection of ATP in a sample comprising contacting the sample with an aptamer-based sensor selective for ATP, wherein the aptamer-based sensor is a fully folded aptamer having a hairpin structure and digested by a mixture of Exo III and Exo I, and detecting ATP in the sample, wherein the detection of ATP comprises measuring a signal generated upon binding of SYBR Gold with the single-stranded aptamer, and wherein the single-stranded aptamer is the digested product of the pre-folded aptamer. The single-stranded aptamer is produced by contacting the digestion mixture of ATP-specific aptamer and the exonuclease with a solution containing EDTA and formamide to deactivate the exonucleases and denature all major products into single-stranded structures. This method is very sensitive and has extremely low background, achieving a detection limit of 250 nM ATP within 15 minutes. In a specific embodiment, the ATP-specific aptamer is ATP-33 and the digested product of the ATP-specific aptamer is ATP-30.

In one embodiment, the subject invention further provide methods for single-pot, multiplex small-molecule detection, which is a highly valuable and vital tool for medical diagnostics, drug screening, environmental monitoring, biodefence, and food safety as it enables detection of a multitude of analytes with only a single low-volume sample. The methods also employ the exonuclease-inhibition strategies and the digestion product of each aptamer-target pair has a unique sequence that can be specifically recognized by an antisense DNA probe.

In one embodiment, the aptamer digestion products serve as proxies for each individual target and can be quantified using molecular beacons that are designed to specifically hybridize with an individual digested aptamer strand. The resulting signal can be used to accurately determine the concentration of the target.

In one embodiment, the method for detecting one or more small-molecule targets in a sample comprises contacting the sample with one or more aptamer-based sensors selective for each of the small-molecule targets, wherein the one or more aptamer-based sensors are digested by, for example, Exo III and Exo I, and detecting one or more small-molecule target in the sample. The method further comprises adding one or more molecular beacons that specifically hybridize with each digested aptamer strand. The detection of one or more small-molecule targets further comprises measuring one or more signals generated upon reaction between one or more molecular beacons with each aptamer.

In the absence of the targets, both Exo III and Exo I completely digest all aptamers. Upon addition of the molecular beacons that are modified with a fluorophore-quencher pair, no fluorescence is generated as the beacons exist in a closed state, where the fluorophore is in close proximity to the quencher. However, in the presence of one or more target, the exonucleases will generate specific aptamer digestion products that hybridize with their corresponding molecular beacon(s), separating the fluorophore from the quencher and generating one or more fluorescence signals.

In one embodiment, the molecular beacon comprises a hairpin structure comprising a stem and a loop region. The stem comprises at least 2, 3, 4, 5, 6, 7, 8, 9, 10, 11, or 12 base pairs. Preferably, the stem comprises six base pairs. The loop comprises a sequence that is complementary to the digested aptamer stand, allowing this region to hybridize the specific aptamer.

In specific embodiments, the method employs two fluorophore-quencher modified molecular beacons to simultaneously detect ATP and cocaine in a sample. The molecular beacons have the same six base-pair stem but with different complementary loop regions. The molecular beacon for ATP (ATP-MB) contains a 28-nt loop that is complementary to the exonuclease digestion product of ATP-33 (i.e., ATP-30) and is modified with a 5' Cy5 and 3' Iowa Black RQ quencher. The molecular beacon for cocaine (COC-MB) contains a 33-nt loop that is complementary to the exonuclease digestion product of COC-38 (i.e., COC-35) and is modified with a 5' FAM and a 3' Black Hole Quencher 1.

In the absence of ATP and cocaine, both Exo III and Exo I completely digest all aptamers. Upon addition of the molecular beacons, no fluorescence is generated. However, in the presence of either or both ATP and cocaine, Exo III generates specific aptamer digestion products which hybridize with their corresponding molecular beacon(s), separating the fluorophore from the quencher and generating a single (cocaine or ATP) or dual (ATP and cocaine) fluorescence signal.

In another embodiment, the method further comprises determining the concentration of one or more small-molecule targets in the sample. The determination can comprise comparing the signal generated upon the hybridization of each molecular beacon with specific aptamer digestion products with a standard curve of such signal. The read-out can be quantified in seconds by, for example, a microplate-reader or portable photometer, allowing for high-throughput or on-site detection, respectively. Thus, the increase in fluorescence is indicative of the presence of the small-molecule target in such sample.

In one embodiment, the methods using the exonuclease-inhibition assay can demonstrate activity in a variety of buffer conditions and biological sample matrices, and can be utilized with different aptamer-target pairs. The methods according to the subject invention, therefore, can be generalizable for any other small-molecule binding aptamers, regardless of their structure.

In one embodiment, the method according to the subject invention can achieve superior sensitivity for target detection at low micromolar or nanomolar concentration, for example, as low as about 200 µM, about 150 µM, about 100 µM, about 10 µM, about 1 µM, about 100 nM, about 10 nM, or about 1 nM.

In one embodiment, the methods for small molecule detection provided herein are rapid and can be completed in about 5 minutes to about 120 minutes, about 6 minutes to about 110 minutes, about 7 minutes to about 100 minutes, about 8 minutes to about 90 minutes, about 9 minutes to about 80 minutes, about 10 minutes to about 70 minutes about 15 minutes to about 60 minutes, about 20 minutes to about 50 minutes, or about 25 minutes to about 40 minutes. In some embodiments, the method can be completed in about 5 minutes, about 10 minutes, about 15 minutes, about 20 minutes, about 25 minutes, about 30 minutes, about 35 minutes, about 40 minutes, about 45 minutes, about 50 minutes, about 55 minutes, about 60 minutes, about 65 minutes, about 70 minutes, about 75 minutes, about 80 minutes, about 85 minutes, about 90 minutes, about 95 minutes, about 100 minutes, about 105 minutes, about 110 minutes, about 115 minutes, or about 120 minutes.

In another embodiment, the methods for small molecule detection provided herein are rapid and can be completed in about 5 seconds to about 5 minutes, about 10 seconds to about 4 minutes, about 15 seconds to about 3 minutes, about 20 seconds to about 2 minutes, or about 25 seconds to about 1 minute.

In one embodiment, the subject invention provides a method for detecting small molecules that are biomarkers for diagnosis of a disease or condition, or monitoring therapeutic response to specific treatments. In specific embodiments, the condition can be, for example, cancer, an injury, an inflammatory disease or a neurodegenerative disease. In some embodiments, the condition can be substance abuse, psychosis, schizophrenia, Parkinson's disease, attention deficit hyperactivity disorder (ADHD), and pain. In some embodiments, the pain is acute pain or chronic pain. In some embodiments, the pain is neuropathic pain, e.g., chronic neuropathic pain.

In one embodiment, the subject invention provides a kit for detecting a small-molecule target, comprising the aptamer-based sensor and one or more exonucleases, wherein the aptamer-based sensor comprises an aptamer, and binding of the small-molecule target to the aptamer inhibits the digestion of the aptamer by one or more exonucleases. In preferred embodiments, one or more exonucleases include Exo I and Exo III. The kit can further comprise instructions for using the kit. In some embodiments, the kit may comprise other reagents suitable for detecting the small-molecule target. The reagents may include fluorophores, fluorophore-quencher pairs, and stabilizing agents.

In one embodiment, the methods, assays and products according to the subject invention can be used for the sensitive and accurate detection of small-molecule targets in fields including environmental monitoring, food safety, law enforcement, medical diagnostics, and public health.

The subject invention encompasses the use of sequences having a degree of sequence identity with the nucleic acid sequence(s) of the present invention. A similar sequence is taken to include a nucleotide sequence which may be at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to the subject sequence. Typically, the similar sequences will comprise the same or similar secondary structure as the subject nucleic acid aptamer. In one embodiment, a similar sequence is taken to include a nucleotide sequence which has one or several additions, deletions and/or substitutions compared with the subject sequence.

EXAMPLES

Experimental Section

Materials and Methods
Reagents.

Exonuclease III and exonuclease I (both from *E. coli*) were purchased from New England Biolabs. Adenosine-5'-triphosphate (ATP) disodium salt trihydrate was purchased from MP Biomedical. Formamide was purchased from Fisher Scientific. Cocaine hydrochloride, dehydroisoandrosterone-3-sulfate (DIS), cocaethylene, methylecgonidine, diphenhydramine, nicotine, and scopolamine and all other chemicals were purchased from Sigma-Aldrich unless otherwise specified. Benzoylecgonine tetrahydrate was purchased from Cerilliant Corporation. SYBR Gold and SYBR Green I were purchased from Invitrogen. 2-amino-5,6,7-trimethyl-1,8-naphthyridine (ATMND) was purchased from Ryan Scientific. All oligonucleotides were ordered from Integrated DNA Technologies, purified with HPLC, and dissolved in PCR water. DNA concentrations were measured using a NanoDrop 2000 (Thermo Scientific). DNA sequences employed in this work are listed below. Mutated nucleotides of 38-GT are underlined.

```
38-GC:
                                      (SEQ ID NO: 1)
5'-GGG AGA CAA GGA AAA TCC TTC AAC GAA GTG GGT CTC
CC-3'

38-GT:
                                      (SEQ ID NO: 2)
5'-GGG AGA CAA GGA AAA TCC TTC AAT GAA GTG GGT CTC
CC-3'

35-GT:
                                      (SEQ ID NO: 3)
5'-GGG AGA CAA GGA AAA TCC TTC AAT GAA GTG GGT CT-
3'

31-GT:
                                      (SEQ ID NO: 4)
5'-GGG AGA CAA GGA AAA TCC TTC AAT GAA GTG G-3'

38-GT-20C:
                                      (SEQ ID NO: 5)
5'-GGG AGA CAA GGA AAA TCC TCC AAT GAA GTG GGT
CTC CC-3'

38-GT-20A:
                                      (SEQ ID NO: 6)
5'-GGG AGA CAA GGA AAA TCC TAC AAT GAA GTG GGT
CTC CC-3'

38-GT-22G:
                                      (SEQ ID NO: 7)
5'-GGG AGA CAA GGA AAA TCC TTC GAT GAA GTG GGT
CTC CC-3'

38-GT-22T:
                                      (SEQ ID NO: 8)
5'-GGG AGA CAA GGA AAA TCC TTC TAT GAA GTG GGT
CTC CC-3'

32-GT-MB:
                                      (SEQ ID NO: 9)
5'-SH-C6-AGA CAA GGA AAA TCC TTC AAT GAA GTG GGT
CT-MB-3'
```

-continued

ATP-33:
(SEQ ID NO: 10)
5'-CGC ACC TGG GGG AGT ATT GCG GAG GAA GGT GCG-3'

ATP-30:
(SEQ ID NO: 11)
5'-CGC ACC TGG GGG AGT ATT GCG GAG GAA GGT-3'

ATP-25:
(SEQ ID NO: 12)
5'-CGC ACC TGG GGG AGT ATT GCG GAG G-3'

ATP-30-FQ:
(SEQ ID NO: 13)
5'-/IAbRQ/CGC ACC TGG GGG AGT ATT GCG GAG GAA GGT/3Cy5Sp/-3'

ATP-33-M:
(SEQ ID NO: 14)
5'-CGC ACC TGG GG<u>A</u> AGT ATT GCG G<u>T</u>G GAA GGT GCG-3'

ATP-SW-34:
(SEQ ID NO: 15)
5'-CCT CCT ACC TGG GGG AGT ATT GCG GAG GAA GGT A-3'

ATP-MB:
(SEQ ID NO: 16)
5'-/5Cy5/GCG AGC TTT CCT CCG CAA TAC TCC CCC AGG TGC GGC TCG C/3IAbRQSp/-3'

DIS-37:
(SEQ ID NO: 17)
5'-TCG GGA CGT GGA TTT CCG CA TAC GAA GTT GTC CCG A-3'

DIS-34:
(SEQ ID NO: 18)
5'-TCG GGA CGT GGA TTT CCG CA TAC GAA GTT GTC C-3'

DIS-33:
(SEQ ID NO: 19)
5'-TCG GGA CGT GGA TTT CCG CA TAC GAA GTT GTC-3'

DIS-30:
(SEQ ID NO: 20)
5'-TCG GGA CGT GGA TTT CCG CA TAC GAA GTT-3'

DIS-37-M:
(SEQ ID NO: 21)
5'-TCG GGA CGT GGA TTT CCG C<u>C</u> TAC GAA GT<u>C</u> GTC CCG A-3'

COC-38:
(SEQ ID NO: 22)
5'-GGG TGA CAA GGA AAA TCC TTC AAT GAA GTG GGT CAC CC-3'

COC-35:
(SEQ ID NO: 23)
5'-GGG TGA CAA GGA AAA TCC TTC AAT GAA GTG GGT CA-3'

COC-33:
(SEQ ID NO: 24)
5'-GGG TGA CAA GGA AAA TCC TTC AAT GAA GTG GGT-3'

COC-38-M:
(SEQ ID NO: 25)
5'-GGG TGA CAA GGA AAA TCC TTC <u>G</u>AT GAA GTG GGT CAC CC-3'

COC-MB:
(SEQ ID NO: 26)
5'-/56-FAM/GCG AGC ACC CAC TTC ATT GAA GGA TTT TCC TTG TCA CCC GCT CGC/BHQ1/-3'

(a. /56-FAM/ represents FAM; b. /5Cy5/ represents Cy5; c. /BHQ1/ represents Blackhole Quencher 1 d. /3IAbRQSp/ represents Iowa Black RQ)

Aptamer Digestion with Exo III or Exo I and Characterization of Digestion Products Using Polyacrylamide Gel Electrophoresis (PAGE).

The digestion of the cocaine-binding aptamer and its derivatives were performed using 1 µL of aptamer (final concentration 1 µM) in 44 µL of reaction buffer (10 mM Tris, 0.1 mM MgCl$_2$, 0.1 mg/mL BSA, pH 7.4) containing cocaine (final concentration 250 µM) in a 200 µL PCR tube. The tube was placed in a thermal cycler (Bio-Rad) and incubated at 23° C. for 15 minutes. 5 µL of Exo III (final concentration 0.26 U/µL) or Exo I (final concentration 0.09 U/µL) was then added to initiate digestion.

The digestion of ATP-binding aptamers was performed using 1 µL of aptamer (final concentration 1 µM) in 44 µL of reaction buffer (10 mM Tris, 10 mM MgCl$_2$, 0.1 mg/mL BSA, pH 7.4) containing ATP (final concentration 250 µM) in a 200 µL PCR tube. After a 15-min incubation at 23° C., 5 µL of Exo III (final concentration 0.05 U/µL) or Exo I (final concentration 0.14 U/µL) was then added to perform the digestion.

For both ATP and cocaine-binding aptamers, 5 µL digestion products was collected at various time points and stopped with 10 µL formamide loading buffer (71.25% formamide, 10% glycerol, 0.125% SDS, 25 mM EDTA, and 0.15% (w/v) bromophenol blue and xylene cyanol). 3 µL of each sample was loaded onto 15% denaturing PAGE gel and separation was carried out at 20 V/cm for 3 hours in 0.5×TBE running buffer. The gel was stained with 1×SYBR Gold for 25 minutes and imaged using a ChemiDoc MP imaging system (Bio-Rad).

Aptamer Digestion with Exo III and Exo I and Characterization of Digestion Products Using Polyacrylamide Gel Electrophoresis (PAGE).

1 µL of 50 µM aptamer or mutant aptamer was added into 44 µL of reaction buffer containing various concentrations of the appropriate target in a 200 µL PCR tube. The buffer composition varied for each aptamer-target pair, with final concentrations for each reaction as follows: DIS (20 mM Tris, 25 mM MgCl$_2$, 1% DMSO, 0.1 mg/mL BSA, pH 7.4), cocaine (10 mM Tris, 100 mM NaCl, 1 mM MgCl$_2$, 0.1 mg/mL BSA, pH 7.4), and ATP (10 mM Tris, 10 mM MgCl$_2$, 0.1 mg/mL BSA, pH 7.4).

Reaction mixtures were placed in a thermal cycler (C1000 Touch, Bio-Rad) and incubated at 23° C. for 60 min, after which 5 µL of the enzyme(s) were added to each reaction mixture. For DIS, the enzyme concentrations used were 0.13 U/µL Exo III, 1.5 U/µL Exo I, or a mixture of 0.13 U/µL Exo III+1.5 U/µL Exo I. For cocaine, the enzyme concentrations used were 0.4 U/µL Exo III, 0.9 U/µL Exo I, or a mixture of 0.4 U/µL Exo III+0.9 U/µL Exo I. For ATP, the enzyme concentrations used were 0.5 U/µL Exo III, 1.4 U/µL Exo I, or a mixture of 0.5 U/µL Exo III+1.4 U/µL Exo I. For all experiments, 5 µL of sample was collected at various time points and mixed with 10 µL of formamide loading buffer (75% formamide, 10% glycerol, 0.125% SDS, 10 mM EDTA, and 0.15% (w/v) xylene cyanol) to quench the reaction.

Digestion products were analyzed by polyacrylamide gel electrophoresis (PAGE). Specifically, 3 µL of each collected sample was loaded into the wells of a 15% denaturing PAGE gel. Separation was carried out at 20 V/cm for 3 hrs in 0.5×TBE running buffer. The gel was stained with 1×SYBR Gold solution for 25 min and imaged using a ChemiDoc MP Image system (Bio-Rad).

Preparation of a Customized DNA Ladder.

Figures 1A, 1B:
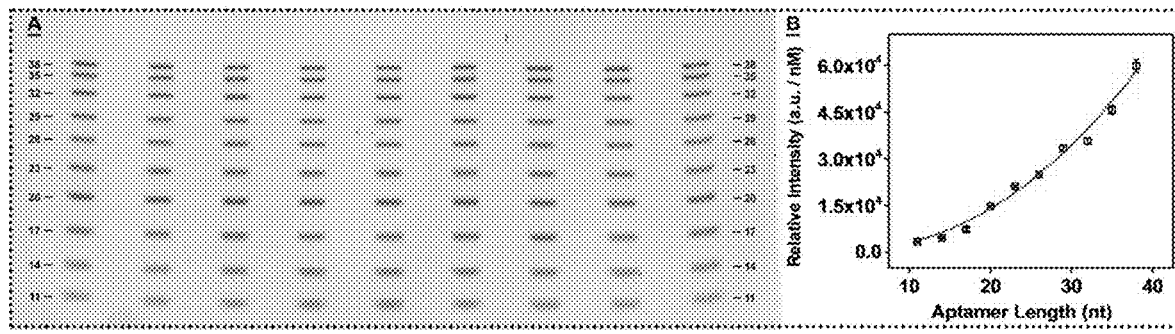
FIGS. 1A-1B show utilization of a customized DNA ladder loaded in a polyacrylamide gel to generate a curve for calculating the concentrations of digestion products. (1A) Polyacrylamide gel electrophoresis (PAGE) analysis of the DNA ladder. Respective concentrations of the 38-, 35-, 32-, 29-, 26-, 23-, 20-, 17-, 14-, and 11-nt in loading buffer are 20, 25, 32, 34, 46, 60, 80, 200, 300 and 400 nM. (1B) Plot of each band's intensity divided by concentration versus fragment length. Error bars represent standard deviation of nine measures in one gel.

A customized DNA ladder was used to identify the length and concentration of digestion products in gel. The adder components were designed by removing nucleotides from the 3' end of 38-GT. The final ladder mixture comprised 38-, 35-, 32-, 29-, 26-, 23-, 20-, 17-, 14-, and 11-nt fragments in loading buffer at concentrations of 20, 25, 32, 34, 46, 60, 80, 200, 300 and 400 nM, respectively. A plot of each band's intensity divided by oligonucleotide concentration versus its length was generated (FIG. 1), and the resulting curve was used to calculate the concentrations of digestion products. The following oligonucleotides are contained in the ladder:

38-GT:
(SEQ ID NO: 2)
5'-GGG AGA CAA GGA AAA TCC TTC AAT GAA GTG GGT CTC CC-3'

35-GT:
(SEQ ID NO: 3)
5'-GGG AGA CAA GGA AAA TCC TTC AAT GAA GTG GGT CT-3'

32-nt:
(SEQ ID NO: 27)
5'-GGG AGA CAA GGA AAA TCC TTC AAT GAA GTG GG-3'

29-nt:
(SEQ ID NO: 28)
5'-GGG AGA CAA GGA AAA TCC TTC AAT GAA GT-3'

26-nt:
(SEQ ID NO: 29)
5'-GGG AGA CAA GGA AAA TCC TTC AAT GA-3'

23-nt:
(SEQ ID NO: 30)
5'-GGG AGA CAA GGA AAA TCC TTC AA-3'

20-nt:
(SEQ ID NO: 31)
5'-GGG AGA CAA GGA AAA TCC TT-3'

17-nt:
(SEQ ID NO: 32)
5'-GGG AGA CAA GGA AAA TC-3'

14-nt:
(SEQ ID NO: 33)
5'-GGG AGA CAA GGA AA-3'

11-nt:
(SEQ ID NO: 34)
5'-GGG AGA CAA GG-3'

SYBR Green I Fluorescence Experiments.

After Exo III digestion, 50 μL of digestion products were mixed with 50 μL of 1×SYBR Green I diluted with 10 mM Tris buffer (pH 7.4) including 2 mM EDTA. 80 μL of this mixture was loaded into one well of a 96-well plate. Fluorescence intensities were recorded using a Tecan Infinite M1000 PRO with excitation at 497 nm and emission at 520 nm.

SYBR Gold Fluorescence Experiments.

The dual-exonuclease inhibition assay was performed using various concentrations of DIS (0, 0.5, 1, 2.5, 5, 10, 15, 25, 33, 50, 75, 100, and 250 μM), cocaine (0, 0.1, 0.25, 0.5, 1, 2.5, 5, 10, 20, 35, 50, 75, 125, 200, 500, and 1000 μM), ATP (0, 0.25, 0.5, 1, 2.5, 5, 10, 15, 25, 50, 100, and 250 μM). After digestion, 50 μL of digestion products were mixed with 50 μL of 2×SYBR Gold diluted in 10 mM Tris buffer (pH 7.4) containing 100 mM EDTA and 25% formamide (v/v). 80 μL of the mixture was loaded into the wells of a 96-well plate.

Fluorescence emission spectra were recorded from 510-850 nm using a Tecan microplate reader (Infinite M1000 PRO, Switzerland) with a 495-nm excitation wavelength. The fluorescence intensity recorded at 545 nm was used to calculate signal gain using the equation $(F-F_0)/F_0$ where F and $F_0$ represent fluorescence intensity in the presence and absence of target, respectively. Calibration curves were constructed by plotting signal gains against target concentrations. Each experiment was performed in triplicate and error bars represent the standard deviation of three measurements.

ATMND-Displacement Experiments.

96 μL of binding buffer (10 mM Tris, 0.01 mM MgCl$_2$, pH 7.4) containing 0.25 μM ATMND and 2 μM 38-GT was loaded into wells of a 96-well plate. Then 2 μL of cocaine, cocaine metabolite, or interferents (final concentration 250 μM) was added into the well and fluorescence was measured using a Tecan Infinite M1000 PRO with excitation at 358 nm and emission at 405 nm.

Isothermal Titration Calorimetry (ITC) Experiments.

All ITC experiments were performed with a MicroCal ITC200 instrument (Malvern) at 23° C. in the respective buffer of each aptamer-target pair with a MicroCal iTC200 instrument (GE Healthcare). The sample cell contained 20 μM aptamer, e.g., cocaine-binding aptamers, ATP-binding aptamers, DIS-binding aptamers, or mutant aptamers, while 500 μM cocaine, cocaine metabolite, or cocaine interferents, 500 μM DIS, or 800 μM ATP was loaded in the syringe. Specifically, each experiment consisted of 19 successive 2 μL injections after a 0.4 μL purge injection with spacing of 180 seconds. The raw data were first corrected based on the dilution heat of each target, and then analyzed with the MicroCal analysis kit integrated into Origin 7 software with a single-site binding model for DIS and cocaine or a two-site sequential binding model for ATP to calculate $K_D$ or $K_{1/2}$.

Fabrication of an Electrochemical Aptamer-Based (E-AB) Sensor for Cocaine Detection.

The E-AB sensor was fabricated by using polycrystalline gold disk electrodes (1.6 mm diameter; BAS). The electrodes were polished and cleaned by following a previously published protocol. The clean gold electrode was incubated with a 25 nM solution of 5' thiolated, 3' methylene blue-modified 35-GT containing 2 mM tris-(2-carboxyethyl) phosphine hydrochloride in phosphate-buffered saline (PBS) (10 mM phosphate, 1 μM NaCl, and 1 mM MgCl$_2$, pH 7.2) for 12 hours. The surface was then rinsed with deionized water and passivated with 3 mM 6-mercaptohexanol in the same PBS buffer for 2 hours. The electrode was incubated in a Tris buffer (10 mM Tris, 1 mM NaCl, and 0.03 mM MgCl$_2$, pH 7.4) for 1 hour prior to the measurements. Sensor performance was evaluated by monitoring the electrode in Tris buffer containing cocaine, benzoylecgonine, cocaethylene, methylecgonidine, diphenhydramine, nicotine, or scopolamine using square wave voltammetry (CH Instruments).

Fluorescence Assay for ATP Detection.

1 μL ATP-30-FQ (final concentration 1 μM) and 89 μL of ATP binding buffer (10 mM Tris-HCl, 0.1 mM MgCl$_2$, pH 7.4) were mixed with 10 μL of solution containing various concentrations of ATP and added into wells of a 96-well plate. After a 1-minute incubation at room temperature, fluorescence emission spectra were recorded from 660-850 nm using a Tecan Infinite M1000 PRO at a 648-nm excitation wavelength. Signal gain was calculated by $(F_0-F)/F_0$, where $F_0$ and F is the fluorescence intensity of ATP-free and ATP-containing sample at 668 nm, respectively. Each sample was analyzed in triplicate and means and standard deviations were plotted.

Multiplex Target Detection Using Fluorophore-Quencher-Modified Molecular Beacons.

Multiplex detection of cocaine and ATP was performed as follows. 1 µL of 25 µM COC-38 and 1 µL of 25 µM ATP-33 was added into 43 µL of reaction buffer (10 mM Tris, 100 mM NaCl, 1 mM $MgCl_2$, and 0.1 mg/mL BSA, pH 7.4) containing various concentrations of either cocaine, ATP, or both in a 200 µL PCR tube. Reaction mixtures were placed in a thermal cycler and incubated at 23° C. for 60 min, after which 5 µL of an exonuclease mixture (0.5 U/µL Exo III+1.5 U/µL Exo I) was added into each sample. After a 20-min reaction, 40 µL of stop solution (10 mM Tris, 12.5 mM EDTA, and 500 mM NaCl, pH 7.4) was added to quench the enzymatic reaction. Then, 10 µL of a molecular beacon mixture (200 nM COC-MB+200 nM ATP-MB) prepared in hybridization buffer (10 mM Tris buffer, 500 mM NaCl, and 1 mM $MgCl_2$, pH 7.4) was introduced to quantify the digested aptamer(s). 80 µL of the mixture was immediately loaded into the wells of a 96-well plate. Fluorescence emission spectra were recorded with a 495-nm excitation wavelength for FAM and with a 645-nm excitation wavelength for Cy5 using a Tecan microplate reader.

Figures 2A, 2B:
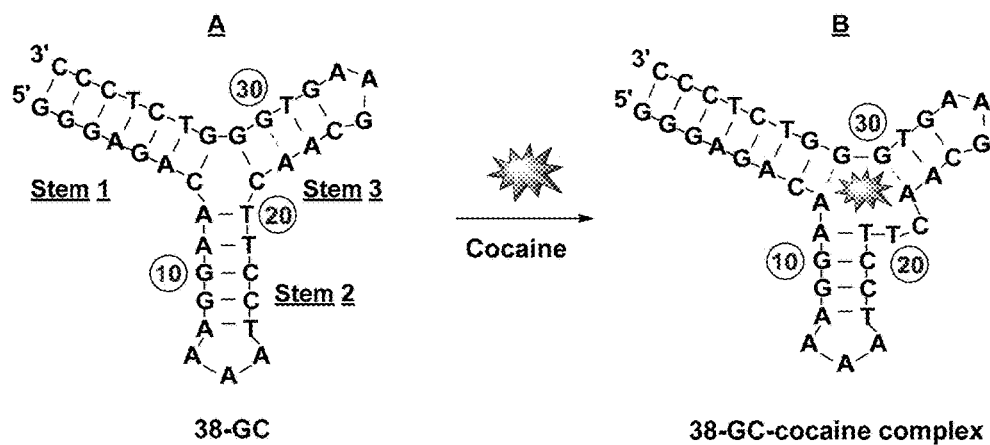
FIGS. 2A-2B show the secondary structure of unbound and cocaine-bound 38-GC. (SEQ ID NO: 2). (2A) 38-GC (2B) undergoes a minor rearrangement of a few nucleotides within its three-way junction upon binding cocaine.

Example 1—Inhibition of Exo III Digestion of a Cocaine-Binding Aptamer Upon Target Binding The binding of small molecules to the grooves of double-stranded DNA can modulate the activity of nucleases. The Exo III-mediated digestion of fully folded aptamers is likewise inhibited by the binding of their small-molecule targets. This is demonstrated using a recently-derived aptamer (38-GC) that binds cocaine with micromolar affinity. 38-GC contains a TWJ-structured binding domain and remains predominantly folded even in the absence of target due to the seven Watson-Crick base-pairs in stem 1 (FIG. 2A). Upon binding cocaine, 38-GC undergoes a minor conformational change, which relocates a few nucleotides within its TWJ binding domain. Specifically, the A8-T20 base-pair in stem 2 and the C21-G31 base-pair in stem 3 are disrupted to form a T20-C21 dinucleotide bulge and an A8-G31 mismatch in the junction (FIG. 2B).

The substrate-recognition site of Exo III is located 1 nm away from its catalytic center. As a result, the activity of Exo III is strongly affected by the structure of DNA three to four bases ahead of its cleavage site. A time-course digestion of 38-GC was performed in the absence and presence of cocaine to investigate whether target binding affects Exo III digestion. The digestion products were characterized by denaturing polyacrylamide gel electrophoresis (PAGE), and their concentrations were calculated relative to a customized DNA ladder loaded in the gel.

Exo III digestion rapidly initiated at stem 1 but stalled 4 bp prior to the binding domain, forming a 35-nt major product regardless of the absence or presence of cocaine. In the absence of cocaine, Exo III continued to non-specifically digest this 35-nt product over time, generating several shorter fragments (FIG. 3A). However, further digestion of the 35-nt product was strongly inhibited in the presence of cocaine. The digestion of 38-GC is initially hindered because the substrate-recognition site of the enzyme is unable to interact with the TWJ structure. This inhibition intensifies when cocaine is bound to the aptamer, which could physically hinder further DNA digestion by the enzyme. After a 35-minute digestion, an 820 nM concentration of 35-nt product was observed in the presence of cocaine, compared with 326 nM without cocaine (FIG. 3B).

Example 2—Effect of TWJ Structure on Exo III Activity

Figures 5A, 5B:
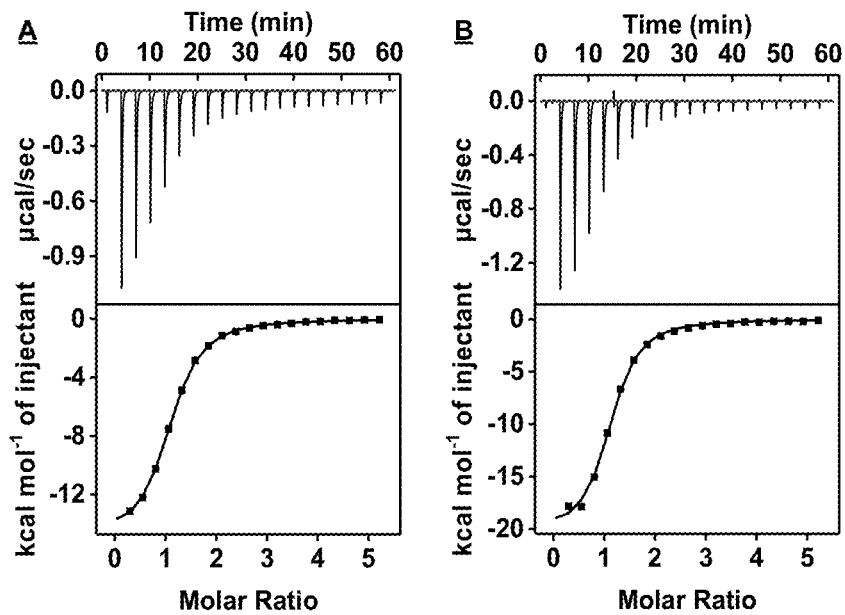
FIGS. 5A-5B show the characterization of target-binding affinity of cocaine-binding aptamers using isothermal titration calorimetry (ITC). Top panels present raw data showing the heat generated from each titration of cocaine for (5A) 38-GC and (5B) 38-GT. Bottom panels show the integrated heat of each titration after correcting for dilution heat of the titrant.
Figures 6A, 6B:
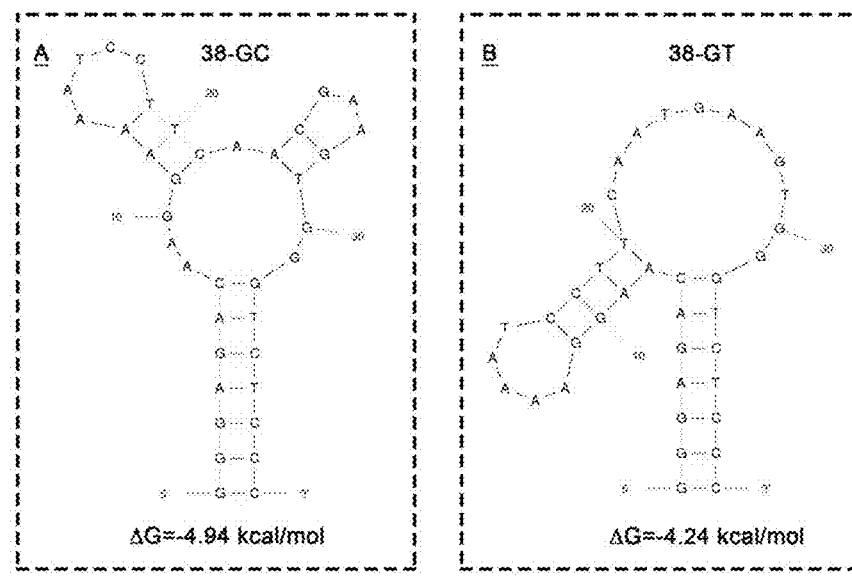
FIGS. 6A-6B show Mfold predicted structures of (6A) 38-GC (SEQ ID NO: 1) and (6B) 38-GT (SEQ ID NO: 2) at 23° C. Free energy values are listed below each structure.
Figure 7A:
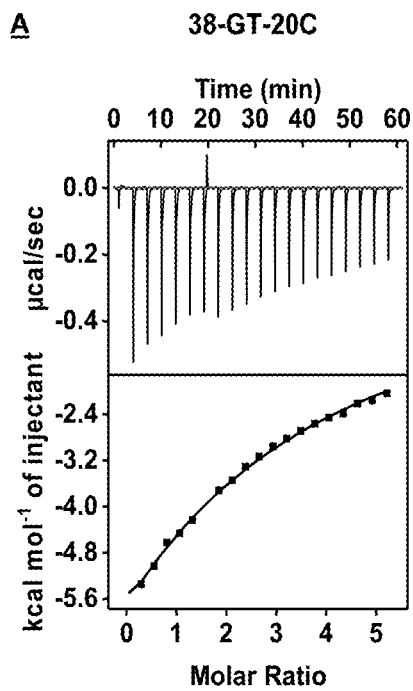
FIGS. 7A-7D show the characterization of cocaine-binding affinity of 38-GT mutants using ITC. Top panels present raw data showing the heat generated from each titration of cocaine for (7A) 38-GT-20C, (7B) 38-GT-20A, (7C) 38-GT-22G and (7D) 38-GT-22T. Bottom panels show the integrated heat of each titration after correcting for dilution heat of the titrant.
Figure 7B:
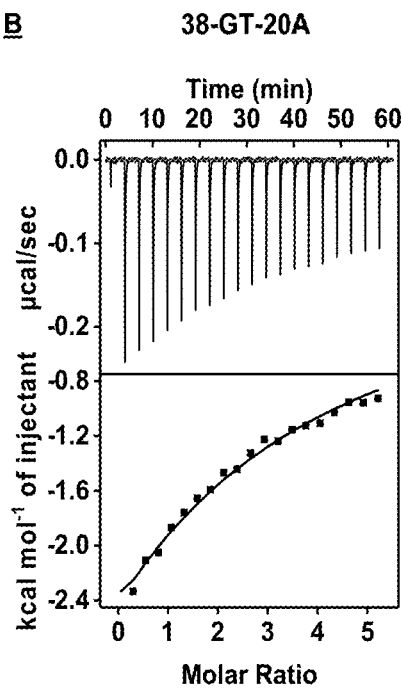
Figure 7C:
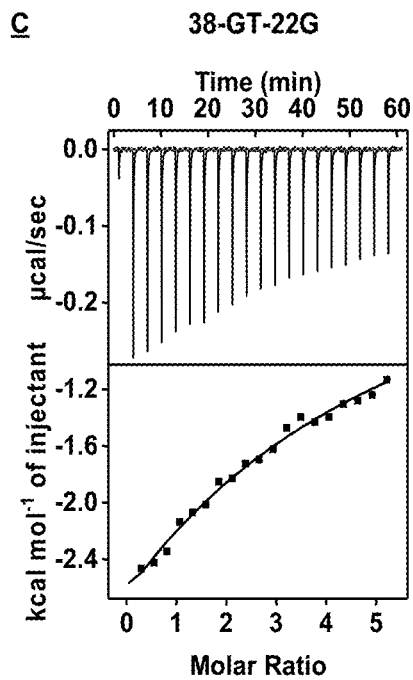
Figure 7D:
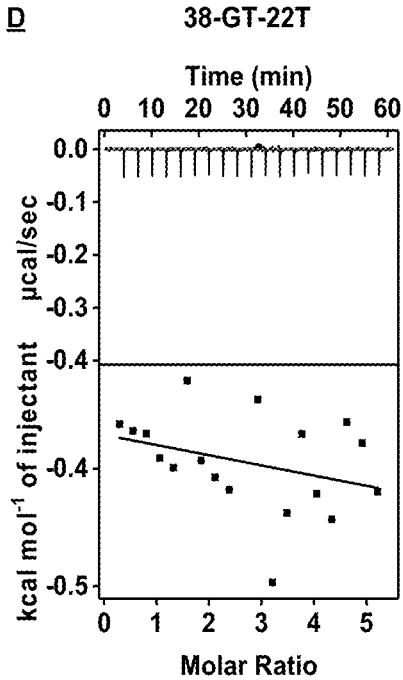

To better elucidate the mechanism of Exo III inhibition, 38-GT, a variant of 38-GC, was engineered, in which the matched C24-G28 base-pair was replaced with a T24-G28 wobble pair (FIG. 4A). Isothermal titration calorimetry (ITC) experiments demonstrated that 38-GT binds to cocaine with a similar affinity ($K_D$=1.6±0.2 µM) to 38-GC ($K_D$=2.0±0.1 µM) under the same experimental conditions (FIG. 5). However, stem 3 of 38-GT is less thermally stable compared to 38-GC, and Mfold predicts that this stem predominantly exists in a single-stranded form under the experimental condition (FIG. 6).

To determine how the TWJ structure affects Exo III digestion, 38-GC and 38-GT were digested under the same experimental conditions with and without cocaine. In the absence of cocaine, 38-GT was completely digested into several short products around 16 nt in length, indicating that the single-stranded stem 3 was digested by Exo III. As expected, high concentrations of Exo III can non-specifically digest single-stranded DNA. In the presence of cocaine, Exo III digestion of 38-GT was effectively inhibited, resulting in the accumulation of a large amount of the 35-nt product (FIGS. 4B and 4C). In addition to directly impeding Exo III's digestion of 38-GT, cocaine binding to the aptamer also shifts equilibrium from a stem-bulge structure to a TWJ structure that is resistant to Exo III digestion (FIG. 4A). After a 25-minute Exo III digestion of 38-GC and 38-GT in the presence of cocaine, 800 nM and 460 nM of the 35-nt product were observed (FIGS. 4B and 4C). This is due to the greater stability of the TWJ in 38-GC compared to 38-GT, which inhibits Exo III digestion even without binding to cocaine.

Example 3—Effect of Mutations within the Binding Domain of 38-GT on Exo III Activity To further confirm that target binding to the aptamer is essential to the inhibition of Exo III digestion, a set of point mutants derived from 38-GT was designed. Two adjacent base-pairs (A8-G31 and A22-G30) and a dinucleotide bulge (T20 and C21) within the binding domain are crucial contributors to the aptamer's binding affinity for cocaine. Mutations at these positions should profoundly alter binding affinity. Four 38-GT mutants were generated, in which the thymine at position 20 was replaced with a cytosine (38-GT-20C) or adenine (38-GT-20A), or the adenine at position 22 was replaced with a guanine (38-GT-22G) or thymine (38-GT-22T). These four point mutants would predominately fold in the absence of cocaine, but with impaired target-binding affinity.

The ITC results confirmed that these mutations prevent cocaine binding (FIG. 7). Exo III digestion of 38-GT and these four mutants were subsequently performed. Compared to the strong cocaine-induced Exo III inhibition observed with 38-GT, only minimal inhibition with 38-GT-22G and 38-GT-22T were observed, and no inhibition at all with 38-GT-20C and 38-GT-20A (FIG. 8). These results confirm that target binding to its aptamer is essential for Exo III inhibition.

To investigate the correlation between inhibition of enzyme digestion and target concentration, Exo III digestion of 38-GT and the mutant 38-GT-20A were performed in the presence of different concentrations of cocaine, ranging from 0 to 2,000 µM (FIG. 9). The extent of Exo III digestion of 38-GT decreased with increasing cocaine concentrations, with 600 nM 35-nt product generated in the presence of 2,000 µM cocaine. In contrast, only a very small amount of 35-nt product (<20 nM) was produced from 38-GT-20C even in the presence of 2,000 µM cocaine, confirming that cocaine itself does not inhibit Exo III digestion. These results demonstrate that the level of Exo III inhibition is target concentration-dependent and clearly correlates with the amount of cocaine-aptamer complex formed.

Example 4—an Exo III-Based, Label-Free Fluorescence Assay for Sensitive Detection of Cocaine with SYBR Green I as a Signal Reporter The fact that Exo III primarily digests unbound rather than target-bound 38-GT was exploited to develop a label-free fluorescence assay with SYBR Green I, a commonly used DNA cyanine dye (FIG. 10A). In the presence of target, Exo III digestion of 38-GT is halted, generating a 35-nt double-stranded product (FIG. 10A, right). SYBR Green I was used to quantify this digestion product, since it preferentially binds double-stranded DNA with 11-fold greater affinity than single-stranded DNA, producing a high-intensity fluorescence signal. In the absence of cocaine, Exo III continues to digest the 35-nt product to yield single-stranded 15-nt and 16-nt products (FIG. 10A, left), which are unable to bind SYBR Green I, resulting in a low background signal. Accordingly, a large, 9-fold signal gain was observed in the presence of 250 µM cocaine using the Exo III-based assay (FIG. 10B).

As a control, the cocaine-induced fluorescence change was monitored for 38-GT without Exo III digestion and only minimal signal gain was observed, most likely due to minor target-induced conformational changes in the aptamer. The sensitivity of the assay was further tested by generating a calibration curve using different concentrations of cocaine. The fluorescence signal increased proportionally to cocaine concentration, with a linear range from 0 to 100 µM ($R^2$=0.9963), and plateaued at 500 µM (FIG. 10C).

The Exo III-based assay produced a 5-fold lower measurable limit of detection (1 µM) than a previously reported Exo I-based fluorescence assay, which can be attributed to the minimal background in the assay. In the Exo III-based assay, the main source of the background signal is eliminated, as non-target-bound aptamers are completely digested into single-stranded products that cannot be labeled by SYBR Green I. In the Exo I assay, some aptamers are folded even in the absence of target, and thus produce high background signal. The Exo III-based assay was subsequently performed for cocaine detection, achieving a measurable limit of detection of 1 µM in 10% saliva (FIG. 11). Thus, the Exo III-based assay is capable of equally sensitive cocaine detection in body fluids.

To confirm that the Exo III-based assay would allow the differentiation between the target and other interferents that may bind to the aptamer, the assay was challenged with three cocaine metabolites—benzoylecgonine (BZE), cocaethylene (EC) and methylecgonidine (MEG)—as well as three structurally dissimilar interferent drugs, diphenhydramine (DPH), nicotine (NIC), and scopolamine (SCP). The assay was not cross-reactive to BZE, MEG, NIC, or SCP (FIG. 12A), which is consistent with ITC data (FIG. 13) showing that 38-GT does not bind to these interferents. Both EC and DPH were confirmed by ITC to bind to 38-GT (FIG. 13) but the assay according to the subject invention was not cross-reactive to DPH and exhibited only 45% cross-reactivity to EC relative to cocaine (FIG. 12A). This was unlike the results from an ATNMD-displacement assay which generated a false positive in presence of DPH (FIG. 12B).

These results highlight the fact that even though 38-GT can bind to several non-target interferents, the Exo III-based assay introduces an additional measure of specificity through the Exo III digestion process.

Example 5—Structure-Switching Functionality Adopted into the Resulting Digestion Product Exo III digestion of 38-GT was inhibited four nucleotides upstream of the target-binding TWJ domain, and it is predicted that the truncated 35-nt aptamer would be thermally destabilized and may possess target-induced structure-switching functionality. To confirm this, a 35-nt product (35-GT) was synthesized and digested using Exo I, a 3'-to-5' exonuclease that specifically digests single-stranded DNA but has no activity towards double-stranded DNA, with or without cocaine. 35-GT was completely digested in the absence of cocaine, indicating that the unbound aptamer is predominately single-stranded. However, digestion of cocaine-bound 35-GT was strongly inhibited, with only 12% of the aptamer digested within 30 minutes (FIG. 14, 35-GT). These results show that 35-GT can effectively fold into a double-stranded TWJ structure upon cocaine binding, suggesting that the aptamer has structure-switching functionality. ITC determined that 35-GT has a binding affinity of $K_D$=12±1.0 µM, (FIG. 15), and thus retains strong target binding affinity. Exo I was also used to perform control experiments with 38-GT and another aptamer variant (31-GT) that was engineered by removing seven nucleotides from the 3' end of 38-GT. Since 38-GT is folded with a blunt-ended stem, Exo I could not digest the duplexed aptamer regardless of the absence or presence of cocaine (FIG. 14, 38-GT). On the other hand, 31-GT predominantly exists in a single-stranded state and was completely digested by Exo I regardless of the absence or presence of target (FIG. 14, 31-GT).

Example 6—Performance of an Electrochemical Aptamer-Based (E-AB) Sensor Fabricated with an Exo III-Truncated Cocaine Aptamer E-AB sensors utilize target-induced conformational changes of structure-switching aptamers to achieve specific detection of various targets. To evaluate the structure-switching functionality of 35-GT, a modified version of the aptamer was used to fabricate an E-AB sensor. Specifically, 35-GT was labeled with a 5' thiol and a 3' methylene blue (MB) redox tag and the modified aptamer was conjugated to a gold electrode surface via thiol-gold chemistry and tested the performance of this E-AB sensor. In the absence of target, the aptamer was primarily unfolded, prohibiting electron transfer from MB to the electrode.

The addition of 100 µM cocaine induced a conformational change of the aptamer that brought MB close to the electrode surface, facilitating efficient electron transfer and resulting in a 170% increase in current within 10 seconds (FIG. 16A). A calibration curve was then constructed for this E-AB sensor using various concentrations of cocaine, and obtained a linear range of 0-100 µM with a detection limit of 1 µM (FIG. 16A). The E-AB sensor was challenged with common interferent drugs (DPH and SCP) and cutting agents (caffeine, levamisole, lidocaine, and sucrose) to test specificity. Notably, the sensor according to the subject invention had low cross-reactivity to DPH (20%) and SCP (10%) and minimal cross-reactivity to all cutting agents (<5%) (FIG. 16C).

These results confirm the structure-switching properties of the Exo III digestion product, and demonstrate the usefulness of such truncated aptamers for sensor applications based on target-induced folding.

Example 7—Generation of a Structure-Switching Aptamer from a Hairpin-Structured ATP-Binding Aptamer The generality of target-binding-induced Exo III inhibition was then demonstrated with a non-TWJ-structured ATP-binding aptamer, ATP-33. ATP-33 forms a hairpin structure with a 7-base-pair blunt-ended stem (FIG. 17), which is a favorable substrate for Exo III but not Exo I. In the absence of ATP, Exo III removed eight nucleotides from the 3'-end of ATP-33, yielding a 25-nt major product. However, the presence of ATP caused Exo III digestion to halt four base-pairs prior to the ATP-binding domain, producing a 30-nt digestion product (FIG. 17, ATP-33 with Exo III). The 30-nt (ATP-30) and 25-nt (ATP-25) digestion products were synthesized, and ITC was used to measure their binding affinity.

Given that ATP-binding aptamers bind to two ATP molecules, the affinity of the first and second ATP binding events were determined using a sequential binding model with two binding sites. The binding affinity of ATP-30 ($K_{D1}$=0.8±0.1 µM and $K_{D2}$=10.1±0.3 µM) was much higher than that of ATP-25 ($K_D$=595±86 µM), and was essentially the same as its parent aptamer, ATP-33 ($K_{D1}$=0.6±0.1 µM and $K_{D2}$=12.3±0.6 µM) (FIG. 18). Negative cooperative binding was observed with ATP-33, which is consistent with a previous study.

To confirm target-binding-induced inhibition, a mutant of ATP-33 (ATP-33-M) was then engineered by changing guanine to adenine at position 12 and adenine to thymine at position 23 (FIG. 19A). ATP-33-M maintains the same secondary structure as ATP-33, but possesses no ATP-binding affinity, as confirmed by ITC (FIG. 19B). Exo III digestion with ATP-33-M was performed and no inhibition was observed in the presence of ATP (FIG. 20), which confirms that target binding is essential for the inhibition of Exo III digestion.

To further determine whether Exo III digestion of other ATP-binding aptamers was inhibited upon binding to ATP, a previously-described structure-switching ATP-binding aptamer (ATP-SW-34) was synthesized. The ATP-SW-34 has been used for both fluorescence and electrochemical detection of ATP. ITC was first used to characterize the binding affinity of ATP-SW-34 under the experimental conditions (10 mM Tris-HCl, 10 mM MgCl$_2$, pH 7.4, 23° C.). The dissociation constants ($K_D$) of the first ($K_{D1}$) and second ($K_{D2}$) binding events for ATP-SW-34 were 21.1±1.3 µM and 7.2±0.3 µM, respectively (FIG. 21). ATP-SW-34 has a lower ATP-binding affinity relative to the pre-folded ATP-33 ($K_{D1}$=0.6±0.1 µM and $K_{D2}$=12.3±0.6 µM). This was expected, since the target-binding domain of ATP-SW-34 is purposely destabilized to achieve target-induced structure switching. A slight positive cooperativity was also observed with ATP-SW-34, possibly because binding of the first ATP molecule induces a conformational change in the aptamer, which greatly facilitates binding of the second ATP molecule.

Exo III digestion of ATP-SW-34 was then performed in the experimental conditions (10 mM Tris buffer (pH 7.4) including 10 mM MgCl$_2$, 1 µM DNA, 0.05 U/µL Exo III, 250 µM ATP, at 23° C.). ATP-SW-34 was completely digested to products shorter than 25 nt in length in the absence of ATP within 10 minutes. However, in the presence of 250 µM ATP, Exo III was halted four nucleotides prior to the target-binding domain to generate a 33-nt major product ATP-SW-33 (SEQ ID NO: 41)(FIGS. 22A and 22B). Even after 60 minutes of digestion, the 33-nt product was still present (FIG. 22C). As a comparison, Exo III digestion of ATP-SW-34 was also performed under the literature-reported experimental conditions (10 mM Tris buffer (pH 7.9) including 50 mM NaCl, 10 mM MgCl$_2$, 2 µM DNA, 2 U/µL Exo III, 250 µM ATP, at 37° C.). Exo III digests much faster under these conditions regardless of the presence or absence of ATP, most likely due to the higher concentration of Exo III and higher temperature. Specifically, ATP-SW-34 was completely digested into products around 25 nt in length, ATP-SW-25 (SEQ ID NO: 42), within 10 seconds in the absence of ATP, whereas the 33-nt product, ATP-SW-33 (SEQ ID NO: 41), was detectable for up to 60 seconds in the presence of ATP (FIGS. 23A and 23B). The aptamer was completely digested into products less than 25 nt in length after 3 minutes regardless of the presence or absence of ATP (FIG. 23C). This weaker inhibition of Exo III in the literature-reported conditions is likely attributable to the lower ATP-binding affinity of the aptamer at elevated temperatures. Thus, this Exo III inhibition phenomenon is generalizable for other target-bound small-molecule-binding aptamers with different secondary structures, such as stem-loop.

To confirm that ATP-30 had structure-switching functionality, ATP-33, ATP-30, and ATP-25 were digested with Exo I in the presence and absence of ATP (FIG. 17, Exo I). As expected, Exo I completely digested ATP-30 in the absence of target but was unable to digest the aptamer in the presence of target. This result indicated that ATP-30 has target-induced structure-switching functionality. On the other hand, no digestion of ATP-33 was observed regardless of the presence or absence of ATP due to its fully folded stem-loop structure. ATP-25 was completely digested by Exo I regardless of the presence or absence of target, confirming that this aptamer exists in a single-stranded state.

The structure-switching functionality of ATP-30 was then exploited to fabricate a fluorophore-quencher ATP sensor. ATP-30 was labeled with a 3' Cy5 fluorophore and a 5' IowaBlack quencher (ATP-30-FQ). In the absence of target, the aptamer is primarily unfolded and the fluorophore is separated from the quencher, producing a large fluorescence background (FIG. 24A). The addition of 100 µM ATP induces a conformational change in the aptamer that brings the fluorophore in close proximity to the quencher, yielding a strong reduction in fluorescence within seconds (FIG. 24B). This sensor was challenged with various concentrations of ATP, and obtained a linear range of 0-10 µM with a measurable detection limit of 2.5 µM (FIG. 24C).

Thus, Exo III digestion of target-bound aptamers offers an apparently generalizable means for introducing structure-switching functionality.

Example 8—Structure Selectivity of Exo III on Target-Aptamer Complex

The 3'-to-5' exonuclease activity of Exo III on double-stranded DNA can be stalled by covalent and non-covalent DNA-binding small molecules. For example, benzo-α-pyrene and benzo-c-phenanthrene react with the primary amine group of deoxyadenosine and deoxyguanosine bases, forming covalent DNA adducts. These covalently conjugated molecules bind within the helical minor-groove and halt Exo III digestion three to four bases prior to the binding site. Similar behavior has been observed with non-covalent DNA-binding small molecules, such as DAPI, Hoechst 33258, and distamycin A, which inhibit Exo III digestion three to six bases prior to the binding site. Exo III activity is similarly affected by aptamer-target interactions.

Exo III digestion was performed using a previously-isolated DIS-binding aptamer (DIS-37). DIS-37 exists in a fully-folded state even in the absence of DIS, due to the seven Watson-Crick base-pairs in stem 1 (FIG. 25A). DIS binds within the aptamer's pre-folded three-way junction target-binding domain without inducing a large conformational change in the aptamer. A time-course of DIS-37 Exo III digestion was performed in the presence and absence of DIS and the digestion products were characterized using denaturing PAGE, with concentrations calculated relative to a customized DNA ladder loaded in the gel. Regardless of the presence or absence of DIS, Exo III rapidly removed the first three nucleotides from the 3' end of DIS-37. In the absence of DIS, Exo III continued digestion, forming three intermediate products (33-, 32-, and 31-nt) and eventually resulting in a 30-nt major product (FIG. 25B). In the presence of DIS, further Exo III digestion was greatly inhibited, resulting in a large amount of 33- and 34-nt major products after a 20-min reaction (FIGS. 25B and 25C). These results demonstrate that Exo III digestion of DIS-37 is significantly inhibited upon the addition of target.

The 30-, 33-, and 34-nt major products (DIS-30, DIS-33, DIS-34) were synthesized and ITC was used to investigate the binding affinity of these oligonucleotides to DIS. An equilibrium dissociation constant ($K_D$) of 4.0±0.2 µM for DIS-34 was obtained (FIG. 26A), which is very similar to the $K_D$ of DIS-37 (3.4±0.2 µM, FIG. 26B). A 4-fold decrease in binding affinity was observed for DIS-33 ($K_D$=16.0±1.0 µM, FIG. 26C) due to its reduced thermostability.

These results indicate that the major products generated in the presence of DIS remain bound to the target. In contrast, DIS-30 resists Exo III digestion, but retains no binding affinity for DIS (FIG. 26D), indicating this product presumably exists in a single-stranded state.

Example 9—Inhibition of Exo III Requires Formation of the Target-Aptamer Complex To confirm that Exo III digestion of DIS-37 is modulated specifically by target binding, a mutant aptamer was designed with no binding affinity for DIS. This mutant (DIS-37-M) was designed by changing two nucleotides within the target binding domain, specifically the adenine at position 21 and the thymine at position 30 were both changed to cytosine (FIG. 27A). DIS-37-M would retain a three-way junction structure in the absence of DIS, but with impaired target-binding affinity. ITC confirmed that DIS-37-M possesses greatly reduced binding affinity for DIS ($K_D$>1000 µM, FIG. 27B).

In order to verify that the aptamer is fully folded, Exo I, which is able to digest single-stranded but not double-stranded DNA, was used. Both DIS-37 and DIS-37-M were incubated with Exo I, which was unable to digest either aptamer regardless of the presence or absence of DIS (FIG. 28). This indicated that stem 1 was fully folded in both aptamers. To evaluate whether the target itself inhibits Exo III activity, Exo III digestion was performed with DIS-37-M. Results show that Exo III digestion of DIS-37-M yielded the same major products (32-, 31-, and 30-nt) regardless of the presence or absence of DIS (FIG. 28A). Given that the DIS-37-M cannot form the aptamer-target complex, this clearly indicates that DIS itself does not impair the activity of Exo III.

The same experiment was performed with DIS-37. Results show that DIS-binding inhibited Exo III digestion of DIS-37 whereas the aptamer alone was readily digested by the enzyme (FIG. 28B). These results demonstrate that the formation of the target-aptamer complex is directly responsible for inhibiting Exo III digestion.

Example 10—Mechanism of Exo III Inhibition and Development of the Exonuclease-Inhibition Assay Exo III digestion of DIS-37 occurred via a two-phase process. First, Exo III rapidly catalyzed the digestion of the double-stranded 3' end of DIS-37, removing three nucleotides to form a 34-nt product regardless of the presence or absence of DIS. In the absence of target, Exo III continued to digest the 34-nt product into 33-, 32-, and 31-nt products at a progressively slower rate, eventually resulting in a 30-nt major product (FIG. 25B). In the presence of target, the 34-nt target-bound product greatly inhibited Exo III digestion. To understand the mechanism of Exo III inhibition, the 30-nt and 34-nt products (DIS-30 and DIS-34) were synthesized, and the digestion of DIS-30 and DIS-34 were performed with Exo III or Exo I. Regardless of the presence or absence of target, DIS-30 was not digested by Exo III, but was completely digested by Exo I (FIG. 29A). This indicates that the 30-nt product predominantly exists in a single-stranded state, even in the presence of 500 µM of DIS. Meanwhile, both Exo III and Exo I could digest DIS-34 in the absence of target (FIG. 29B), indicating that non-target-bound DIS-34 is in equilibrium between single-stranded and double-stranded states. Specifically, Exo III digestion progressively generated three intermediate products (33-, 32- and 31-nt) and eventually resulted in a 30-nt major product (FIG. 29B). In contrast, Exo III digestion of DIS-34 was significantly inhibited in the presence of DIS due to the formation of the target-aptamer complex. Similarly, target-bound DIS-34 was not digested by Exo I, indicating that the aptamer was primarily in a double-stranded state when bound to DIS (FIG. 29B).

Based on these results, an exonuclease-inhibition assay was developed to utilize the synergistic digestion of both Exo III and Exo I to quantify DIS concentrations. Unbound DIS-37 would first be digested by Exo III to form several products that are in equilibrium between single-stranded and double-stranded states, which can be completely digested by both exonucleases. In contrast, in the presence of DIS, Exo III will remove only three nucleotides from DIS-37, with the resulting target-bound double-stranded 34-nt product remaining resistant to digestion by both exonucleases.

As a demonstration, digestion of DIS-37 was performed using the exonuclease mixture and the digestion products were analyzed with PAGE. In the absence of target, DIS-37 was completely digested. In the presence of target, a 34-nt major product was observed and the concentration of this product increased with increasing concentrations of DIS until reaching saturation at 250 µM DIS (FIGS. 30A and 30C). In order to determine whether higher concentrations of DIS might inhibit the exonucleases' activity, the mutant aptamer, DIS-37-M, was digested, with the exonuclease mixture. The mutant was completely digested at DIS concentrations up to 500 µM (FIGS. 30B and 30C). It is clear that DIS itself inhibits neither Exo III nor Exo I.

Example 11—Label-Free Detection of DIS Using an Exonuclease-Inhibition Fluorescence Assay Using SYBR Gold as a Signal Reporter The exonuclease-inhibition approach was adapted into a label-free fluorescence assay for the rapid and sensitive detection of DIS via the quantification of aptamer digestion products (FIG. 31A). DIS-37 aptamers yielded intact oligonucleotide products in the presence of DIS, whereas the aptamer was completely degraded into mononucleotides in the absence of DIS (FIG. 31A). Therefore, SYBR Gold was selected as a signal reporter since it fluorescently stains only oligonucleotides but not mononucleotides. Following a 15-min digestion of DJS-37 by the exonuclease mixture, a solution containing EDTA and formamide was added to deactivate the exonucleases and denature all major products into single-stranded structures. After adding 1×SYBR Gold into the samples, a 40-fold signal gain was observed for a sample containing 250 µM DIS relative to the target-free sample, with only minimal background signal in the absence of DIS (FIG. 31B).

As a control, DIS-37 and SYBR Gold was used to monitor target-induced fluorescence changes without exonuclease treatment, and virtually no difference was observed in fluorescence intensity upon the addition of 250 µM DIS (FIG. 31B). The target sensitivity of the assay was further measured by generating a fluorescence calibration curve using different concentrations of DIS (FIG. 31C). The fluorescence signal gain increased as the DIS concentration increased (FIG. 31C), with a linear range from 0 to 10 µM ($R^2=0.9996$) and a measurable detection limit of 0.5 µM (FIG. 31C).

Importantly, the exonuclease-inhibition assay demonstrated robust performance in biological matrices, and a similar linear range and detection limit was obtained for DIS detection in 50% urine samples (FIG. 32).

Figure 34A:
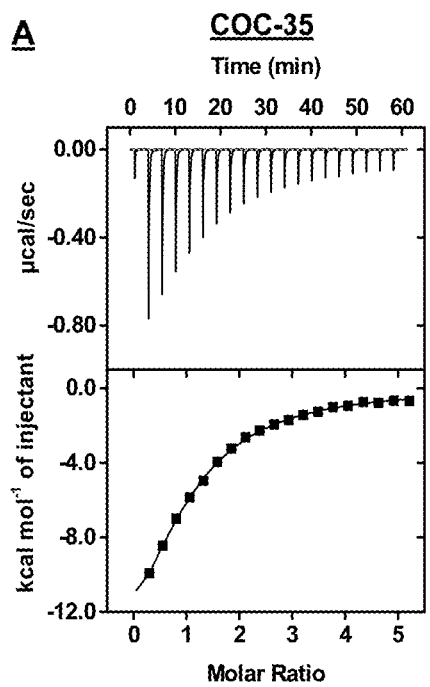
Figure 34B:
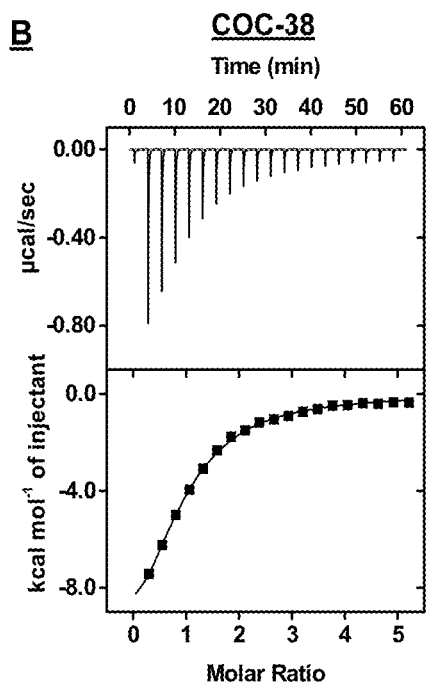
Figure 34C:
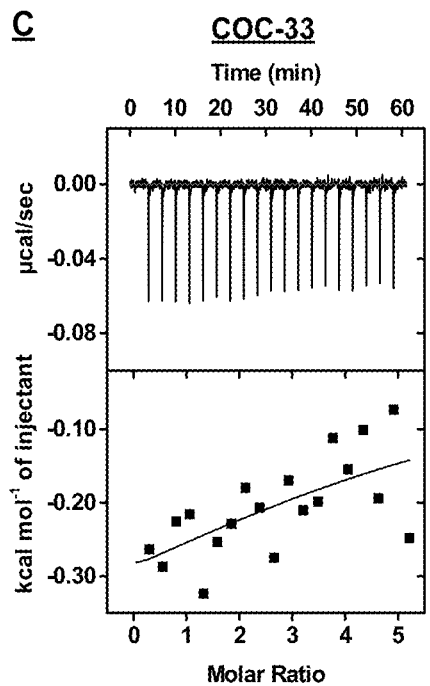

Example 12—Generalization of the Exonuclease-Inhibition Assay with a Three-Way-Junction Cocaine Aptamer To demonstrate the generality of the exonuclease-inhibition assay, a cocaine-binding aptamer (COC-38) was selected, which is pre-folded and contains a three-way junction binding domain like DIS-37. COC-38 contains a 7-base-pair blunt-ended stem and is a preferred substrate for Exo III. COC-38 was incubated with Exo I, Exo III, or the exonuclease mixture in the absence and presence of cocaine, and the digestion products were characterized using PAGE (FIG. 33A). Exo I alone did not digest the fully-folded aptamer regardless of the presence of cocaine (FIG. 33A, Exo I), whereas Exo III showed a target-dependent digestion profile (FIG. 33A, Exo III). A 33-nt major product was observed in the absence of target, which is single-stranded due to the destabilization of stem 1. In the presence of cocaine, only three nucleotides were removed from COC-38 to form a 35-nt product, and further digestion was strongly inhibited (FIG. 33B). As with DIS-34, this 35-nt product is presumably capable of retaining the target, thus remaining folded. ITC experiments confirmed that the 35-nt product (COC-35) binds to cocaine ($K_D=16.9\pm0.7$ µM) (FIG. 34A) with a similar affinity as COC-38 ($K_D=11.2\pm0.6$ µM) (FIG. 34B), whereas the 33-nt product has no affinity for cocaine (FIG. 34C). Similar to DIS-37, non-target-bound COC-38 was completely digested by the exonuclease mixture, but both enzymes were strongly inhibited by the target-bound 35-nt product (FIG. 33A, Exo M).

Figure 34D:
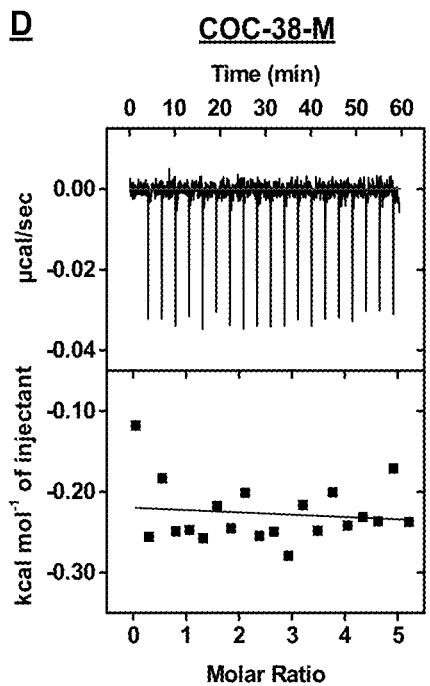

To confirm that enzymatic inhibition was specifically associated with formation of the target-aptamer complex, exonuclease digestion was performed with a COC-38 mutant (COC-38-M) containing a single adenine-to-guanine mutation at position 22 that eliminates its binding affinity for cocaine (FIG. 34D). COC-38-M was resistant to Exo I digestion, indicating that it retains the same pre-folded structure as COC-38 (FIG. 33C). The Exo III and exonuclease mixture (Exo M) digestion profiles of COC-38-M were identical regardless of the presence or absence of cocaine (FIG. 33C), showing that target-binding is crucial for exonuclease inhibition. The concentration of the major product of COC-38 increased with increasing concentrations of cocaine when the exonuclease mixture was used (FIG. 35). When the exonuclease-inhibition fluorescence assay was replicated for the detection of cocaine, a linear range was obtained from 0-10 µM ($R^2=0.9991$) with a measurable detection limit of 0.1 µM in both buffer (FIG. 36) and 10% saliva (FIG. 37).

Example 13—Generalization of the Dual-Exonuclease Assay with a Hairpin-Structured ATP Aptamer The generality of the exonuclease-inhibition assay was further demonstrated using an ATP-binding aptamer (ATP-33). ATP-33 is fully-folded, and forms a hairpin structure with a 7-base-pair blunt-ended stem that is resistant to Exo I digestion (FIG. 38A, Exo I). Despite its structural difference relative to both DIS-37 and COC-38, ATP-33 also exhibits a target binding-dependent Exo III digestion profile. Exo III digestion produced a single-stranded 25-nt major product in the absence of ATP and a 30-nt product in the presence of ATP (FIGS. 38A, Exo III and 38B). The ATP-binding affinity of the 25-nt (ATP-25) and 30-nt (ATP-30) major products were measured using ITC, and result shows that the binding affinity of ATP-30 ($K_{1/2}=2.8\pm0.1$ µM, FIG. 39A) was much higher than that of ATP-25 ($K_D=595\pm86$ µM, FIG. 39B). As with the other two aptamers, the major product of Exo III digestion from target-bound ATP-33 essentially retains the affinity of the undigested aptamer ($K_{1/2}=2.8\pm0.1$ µM, FIG. 39C). A target-dependent digestion profile was also observed with the exonuclease mixture (FIG. 38A, Exo M). To confirm that enzymatic inhibition is specifically due to ATP-binding to the aptamer, an aptamer mutant (ATP-33-M) was engineered by changing guanine to adenine at position 12 and adenine to thymine at position 23 (FIG. 38C). ATP-33-M possesses no binding affinity (FIG. 39D), but maintains the same secondary structure as ATP-33, which was confirmed by the inhibition of Exo I digestion (FIG. 38B, Exo I). As expected, the Exo III and exonuclease mixture (Exo M) digestion profiles of ATP-33-M were identical regardless of the presence or absence of ATP (FIG. 38C), whereas the concentration of the major 30-nt product increased with increasing concentrations of ATP (FIG. 40). Finally, the exonuclease-inhibition fluorescence assay was carried out using ATP-33, and achieved a linear range from 0-10 µM ($R^2=0.9991$) with a detection limit of 0.25 µM (FIG. 41). These results clearly demonstrated the generality of the exonuclease-inhibition assay on aptamers with different secondary structures.

Example 14—Multiplex Detection of Cocaine and ATP Using Fluorophore-Quencher Modified Molecular Beacons Multiplex detection is a highly valuable and vital tool for medical diagnostics, drug screening, and food safety as it enables detection of a multitude of analytes with only a single low-volume sample. The exonuclease-inhibition assay can be easily expanded for multiplex detection, since the nucleotide sequences of the digestion products are known and unique for each aptamer-target pair. These aptamer digestion products serve as proxies for each individual target and can be quantified using molecular beacons that are designed to specifically hybridize with an individual digested aptamer strand. The resulting signal can be used to accurately determine the concentration of the target.

As a demonstration, the exonuclease-inhibition assay was employed with two fluorophore-quencher modified molecular beacons to simultaneously detect ATP and cocaine. The design of molecular beacons is very simple, as they share the same six base-pair stem but with different complementary loop regions. The molecular beacon for ATP (ATP-MB) contains a 28-nt loop that is complementary to ATP-30 and is modified with a 5' Cy5 and 3' Iowa Black RQ quencher while the molecular beacon for cocaine (COC-MB) contains a 33-nt loop that is complementary to COC-35 and is modified with a 5' FAM and a 3' Black Hole Quencher 1 (FIG. 42).

To perform the multiplex assay, a mixture of aptamers (ATP-33 and COC-38) is digested using both Exo III and Exo I followed by the addition of a mixture of fluorophore-quencher-modified molecular beacons. In the absence of target, both exonucleases completely digest all aptamers. Upon addition of the molecular beacons, no fluorescence is generated as the beacons exist in a closed state, where the fluorophore is in close proximity to the quencher (FIG. 43, no target). However, in the presence of either or both target, the exonucleases will generate specific aptamer digestion products which hybridize with their corresponding molecular beacon(s), separating the fluorophore from the quencher and generating a single (FIG. 43, cocaine or ATP) or dual (FIG. 43, ATP and cocaine) fluorescence signal.

The performance of the exonuclease-inhibition assay was determined for multiplex detection of ATP and cocaine. Specifically, a mixture of aptamers (ATP-33 and COC-38) was digested using the exonuclease mixture with no, either, or both ATP and cocaine (FIG. 44). After 20 minutes, EDTA was added to stop digestion and then a mixture of beacons (ATP-MB and COC-MB) was added to determine target concentrations through quantification of the aptamer digestion products. In the absence of either target, no fluorescence signal was observed. In the presence of 25 or 100 µM cocaine alone, a concentration-dependent fluorescence signal was observed at 520 nm (FAM) generated by COC-MB whereas ATP-MB produced no signal at 668 nm (Cy5). A concentration-dependent fluorescence signal at 668 nm was obtained for ATP and no cross-talk was observed between the two beacons. In the presence of a binary mixture of both targets at various concentrations, distinct fluorescence signals at both 520 and 668 nm were observed which corresponded to the presence of cocaine and ATP, respectively.

Notably, the presence of one target did not affect the fluorescence intensity of the other as the fluorescence signal generated in the presence of cocaine and ATP were identical regardless of whether both targets were present in a mixture or alone. These results demonstrated the capability of the exonuclease-inhibition assay for the simultaneous detection of multiple small molecules.

Example 15—Design of Aptamers with Structure-Switching Functionality for the Detection of Synthetic Cathinones SCA1.1 and SCA2.1 (Table 1) are both 46-nt fully-folded stem-loop-structured aptamers that lack structure-switching functionality. Exo III is a 3'-to-5' exonuclease that digests aptamers with duplexed ends into single-stranded products in the absence of target. For target-bound aptamers, this digestion is halted a few bases prior to the target-binding domain, resulting in truncated aptamers with structure-switching functionality.

After 6 hours of Exo III digestion, both of these 46-nt aptamers were digested into 40-nt major products in the presence of target. In the absence of target, these aptamers were more heavily degraded. However, this digestion was incomplete, possibly due to the low activity of Exo III on single-stranded DNA. To remedy this problem, Exo III was combined with exonuclease I (Exo I), a single-strand 3'-to-5' exonuclease, to perform aptamer digestion. Using this mixture, both aptamers were completely digested in the absence of target, whereas 40-nt major products were retained in the presence of target.

To confirm that the truncated aptamers had structure-switching functionality, the 40-nt products (SCA1.1-40 and SCA2.1-40; Table 1) were synthesized and digested with Exo I. Both aptamers were completely digested within 2 hours in the absence of target, indicating that they are single-stranded. In contrast, 89% and 92% of SCA1.1-40 and SCA2.1-40 respectively remained intact in the presence of target due to the formation of a folded target-aptamer complex that resisted Exo I digestion.

The structure-switching functionality of these two truncated aptamers was further confirmed by a dramatic change of their circular dichroism spectra upon the addition of MDPV. Isothermal titration calorimetry experiments were then performed to determine the target-binding affinity of the truncated aptamers to both enantiomers of MDPV, (+)-MDPV and (−)-MDPV, as synthetic cathinones are chiral molecules. SCA2.1-40 binds to (−)-MDPV much more strongly than to (+)-MDPV, with equilibrium dissociation constants ($K_D$) of 650±3 nM and 292±14 µM, respectively. SCA1.1-40 exhibits a similar pattern of binding strongly to (−)-MDPV, with a $K_D$ of 1.05±0.05 µM, but only weak affinity for (+)-MDPV, with a $K_D$ of 181±2 µM. This weaker affinity for (+)-MDPV should not be of concern for analytical purposes, as synthetic cathinones always exist as racemic mixtures. Therefore, SCA2.1-40 and SCA1.1-40 are suitable for fabricating E-AB sensors due to their structure-switching functionality and high affinity.

SCA2.1-40 and SCA1.1-40 have 6-nt overhangs at the 5' terminus that do not contribute to target binding and can potentially reduce the electron transfer rate. Therefore, these overhangs were removed and the aptamers were modified with a thiol group at their 5' end and a methylene blue (MB) redox tag at their 3' end to generate SCA2.1-34-MB and SCA1.1-34-MB.

TABLE 1

The sequences of DNA aptamers

| Sequence | Sequence (5'-3') | SEQ ID No. |
|---|---|---|
| SCA2.1 | CTTACGACCTTAAGTGGGGTTCGGGTGGAGTTTATGGGGTCGTAAG | 35 |
| SCA2.1-40 | CTTACGACCTTAAGTGGGGTTCGGGTGGAGTTTATGGGGT | 36 |
| SCA1.1 | CTTACGACTGAGAAGTGTGATTCAGTATGTTTTCCGAAGTCGTAAG | 37 |
| SCA1.1-40 | CTTACGACTGAGAAGTGTGATTCAGTATGTTTTCCGAAGT | 38 |
| SCA-2.1-34-MB | SH-C6-ACCTTAAGTGGGGTTCGGGTGGAGTTTATGGGGT-MB | 39 |
| SCA-1.1-34-MB | SH-C6-CTTACGACTGAGAAGTGTGATTCAGTATGTTTTC-MB | 40 |

SH = thiol modification; MB = methylene blue modification; C6 = $(CH_2)_6$ linker

Example 16—E-AB Sensor for the Detection of Synthetic Cathinones

An E-AB sensor was synthesized using the truncated aptamers. E-AB sensors were first fabricated E-AB sensors using either aptamer alone. Both sensors produced increasing current with increasing concentrations of target, with linear ranges of 0-1 µM and limits of detection of 100 nM for MDPV (FIGS. 45A-B and 46A-B). The sensors were then challenged with 12 synthetic cathinones at a concentration of 10 µM and 15 interferents at 100 µM. The SCA2.1-based sensor showed cross-reactivity >50% for 8 of the 12 targets and strong discrimination against all 15 interferents, with ≤18% cross-reactivity (FIG. 45C). In contrast, the SCA1.1-based sensor responded to all 12 synthetic cathinones with cross-reactivity >50%, but exhibited poor specificity towards some interferents, particularly MDMA, levamisole, and quinine with cross-reactivity ranging from 36%-63% (FIG. 46C).

To develop an E-AB sensor with a near-ideal target-binding profile, an E-AB sensor was fabricated with a mixture of SCA1.1-34-MB and SCA2.1-34-MB (FIG. 47A). Given that the modification efficiency of SCA1.1-34-MB was slightly higher than that of SCA2.1-34-MB (FIG. 48), an initial aptamer ratio of 5:6 (SCA1.1-34-MB:SCA2.1-34-MB) was used to achieve an approximate surface density ratio of 1:1.

The dual-aptamer-modified E-AB sensor had a limit of detection of 50 nM for MDPV, with a linear range of 0-0.5 µM (FIG. 47B), slightly better than the E-AB sensors fabricated with either aptamer alone. As expected, the dual-aptamer-modified electrode exhibited high cross-reactivity (>50%) to all 12 synthetic cathinones at a concentration of 10 µM while having excellent specificity (≤20% cross-reactivity) against all tested interferents at 100 µM (FIG. 47C).

These results confirm that the dual-aptamer-modified E-AB sensor is amenable for synthetic cathinone detection in interferent-ridden samples. To demonstrate this, the sensor was challenged with 15 binary mixtures of 10 µM MDPV with 100 µM interferent. The sensor yielded similar responses to all binary mixtures relative to MDPV alone, except for mixtures containing MDMA or quinine, which displayed slight signal suppression (FIG. 49). This can be most likely attributed to the interferents competing with the target to bind to a fixed number of electrode-bound aptamers as they have moderate affinity, and such binding possibly does not induce the same conformational change as synthetic cathinones like MDPV.

What is claimed is:

1. An aptamer-based sensor comprising SCA-1.1-34-MB (SEQ ID NO: 40).

2. The aptamer-based sensor of claim 1, which is an electrochemical aptamer-based (E-AB) sensor.

3. The aptamer-based sensor of claim 1, comprising an electrode.

4. The aptamer-based sensor of claim 3, the electrode being functionalized by SCA-1.1-34-MB (SEQ ID NO: 40).

5. The aptamer-based sensor of claim 3, the electrode being made of gold, silver, or platinum.

6. A method for detecting a cathinone in a sample comprising the steps of:
   contacting the sample with the aptamer-based sensor of claim 1; and
   detecting the cathinone in the sample, the detection comprising measuring a signal generated upon binding of the cathinone with the aptamer-based sensor.

7. The method according to claim 6, the sample being a biological sample or an environmental sample.

8. The method according to claim 7, the biological sample being selected from blood, plasma, urine, tears, and saliva.

9. The method according to claim 6, the method further comprising determining the concentration of the cathinone in the sample.

10. The method according to claim 6, the signal being an increase in current.

11. An aptamer-based sensor comprising SCA-2.1-34-MB (SEQ ID NO: 39) and SCA-1.1-34-MB (SEQ ID NO: 40).

12. The aptamer-based sensor of claim 11, which is an electrochemical aptamer-based (E-AB) sensor.

13. The aptamer-based sensor of claim 11, comprising an electrode.

14. The aptamer-based sensor of claim 13, the electrode being surface-functionalized by SCA-2.1-34-MB (SEQ ID NO: 39) and SCA-1.1-34-MB (SEQ ID NO: 40).

15. The aptamer-based sensor of claim 13, the electrode being made of gold, silver, or platinum.

16. A method for detecting a cathinone in a sample comprising the steps of:
contacting the sample with the aptamer-based sensor of claim 11; and
detecting the cathinone in the sample, the detection comprising measuring a signal generated upon binding of the cathinone with the aptamer-based sensor.

17. The method according to claim 16, the sample being a biological sample or an environmental sample.

18. The method according to claim 17, the biological sample being selected from blood, plasma, urine, tears, and saliva.

19. The method according to claim 16, the method further comprising determining the concentration of the cathinone in the sample.

20. The method according to claim 16, the signal being an increase in current.

\* \* \* \* \*

SEQUENCE LISTING

```
<160> NUMBER OF SEQ ID NOS: 42

<210> SEQ ID NO 1
<211> LENGTH: 38
<212> TYPE: DNA
<213> ORGANISM: Artificial sequence
<220> FEATURE:
<223> OTHER INFORMATION: aptamer

<400> SEQUENCE: 1
gggagacaag gaaaatcctt caacgaagtg ggtctccc                    38

<210> SEQ ID NO 2
<211> LENGTH: 38
<212> TYPE: DNA
<213> ORGANISM: Artificial sequence
<220> FEATURE:
<223> OTHER INFORMATION: aptamer

<400> SEQUENCE: 2
gggagacaag gaaaatcctt caatgaagtg ggtctccc                    38
```

<210> SEQ ID NO 3
<211> LENGTH: 35
<212> TYPE: DNA
<213> ORGANISM: Artificial sequence
<220> FEATURE:
<223> OTHER INFORMATION: aptamer

<400> SEQUENCE: 3
gggagacaag gaaaatcctt caatgaagtg ggtct         35

<210> SEQ ID NO 4
<211> LENGTH: 31
<212> TYPE: DNA
<213> ORGANISM: Artificial sequence
<220> FEATURE:
<223> OTHER INFORMATION: aptamer

<400> SEQUENCE: 4
gggagacaag gaaaatcctt caatgaagtg g             31

<210> SEQ ID NO 5
<211> LENGTH: 38
<212> TYPE: DNA
<213> ORGANISM: Artificial sequence
<220> FEATURE:
<223> OTHER INFORMATION: aptamer

<400> SEQUENCE: 5
gggagacaag gaaaatcctc caatgaagtg ggtctccc      38

<210> SEQ ID NO 6
<211> LENGTH: 38
<212> TYPE: DNA
<213> ORGANISM: Artificial sequence
<220> FEATURE:
<223> OTHER INFORMATION: aptamer

<400> SEQUENCE: 6
gggagacaag gaaaatccta caatgaagtg ggtctccc      38

<210> SEQ ID NO 7
<211> LENGTH: 38
<212> TYPE: DNA
<213> ORGANISM: Artificial sequence
<220> FEATURE:
<223> OTHER INFORMATION: aptamer

<400> SEQUENCE: 7
gggagacaag gaaaatcctt cgatgaagtg ggtctccc      38

<210> SEQ ID NO 8
<211> LENGTH: 38
<212> TYPE: DNA
<213> ORGANISM: Artificial sequence
<220> FEATURE:
<223> OTHER INFORMATION: aptamer

<400> SEQUENCE: 8
gggagacaag gaaaatcctt ctatgaagtg ggtctccc      38

<210> SEQ ID NO 9
<211> LENGTH: 32
<212> TYPE: DNA
<213> ORGANISM: Artificial sequence
<220> FEATURE:

```
<223> OTHER INFORMATION: aptamer

<400> SEQUENCE: 9
agacaaggaa aatccttcaa tgaagtgggt ct                          32

<210> SEQ ID NO 10
<211> LENGTH: 33
<212> TYPE: DNA
<213> ORGANISM: Artificial sequence
<220> FEATURE:
<223> OTHER INFORMATION: aptamer

<400> SEQUENCE: 10
cgcacctggg ggagtattgc ggaggaaggt gcg                         33

<210> SEQ ID NO 11
<211> LENGTH: 30
<212> TYPE: DNA
<213> ORGANISM: Artificial sequence
<220> FEATURE:
<223> OTHER INFORMATION: aptamer

<400> SEQUENCE: 11
cgcacctggg ggagtattgc ggaggaaggt                             30

<210> SEQ ID NO 12
<211> LENGTH: 25
<212> TYPE: DNA
<213> ORGANISM: Artificial sequence
<220> FEATURE:
<223> OTHER INFORMATION: aptamer

<400> SEQUENCE: 12
cgcacctggg ggagtattgc ggagg                                  25

<210> SEQ ID NO 13
<211> LENGTH: 30
<212> TYPE: DNA
<213> ORGANISM: Artificial sequence
<220> FEATURE:
<223> OTHER INFORMATION: aptamer
<220> FEATURE:
<221> NAME/KEY: misc_feature
<222> LOCATION: (1)..(1)
<223> OTHER INFORMATION: Iowa Black RQ quencher modification
<220> FEATURE:
<221> NAME/KEY: misc_feature
<222> LOCATION: (30)..(30)
<223> OTHER INFORMATION: Cy5 fluorophore modification

<400> SEQUENCE: 13
cgcacctggg ggagtattgc ggaggaaggt                             30

<210> SEQ ID NO 14
<211> LENGTH: 33
<212> TYPE: DNA
<213> ORGANISM: Artificial sequence
<220> FEATURE:
<223> OTHER INFORMATION: aptamer

<400> SEQUENCE: 14
cgcacctggg gaagtattgc ggtggaaggt gcg                         33

<210> SEQ ID NO 15
<211> LENGTH: 34
<212> TYPE: DNA
<213> ORGANISM: Artificial sequence
```

<220> FEATURE:
<223> OTHER INFORMATION: aptamer

<400> SEQUENCE: 15
cctcctacct gggggagtat tgcggaggaa ggta                                34

<210> SEQ ID NO 16
<211> LENGTH: 40
<212> TYPE: DNA
<213> ORGANISM: Artificial sequence
<220> FEATURE:
<223> OTHER INFORMATION: aptamer
<220> FEATURE:
<221> NAME/KEY: misc_feature
<222> LOCATION: (1)..(1)
<223> OTHER INFORMATION: Cy5 fluorophore modification
<220> FEATURE:
<221> NAME/KEY: misc_feature
<222> LOCATION: (40)..(40)
<223> OTHER INFORMATION: Iowa Black RQ quencher modification

<400> SEQUENCE: 16
gcgagccttc ctccgcaata ctcccccagg tgcggctcgc                          40

<210> SEQ ID NO 17
<211> LENGTH: 37
<212> TYPE: DNA
<213> ORGANISM: Artificial sequence
<220> FEATURE:
<223> OTHER INFORMATION: aptamer

<400> SEQUENCE: 17
tcgggacgtg gattttccgc atacgaagtt gtcccga                             37

<210> SEQ ID NO 18
<211> LENGTH: 34
<212> TYPE: DNA
<213> ORGANISM: Artificial sequence
<220> FEATURE:
<223> OTHER INFORMATION: aptamer

<400> SEQUENCE: 18
tcgggacgtg gattttccgc atacgaagtt gtcc                                34

<210> SEQ ID NO 19
<211> LENGTH: 33
<212> TYPE: DNA
<213> ORGANISM: Artificial sequence
<220> FEATURE:
<223> OTHER INFORMATION: aptamer

<400> SEQUENCE: 19
tcgggacgtg gattttccgc atacgaagtt gtc                                 33

<210> SEQ ID NO 20
<211> LENGTH: 30
<212> TYPE: DNA
<213> ORGANISM: Artificial sequence
<220> FEATURE:
<223> OTHER INFORMATION: aptamer

<400> SEQUENCE: 20
tcgggacgtg gattttccgc atacgaagtt                                     30

<210> SEQ ID NO 21
<211> LENGTH: 37
<212> TYPE: DNA

```
<213> ORGANISM: Artificial sequence
<220> FEATURE:
<223> OTHER INFORMATION: aptamer

<400> SEQUENCE: 21
tcgggacgtg gattttccgc ctacgaagtc gtcccga                                   37

<210> SEQ ID NO 22
<211> LENGTH: 38
<212> TYPE: DNA
<213> ORGANISM: Artificial sequence
<220> FEATURE:
<223> OTHER INFORMATION: aptamer

<400> SEQUENCE: 22
gggtgacaag gaaaatcctt caatgaagtg ggtcaccc                                  38

<210> SEQ ID NO 23
<211> LENGTH: 35
<212> TYPE: DNA
<213> ORGANISM: Artificial sequence
<220> FEATURE:
<223> OTHER INFORMATION: aptamer

<400> SEQUENCE: 23
gggtgacaag gaaaatcctt caatgaagtg ggtca                                     35

<210> SEQ ID NO 24
<211> LENGTH: 33
<212> TYPE: DNA
<213> ORGANISM: Artificial sequence
<220> FEATURE:
<223> OTHER INFORMATION: aptamer

<400> SEQUENCE: 24
gggtgacaag gaaaatcctt caatgaagtg ggt                                       33

<210> SEQ ID NO 25
<211> LENGTH: 38
<212> TYPE: DNA
<213> ORGANISM: Artificial sequence
<220> FEATURE:
<223> OTHER INFORMATION: aptamer

<400> SEQUENCE: 25
gggtgacaag gaaaatcctt cgatgaagtg ggtcaccc                                  38

<210> SEQ ID NO 26
<211> LENGTH: 45
<212> TYPE: DNA
<213> ORGANISM: Artificial sequence
<220> FEATURE:
<223> OTHER INFORMATION: aptamer
<220> FEATURE:
<221> NAME/KEY: misc_feature
<222> LOCATION: (1)..(1)
<223> OTHER INFORMATION: FAM (6-carboxyfluroescein) modification
<220> FEATURE:
<221> NAME/KEY: misc_feature
<222> LOCATION: (45)..(45)
<223> OTHER INFORMATION: Blackhole Quencher 1 modification

<400> SEQUENCE: 26
gcgagcaccc acttcattga aggattttcc ttgtcacccg ctcgc                          45

<210> SEQ ID NO 27
<211> LENGTH: 32
```

<212> TYPE: DNA
<213> ORGANISM: Artificial sequence
<220> FEATURE:
<223> OTHER INFORMATION: DNA ladder

<400> SEQUENCE: 27
gggagacaag gaaaatcctt caatgaagtg gg                                    32

<210> SEQ ID NO 28
<211> LENGTH: 29
<212> TYPE: DNA
<213> ORGANISM: Artificial sequence
<220> FEATURE:
<223> OTHER INFORMATION: DNA ladder

<400> SEQUENCE: 28
gggagacaag gaaaatcctt caatgaagt                                        29

<210> SEQ ID NO 29
<211> LENGTH: 26
<212> TYPE: DNA
<213> ORGANISM: Artificial sequence
<220> FEATURE:
<223> OTHER INFORMATION: DNA ladder

<400> SEQUENCE: 29
gggagacaag gaaaatcctt caatga                                           26

<210> SEQ ID NO 30
<211> LENGTH: 23
<212> TYPE: DNA
<213> ORGANISM: Artificial sequence
<220> FEATURE:
<223> OTHER INFORMATION: DNA ladder

<400> SEQUENCE: 30
gggagacaag gaaaatcctt caa                                              23

<210> SEQ ID NO 31
<211> LENGTH: 20
<212> TYPE: DNA
<213> ORGANISM: Artificial sequence
<220> FEATURE:
<223> OTHER INFORMATION: DNA ladder

<400> SEQUENCE: 31
gggagacaag gaaaatcctt                                                  20

<210> SEQ ID NO 32
<211> LENGTH: 17
<212> TYPE: DNA
<213> ORGANISM: Artificial sequence
<220> FEATURE:
<223> OTHER INFORMATION: DNA ladder

<400> SEQUENCE: 32
gggagacaag gaaaatc                                                     17

<210> SEQ ID NO 33
<211> LENGTH: 14
<212> TYPE: DNA
<213> ORGANISM: Artificial sequence
<220> FEATURE:
<223> OTHER INFORMATION: DNA ladder

<400> SEQUENCE: 33
gggagacaag gaaa                                                              14

<210> SEQ ID NO 34
<211> LENGTH: 11
<212> TYPE: DNA
<213> ORGANISM: Artificial sequence
<220> FEATURE:
<223> OTHER INFORMATION: DNA ladder

<400> SEQUENCE: 34
gggagacaag g                                                                 11

<210> SEQ ID NO 35
<211> LENGTH: 46
<212> TYPE: DNA
<213> ORGANISM: Artificial sequence
<220> FEATURE:
<223> OTHER INFORMATION: aptamer

<400> SEQUENCE: 35
cttacgacct taagtggggt tcgggtggag tttatggggt cgtaag                           46

<210> SEQ ID NO 36
<211> LENGTH: 40
<212> TYPE: DNA
<213> ORGANISM: Artificial sequence
<220> FEATURE:
<223> OTHER INFORMATION: aptamer

<400> SEQUENCE: 36
cttacgacct taagtggggt tcgggtggag tttatggggt                                  40

<210> SEQ ID NO 37
<211> LENGTH: 46
<212> TYPE: DNA
<213> ORGANISM: Artificial sequence
<220> FEATURE:
<223> OTHER INFORMATION: aptamer

<400> SEQUENCE: 37
cttacgactg agaagtgtga ttcagtatgt tttccgaagt cgtaag                           46

<210> SEQ ID NO 38
<211> LENGTH: 40
<212> TYPE: DNA
<213> ORGANISM: Artificial sequence
<220> FEATURE:
<223> OTHER INFORMATION: aptamer

<400> SEQUENCE: 38
cttacgactg agaagtgtga ttcagtatgt tttccgaagt                                  40

<210> SEQ ID NO 39
<211> LENGTH: 34
<212> TYPE: DNA
<213> ORGANISM: Artificial sequence
<220> FEATURE:
<223> OTHER INFORMATION: aptamer
<220> FEATURE:
<221> NAME/KEY: misc_feature
<222> LOCATION: (1)..(1)
<223> OTHER INFORMATION: thiol modification
<220> FEATURE:
<221> NAME/KEY: misc_feature
<222> LOCATION: (1)..(1)
<223> OTHER INFORMATION: (CH2)6 linker
<220> FEATURE:
<221> NAME/KEY: misc_feature

```
<222> LOCATION: (34)..(34)
<223> OTHER INFORMATION: methylene blue modification

<400> SEQUENCE: 39
accttaagtg gggttcgggt ggagtttatg gggt                           34

<210> SEQ ID NO 40
<211> LENGTH: 34
<212> TYPE: DNA
<213> ORGANISM: Artificial sequence
<220> FEATURE:
<223> OTHER INFORMATION: aptamer
<220> FEATURE:
<221> NAME/KEY: misc_feature
<222> LOCATION: (1)..(1)
<223> OTHER INFORMATION: thiol modification
<220> FEATURE:
<221> NAME/KEY: misc_feature
<222> LOCATION: (1)..(1)
<223> OTHER INFORMATION: (CH2)6 linker
<220> FEATURE:
<221> NAME/KEY: misc_feature
<222> LOCATION: (34)..(34)
<223> OTHER INFORMATION: methylene blue modification

<400> SEQUENCE: 40
cttacgactg agaagtgtga ttcagtatgt tttc                           34

<210> SEQ ID NO 41
<211> LENGTH: 33
<212> TYPE: DNA
<213> ORGANISM: Artificial sequence
<220> FEATURE:
<223> OTHER INFORMATION: aptamer

<400> SEQUENCE: 41
cctcctacct gggggagtat tgcggaggaa ggt                            33

<210> SEQ ID NO 42
<211> LENGTH: 25
<212> TYPE: DNA
<213> ORGANISM: Artificial sequence
<220> FEATURE:
<223> OTHER INFORMATION: aptamer

<400> SEQUENCE: 42
cctcctacct gggggagtat tgcgg                                     25
```